United States Patent
Chehab et al.

(10) Patent No.: US 12,296,118 B2
(45) Date of Patent: May 13, 2025

(54) SYSTEMS AND METHODS FOR SECURING CATHETERS

(71) Applicant: Novonate, Inc., South San Francisco, CA (US)

(72) Inventors: Eric Fayez Chehab, San Francisco, CA (US); Eric Johnson, Woodside, CA (US); Eric Anthony Kramer, Los Altos Hills, CA (US); Marlo Dreissigacker Kohn, Redwood City, CA (US); James Kennedy Wall, Woodside, CA (US); Ross Daniel Venook, Millbrae, CA (US); Shivani Alexandra Torres, San Francisco, CA (US); Cerys Rohann Murray-Scott, Fortrose (GB); Marisa Janelle San Agustin Borja, San Francisco, CA (US)

(73) Assignee: Novonate, Inc., South San Francisco, CA (US)

( * ) Notice: Subject to any disclaimer, the term of this patent is extended or adjusted under 35 U.S.C. 154(b) by 0 days.

(21) Appl. No.: 18/658,880

(22) Filed: May 8, 2024

(65) Prior Publication Data
US 2024/0382718 A1   Nov. 21, 2024

Related U.S. Application Data

(63) Continuation of application No. 17/128,796, filed on Dec. 21, 2020, now Pat. No. 11,980,725, which is a
(Continued)

(51) Int. Cl.
*A61M 25/02* (2006.01)

(52) U.S. Cl.
CPC ....... *A61M 25/02* (2013.01); *A61M 2025/024* (2013.01); *A61M 2025/0273* (2013.01); *A61M 2025/028* (2013.01); *A61M 2240/00* (2013.01)

(58) Field of Classification Search
CPC ............ A61M 25/02; A61M 2025/024; A61M 2025/0273; A61M 2025/028; A61M 2240/00
(Continued)

(56) References Cited

U.S. PATENT DOCUMENTS

| 2,652,827 A | 9/1953 | Smith |
| 3,194,235 A | 7/1965 | Cooke |

(Continued)

FOREIGN PATENT DOCUMENTS

| CN | 101822552 | 9/2010 |
| CN | 101849847 | 10/2010 |

(Continued)

OTHER PUBLICATIONS

International Search Report and Written Opinion dated Sep. 13, 2019 for PCT Application No. PCT/US2019/038595, in 16 pages.

*Primary Examiner* — Phillip A Gray
(74) *Attorney, Agent, or Firm* — Knobbe, Martens, Olson & Bear, LLP

(57) ABSTRACT

A catheter interface protection device can include a shield. The shield can include an open bottom, a transparent upper surface, sidewalls, and a cavity at least partially defined by the bottom, the upper surface, and the sidewalls. The device can include a vent. The device can include a clip, a tether, and a latch. A non-therapeutic method of protecting a catheter interface can include extending a catheter in the subject through a slot in a catheter interface protection device, wrapping the catheter at least partially around a clip of the catheter interface protection device, and securing a latch of the catheter interface protection device around the clip. A device for positioning a subject in a prone position can include a padded area including an opening configured to accommodate a catheter interface protection device.

20 Claims, 30 Drawing Sheets

Related U.S. Application Data continuation of application No. PCT/US2019/038595, filed on Jun. 21, 2019.

(60) Provisional application No. 62/689,463, filed on Jun. 25, 2018.

(58) Field of Classification Search
USPC .......................................................... 604/174
See application file for complete search history.

(56) References Cited

U.S. PATENT DOCUMENTS

| | | |
|---|---|---|
| 3,674,032 A | 7/1972 | Minganti |
| 4,353,369 A | 10/1982 | Muetterties et al. |
| 4,516,968 A | 5/1985 | Marshall et al. |
| 4,699,616 A | 10/1987 | Nowak et al. |
| 4,915,694 A | 4/1990 | Yamamoto et al. |
| D315,822 S | 3/1991 | Ryan |
| 5,006,830 A | 4/1991 | Merritt |
| 5,116,324 A | 5/1992 | Brierley et al. |
| 5,370,627 A | 12/1994 | Conway |
| 6,866,652 B2 | 3/2005 | Bierman |
| 6,875,200 B1 | 4/2005 | Ajagbe |
| 7,347,842 B2 | 3/2008 | Thorne et al. |
| D613,857 S | 4/2010 | Bierman |
| D613,858 S | 4/2010 | Bierman |
| D613,859 S | 4/2010 | Bierman |
| 8,052,648 B2 | 11/2011 | Dikeman et al. |
| 8,057,440 B2 | 11/2011 | Bierman |
| 8,269,059 B2 | 9/2012 | Wright |
| 8,556,859 B2 | 10/2013 | Nilson et al. |
| 8,617,115 B2 | 12/2013 | Kennard et al. |
| 8,641,613 B2 | 2/2014 | Coelho |
| 8,641,614 B2 | 2/2014 | Coelho |
| 9,174,027 B2 | 11/2015 | Kennard |
| 9,220,870 B2 | 12/2015 | Hyman et al. |
| D817,482 S | 5/2018 | Howell et al. |
| D819,802 S | 6/2018 | Burkholz et al. |
| D835,262 S | 12/2018 | Burkholz et al. |
| 10,441,727 B2 | 10/2019 | Shimer et al. |
| 10,471,235 B2 | 11/2019 | Dambkowski et al. |
| D876,621 S | 2/2020 | Olson et al. |
| 10,814,106 B2 | 10/2020 | Garrison |
| D907,768 S | 1/2021 | Chehab et al. |
| D921,888 S | 6/2021 | Chehab et al. |
| 11,135,402 B2 | 10/2021 | Dambkowski et al. |
| 2004/0102736 A1 | 5/2004 | Bierman |
| 2005/0113759 A1 | 5/2005 | Mueller et al. |
| 2006/0084903 A1 | 4/2006 | Keeley |
| 2006/0264836 A1 | 11/2006 | Bierman |
| 2007/0055205 A1 | 3/2007 | Wright |
| 2008/0202531 A1 | 8/2008 | Fletcher |
| 2009/0143740 A1 | 6/2009 | Bierman et al. |
| 2010/0179481 A1 | 7/2010 | Bierman et al. |
| 2010/0228090 A1 | 9/2010 | Weisenburgh, II et al. |
| 2010/0324491 A1 | 12/2010 | Bierman et al. |
| 2011/0282290 A1 | 11/2011 | Kennard et al. |
| 2011/0282291 A1 | 11/2011 | Ciccone |
| 2012/0179119 A1 | 7/2012 | Ng et al. |
| 2012/0232356 A1 | 9/2012 | Coelho |
| 2013/0053785 A1 | 2/2013 | Parvatiyar et al. |
| 2013/0237928 A1 | 9/2013 | Fisher et al. |
| 2013/0345639 A1 | 12/2013 | Spittler |
| 2014/0060548 A1 | 3/2014 | Check |
| 2017/0021134 A1* | 1/2017 | Dambkowski ........ A61F 15/008 |
| 2017/0143941 A1 | 5/2017 | Augustine et al. |
| 2018/0207398 A1 | 7/2018 | Jho |
| 2018/0250472 A1 | 9/2018 | Anderson et al. |
| 2020/0023165 A1 | 1/2020 | Dambkowski et al. |
| 2020/0330733 A1 | 10/2020 | Howell |
| 2021/0106790 A1 | 4/2021 | Chehab et al. |
| 2021/0393922 A1 | 12/2021 | Dambkowski et al. |

FOREIGN PATENT DOCUMENTS

| | | |
|---|---|---|
| CN | 102006904 | 4/2011 |
| CN | 202154774 | 3/2012 |
| CN | 103156732 | 6/2013 |
| CN | 203389010 | 1/2014 |
| CN | 103635225 | 3/2014 |
| CN | 103732268 | 4/2014 |
| CN | 103735370 | 4/2014 |
| CN | 203677702 | 7/2014 |
| CN | 204158799 | 2/2015 |
| CN | 204170268 | 2/2015 |
| JP | 2008516656 | 5/2008 |
| JP | 2008302237 | 12/2008 |
| JP | 2014534001 | 12/2014 |
| JP | 5781848 | 9/2015 |
| JP | 2015163191 | 9/2015 |
| JP | 2018515189 | 11/2016 |
| WO | WO 2016/178804 | 11/2016 |
| WO | WO 2021/127270 | 6/2021 |

\* cited by examiner

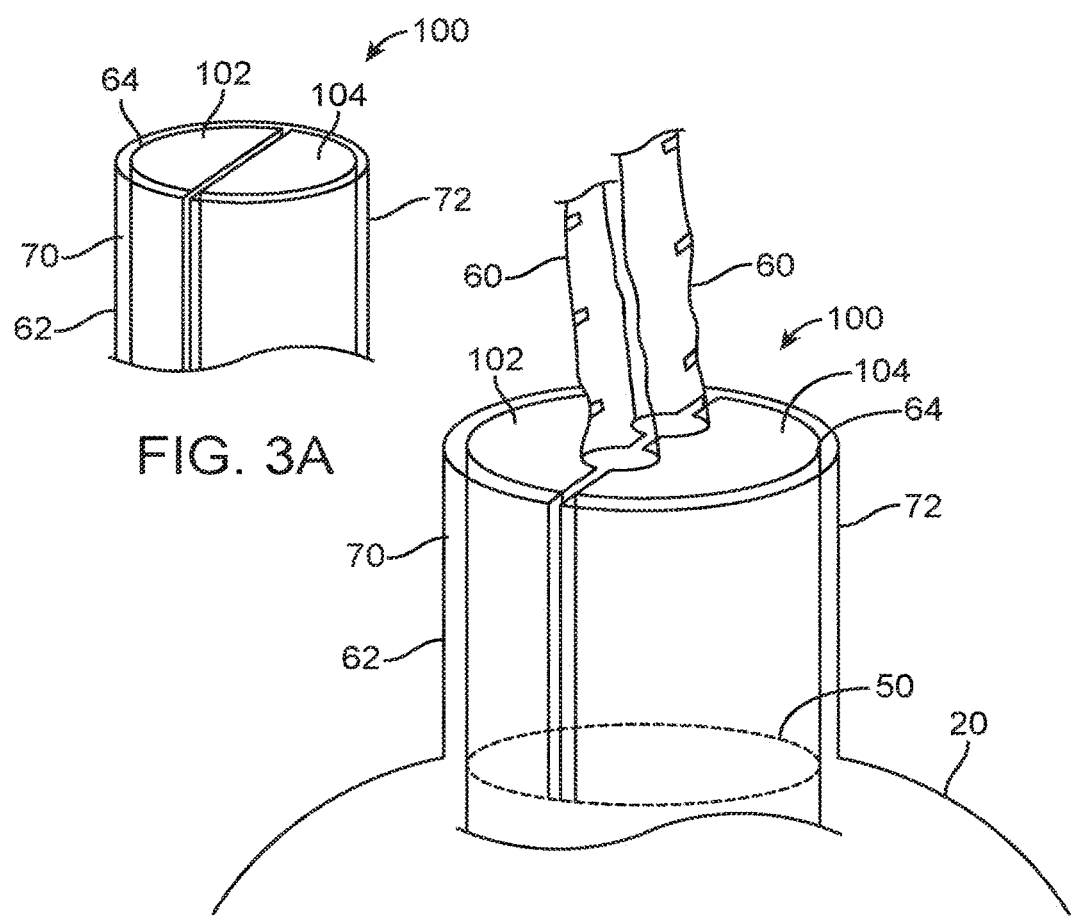
FIG. 3A
FIG. 3B
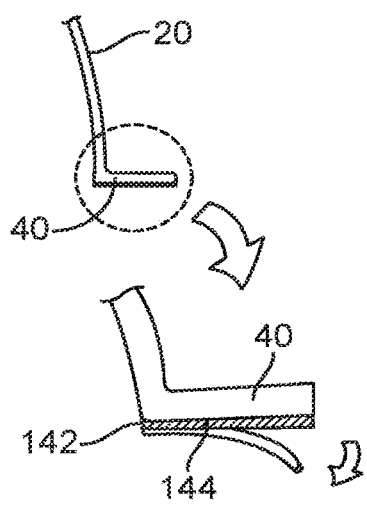
FIG. 4
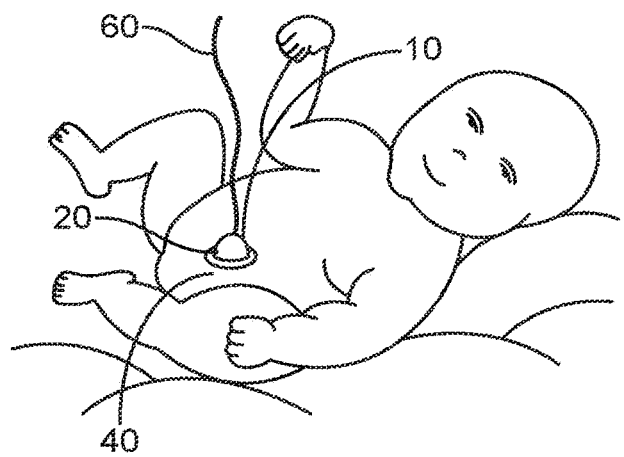
FIG. 5

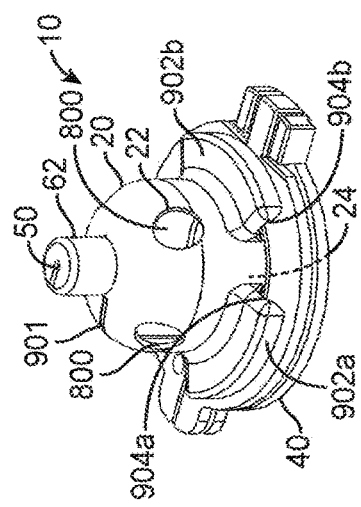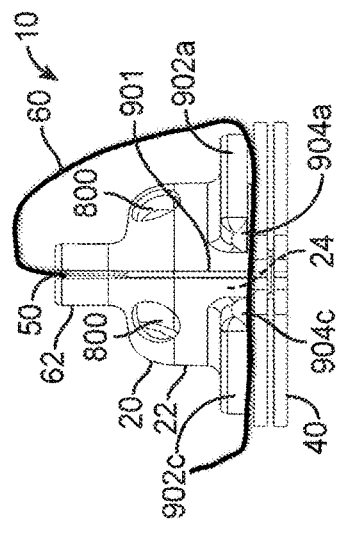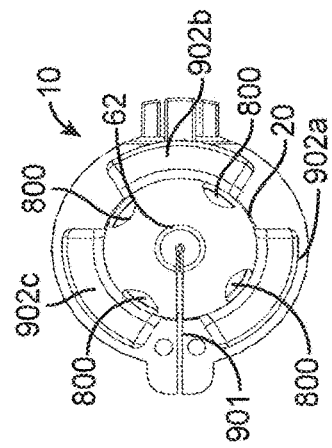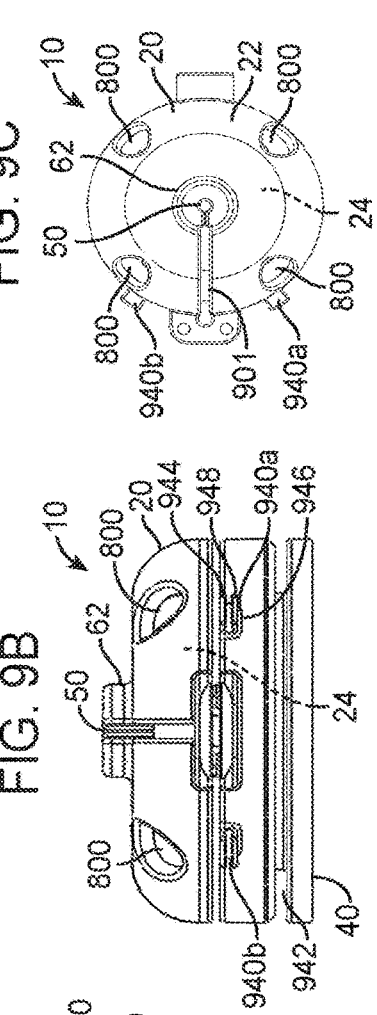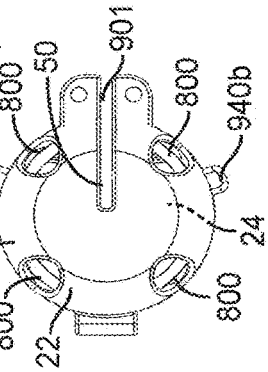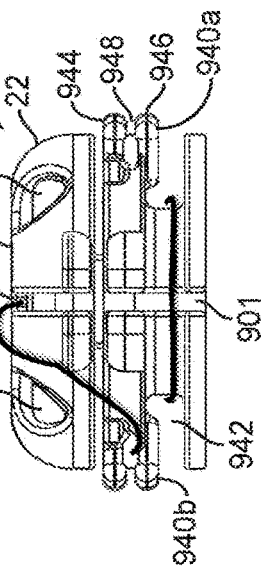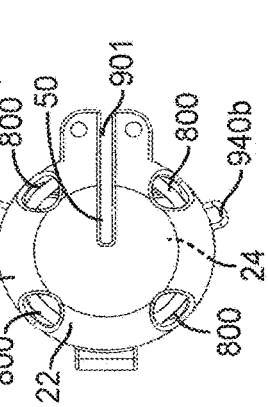

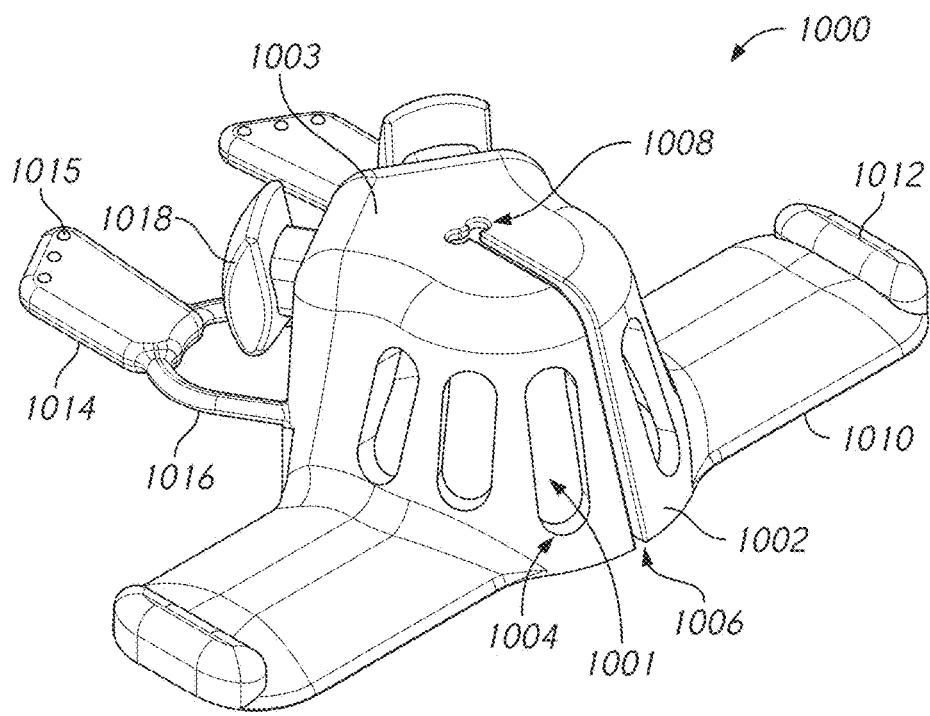
FIG. 20Ai
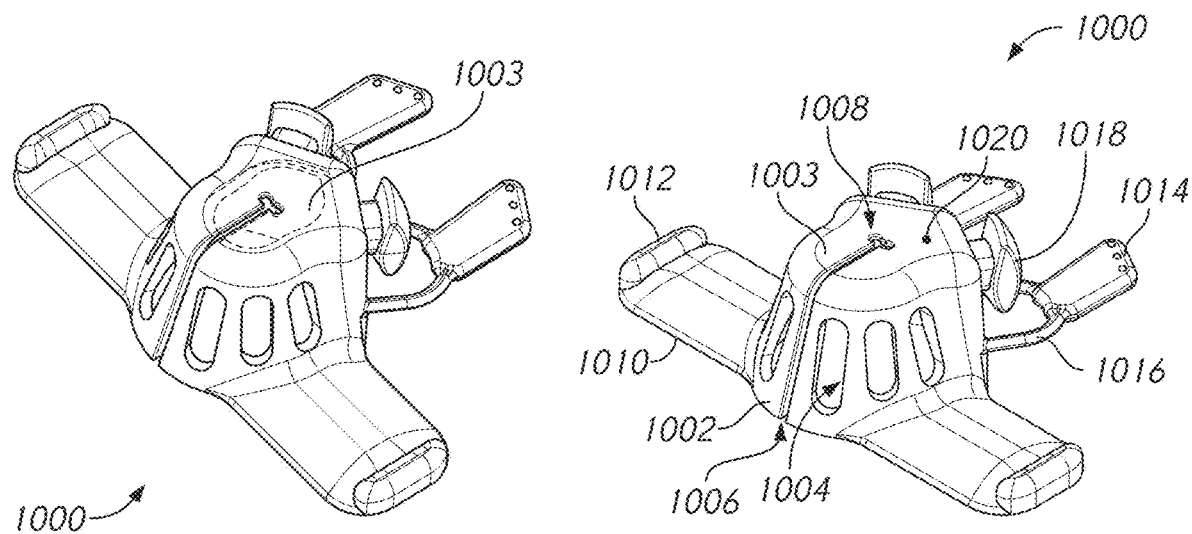
FIG. 20Aii
FIG. 20Aiii

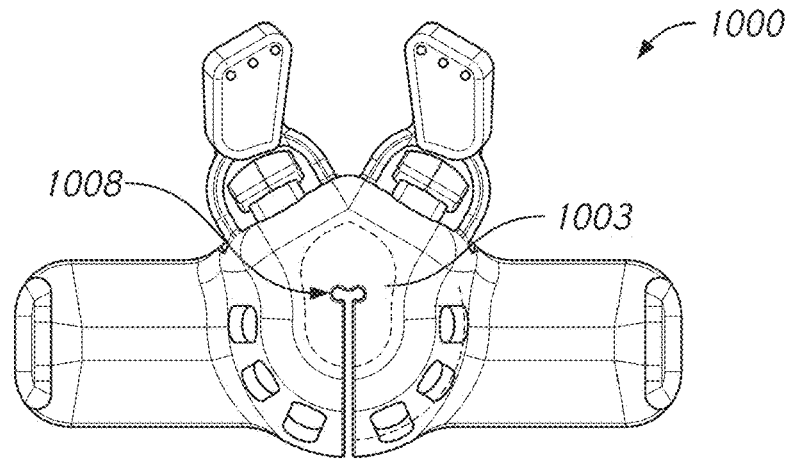
FIG. 20Bi
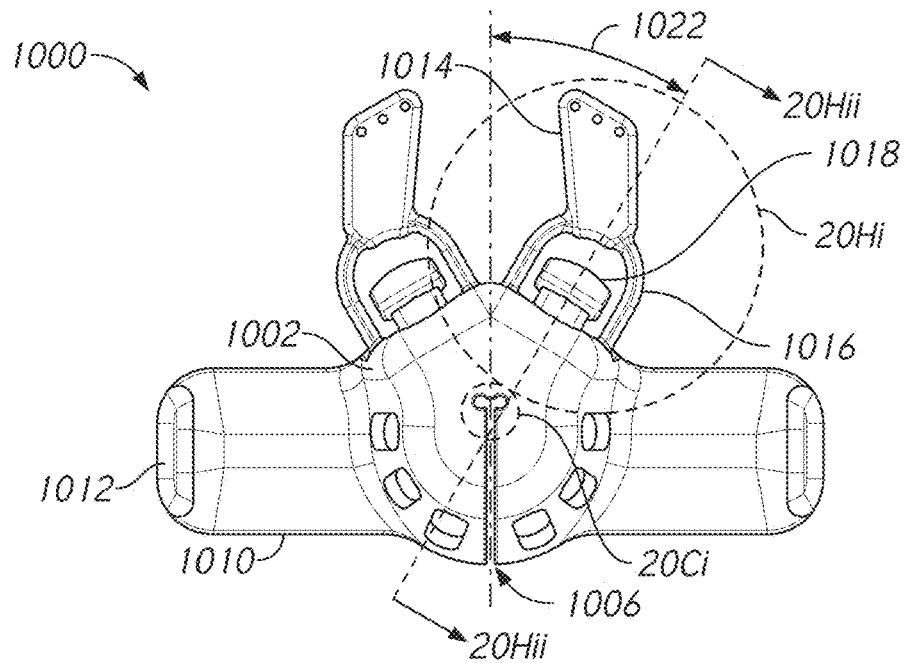
FIG. 20Bii
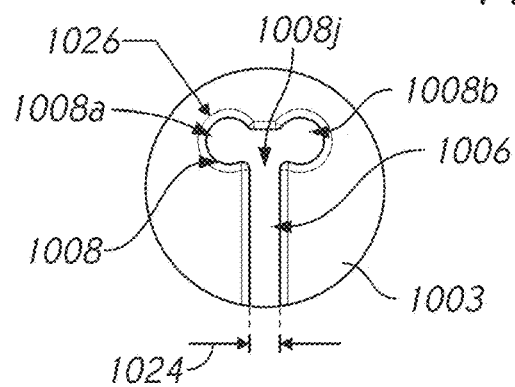
FIG. 20Ci
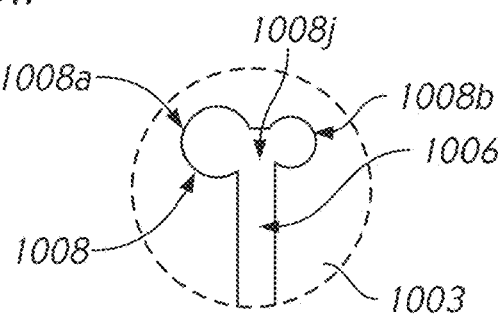
FIG. 20Cii

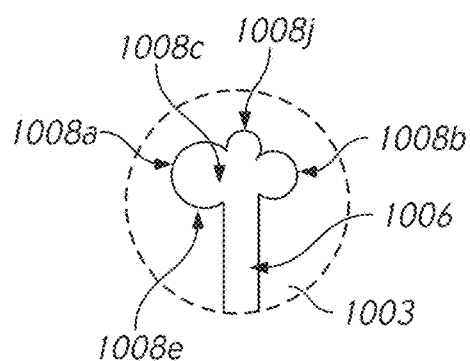
FIG. 20Ciii
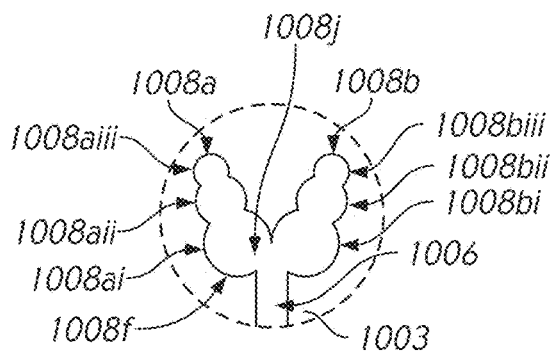
FIG. 20Civ
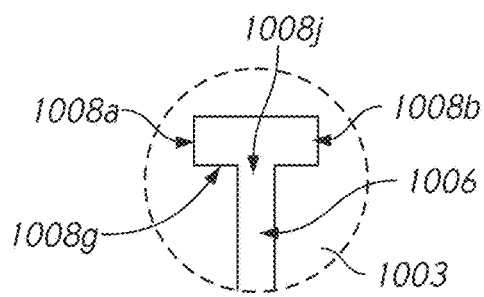
FIG. 20Cv
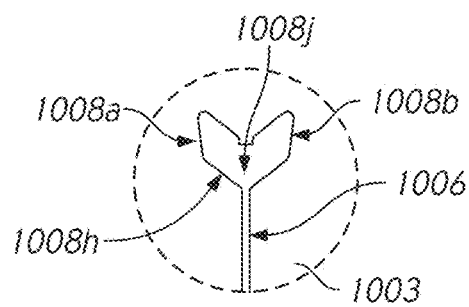
FIG. 20Cvi
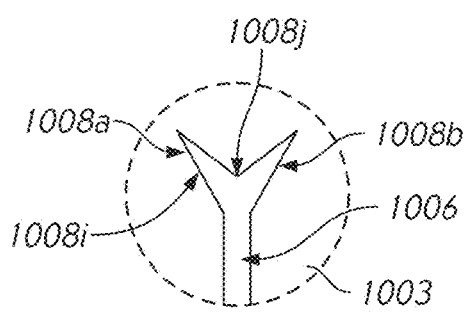
FIG. 20Cvii
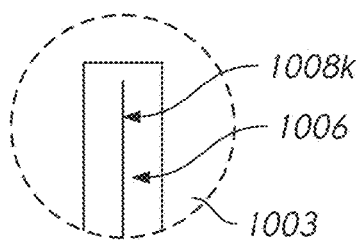
FIG. 20Cviii

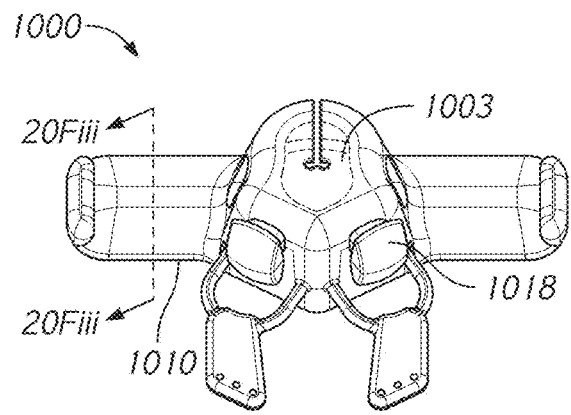
FIG. 20D
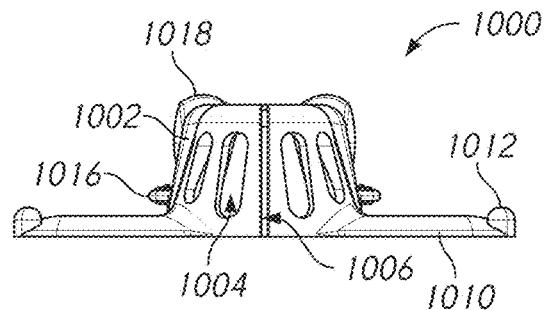
FIG. 20E
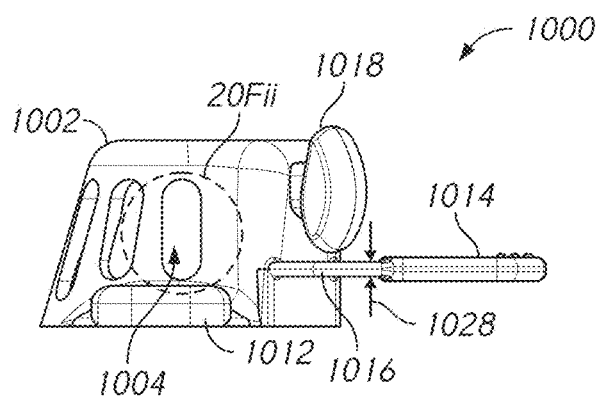
FIG. 20Fi
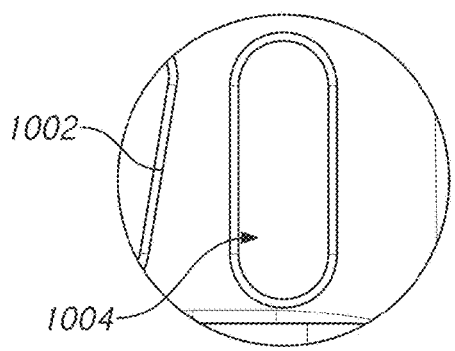
FIG. 20Fii
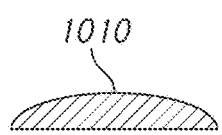
FIG. 20Fiii
FIG. 20Fiv
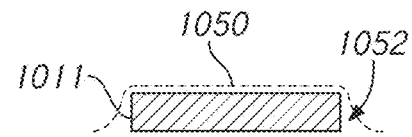
FIG. 20Fv

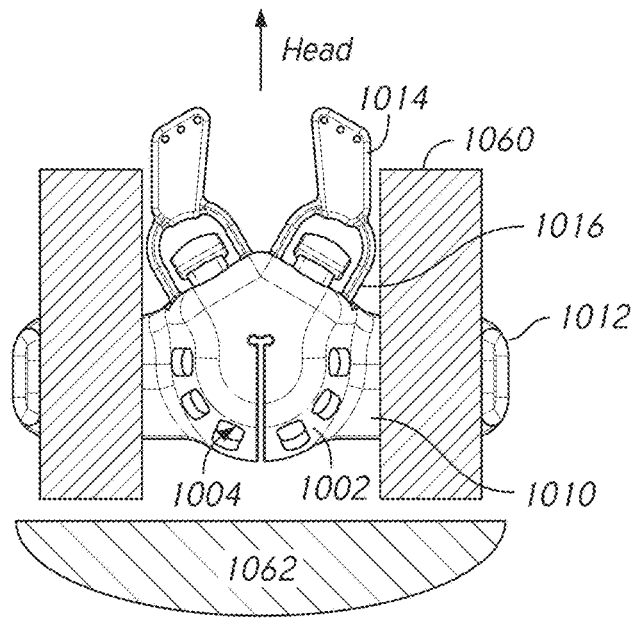
FIG. 20G
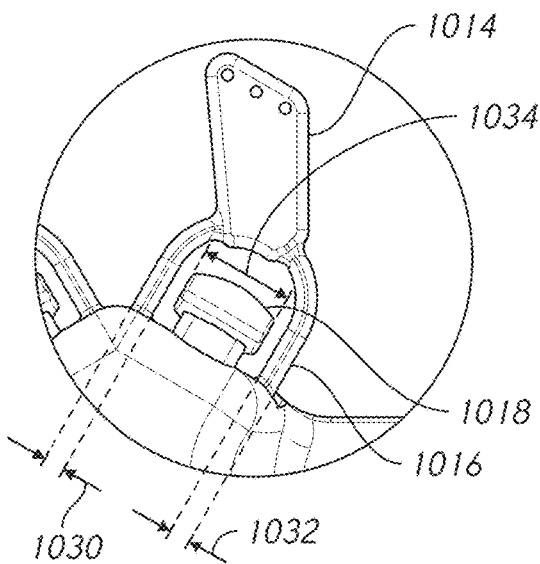
FIG. 20Hi
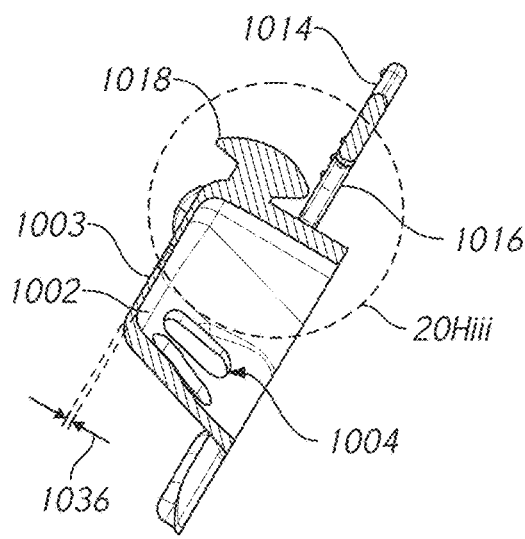
FIG. 20Hii
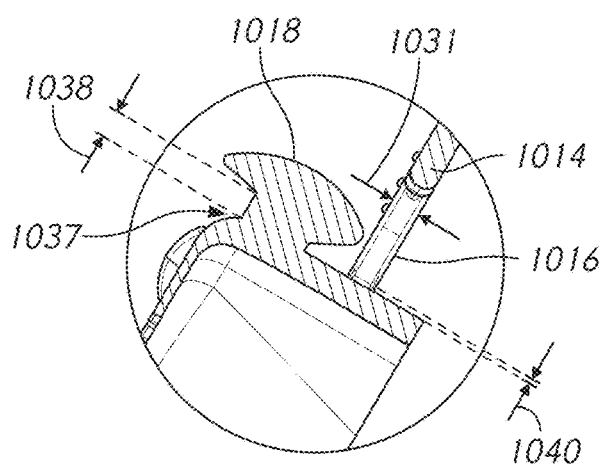
FIG. 20Hiii

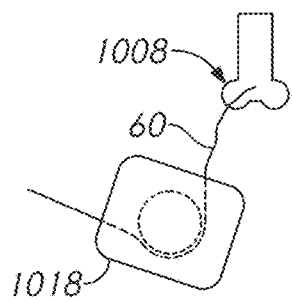
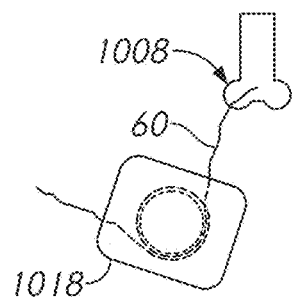
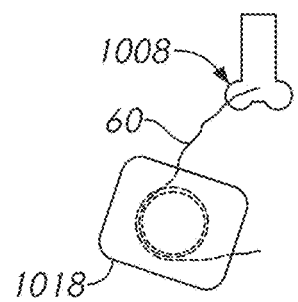
FIG. 22A          FIG. 22B          FIG. 22C
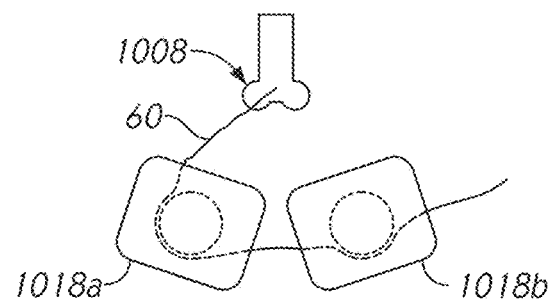
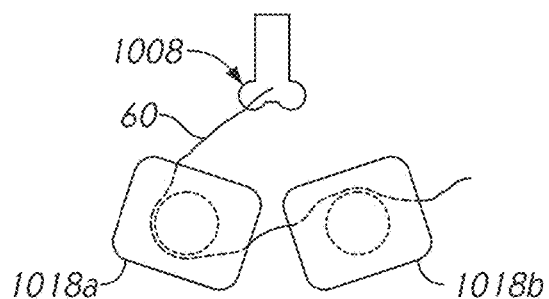
FIG. 22D                    FIG. 22E
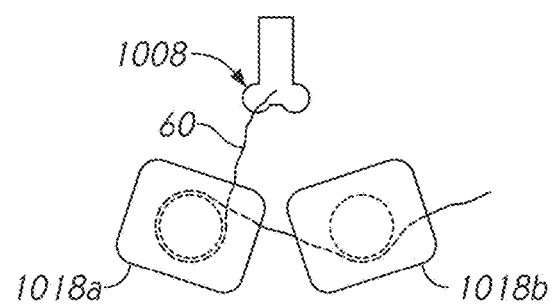
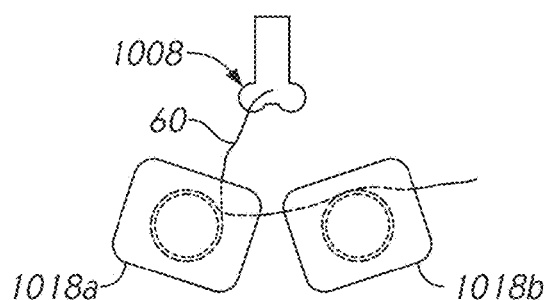
FIG. 22F                    FIG. 22G

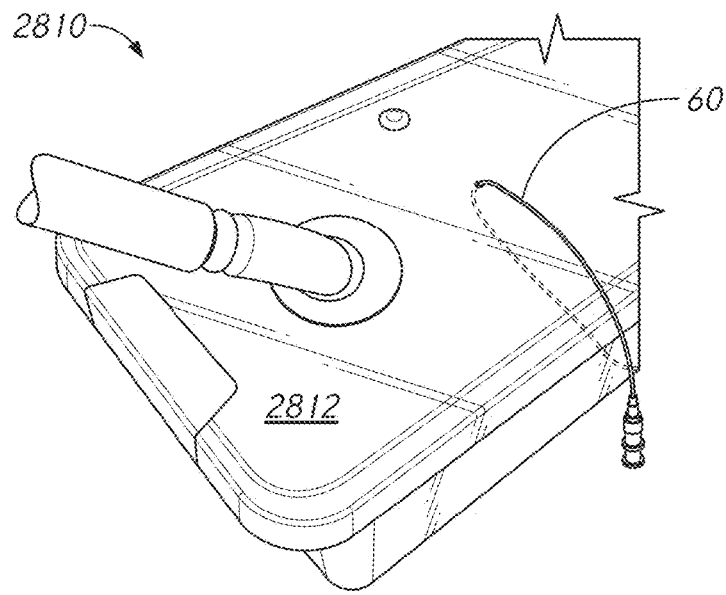
FIG. 28Bi
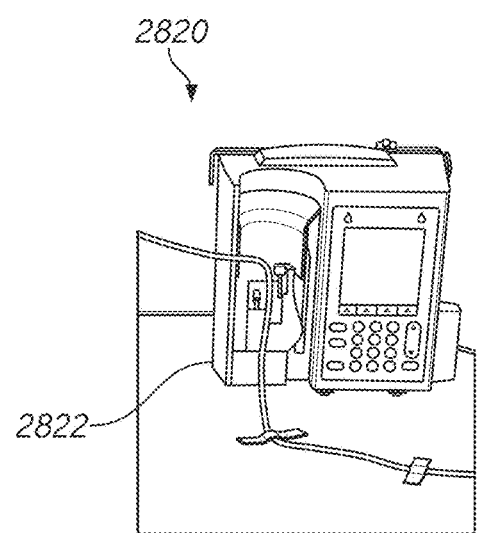
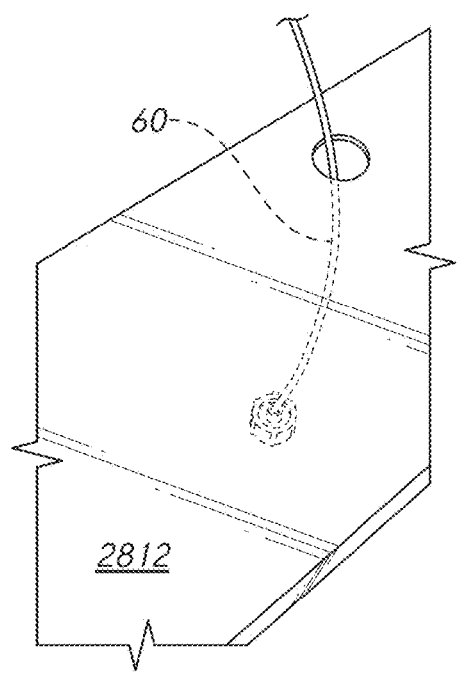
FIG. 28Bii
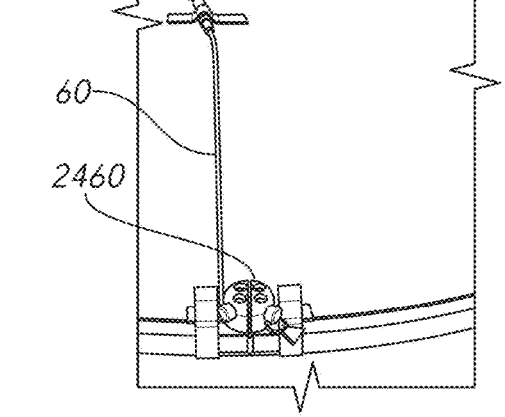
FIG. 28C

SYSTEMS AND METHODS FOR SECURING CATHETERS

INCORPORATION BY REFERENCE

The present application is a continuation of application Ser. No. 17/128,796, filed Dec. 21, 2020, which is continuation of Patent Cooperation Treaty App. No. PCT/US2019/038595, filed Jun. 21, 2019, which claims priority benefit of U.S. Provisional Patent App. No. 62/689,463, filed Jun. 25, 2018, each of which is incorporated herein by reference in its entirety for all purposes.

BACKGROUND

Field

The application relates to umbilical devices, and, more particularly, to systems and methods for protecting umbilical stumps.

Description of the Related Art

Every year, more than 5 million central venous catheters (also called central lines) are placed by physicians. Central lines facilitate the delivery of medication and nutritional support to a patient, but can lead to a hospital acquired bloodstream infection. Associated symptoms of central line-associated bloodstream infections (CLABSIs) are sepsis, fever, and malaise. CLABSIs are a major concern for hospitals because they have been associated with increased morbidity and mortality, length of hospital stay, and cost.

Complications associated with low birth weight and premature infants make it necessary for many of these neonates to be admitted to the neonatal intensive care unit (NICU), where a majority of them receives umbilical catheters. Premature infants are particularly vulnerable to bloodstream infections due to their immature immune systems, poor skin integrity, exposure to numerous caregivers, placement in an environment that is conducive to bacterial colonization, and their subjection to repeated invasive procedures. Indeed, the rate of CLABSIs in these infants is far greater than that of adults.

Although umbilical catheterization is a necessary and life-saving procedure for many premature infants, outcomes from CLABSIs can be devastating. Catheter-related bloodstream infections in premature infants are associated with increased morbidity and mortality. Infants with CLABSIs have an increased risk for respiratory distress, severe intraventricular hemorrhage, periventricular leukomalacia, bronchopulmonary dysplasia, and death. CLABSIs are the most common cause of complications related to umbilical catheters, with approximately 5-15% of neonates with umbilical catheters developing CLABSIs. The rate is highest for the lowest birth weight infants, weighing under 1250 grams, who have umbilical catheter CLABSI rates of 15% or more.

Placement of an umbilical catheter is a delicate, multistep process. First, the cord is elevated vertically and cut approximately one centimeter above the skin with a scalpel blade. Second, the closed tips of forceps are positioned in the umbilical vein or artery in order to dilate the vessel. Third, the catheter is introduced into the vessel and advanced 4-5 centimeters. This step may be repeated if the catheter is not properly inserted. Fourth, blood is aspirated to verify catheter placement in the lumen and 0.5 mL of heparin is flushed to clear the lumen. Finally, the catheter is advanced to a predetermined length (based on height and weight of the neonate), attached to the umbilical stump with a suture, and the line is secured with a catheter bridge (sometimes made of surgical tape). Ideal placement of an umbilical venous catheter is at the junction of the inferior vena cava (IVC) and the right atrium of the heart.

Despite high complication risks, umbilical catheters remain the preferred route of catheterization in the NICU because they offer reliable access to the venous system with the necessary flow required to deliver these premature, and often sick, neonates medication, fluids, and parenteral nutrition. Umbilical catheters can also be used to monitor blood pressure and sample venous or arterial blood. With current technologies, physicians remove the umbilical catheter due to risk of CLABSI after approximately 6-8 days, even though there is still typically a need for central access. Indeed, a peripherally inserted central catheter (PICC) line or other form of central catheterization is usually placed in the neonate after UC removal.

Umbilical catheter CLABSIs are at least 5 times more common than central catheter associated bloodstream infections. One possible reason for this is that there is no device that is specific to the unique anatomy of the umbilical area or the unique demands of the neonate that can both protect the umbilical stump and stabilize the umbilical catheter(s).

SUMMARY

In some embodiments, a device for protecting an umbilical stump-catheter interface comprises a shield. The shield has a wall. The wall at least partially defines a cavity configured to accommodate an umbilical stump. The shield further includes a base configured to attachment to a subject. The device further includes an opening in the shield. The opening in the shield is configured to allow an umbilical catheter to extend therethrough.

In some embodiments, a device for protecting an umbilical stump-catheter interface comprises a shield configured to at least partially surround an umbilical stump. The device further includes an opening in the shield. The opening in the shield is configured to allow an umbilical catheter to extend therethrough.

The opening may be at a top of the shield. The opening at the top of the shield may extend to a side of the shield. The shield may comprise a first clip configured to hold the umbilical catheter. The shield may comprise a second clip. The first clip may be above the second clip to form a stacked configuration. The first clip and the second clip may be disposed at different respective sides of the shield. The first clip may be made from a first material having a first durometer. Another part of the shield may be made from a second material having a second durometer. The first durometer may be higher than the second durometer. The second clip may be configured to hold the umbilical catheter and/or another catheter. The first clip may have a first catheter slot. The second clip may have a second catheter slot. The first catheter slot may have a dimension that is different from a dimension of the second catheter slot. The device may further include a third clip. The first clip may be configured to hold the umbilical catheter. The second clip may be configured to hold a first additional catheter. The third clip may be configured to hold a second additional catheter and/or the umbilical catheter. The first clip and the second clip may be integrated as a single component. The shield may comprise a first portion having a first durometer and a second portion having a second durometer. The first durometer may be higher than the second durometer. The shield may comprise one or more spooling grooves at one or more sides of the shield. The one or more spooling grooves may be configured to accommodate a segment of the umbilical catheter. The shield may comprise a circumferentially disposed spooling groove configured to accommodate a segment of the umbilical catheter. The shield may have a top portion. The shield may further comprise a clip at the top portion for holding and/or guiding the umbilical catheter. The shield may further comprise at least two pinching protrusions at the top portion for allowing a user to grasp the shield. The shield may comprise an exterior surface configured for allowing a user to write on. The shield may comprise a color coding or a labeling. The base may comprise a T-shape portion, a linear portion, or a curvilinear portion, or a full circumferential portion extending away from a side of the shield. The shield may have a first shield portion and a second shield portion that may be moveably coupled to the first shield portion. When the second shield portion is in a first position, the umbilical stump may be shielded by the shield. When the second shield portion is in a second position, the umbilical stump may be exposed to an environment outside the shield. The device may further comprise a mechanical hinge configured to rotatably couple the second shield portion to the first shield portion. The second shield portion may be moveable relative to the first shield portion in a plane parallel to the base. The device may further include a securing device configured to lock the second shield portion relative to the first shield portion when the second shield portion is in the first position. The device may further include a seal located at or adjacent the opening. The seal may have a first seal portion that may be coupled to the first shield portion. The seal may have a second seal portion that may be coupled to the second shield portion. At least a part of the shield may have a dome shape. The device may further include a tubular structure extending from the dome shape shield. The tubular structure may have a channel that extends from the opening. The tubular structure may be at a top of the dome shape shield. The device may further include a seal located at or adjacent the opening. The seal may have a first seal portion and a second seal portion that cooperates with the first seal portion to secure an umbilical catheter relative to the device. A majority of the shield may be rigid. The shield may be non-rigid. The shield may be collapsible in response to a compression force that may be less than about 1 lb (e.g., 1 lb). The device may further include an adhesive at the base configured to attach the base to a patient. The base may include one or more openings or slots configured to provide suction. The device may further include a spring-loaded device configured to secure the umbilical catheter relative to the device. At least a part of the shield may be transparent. The device may further include a seal configured to mechanically hold an umbilical catheter. The seal may be configured to protect the umbilical stump from bacteria associated with the umbilical catheter. The shield may be configured to protect the umbilical stump from bacteria outside the shield and/or from physical contact. The shield may comprise a vent configured to allow air exchange through the wall of the shield. The device may further include a permeable or semipermeable cover covering the vent. The device may further include a cover that can be selectively opened to expose the vent or closed to shut the vent. The opening may be at a side of the shield. The opening may be at an upper portion of the shield. The opening may be offset from a center of the shield. The base, an inner surface of the shield, an outer surface of the shield, an entirety of the shield, etc. may include an antimicrobial material. The device may further include an ultraviolet light source coupled to the shield. The shield may have a width that is less than about 5 inches (e.g., less than 5 inches). The device may further include a manual control mechanism configured to shut the umbilical catheter so that fluid flow in the umbilical catheter can be stopped. The device may further include a position monitoring device for monitoring a position of the umbilical catheter with respect to the shield, to the patient, and/or to the umbilical stump.

In some embodiments, a kit may include any of the devices as described previously; and at least one of, at least two of, etc.: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and/or a gauze pad.

The kit may further include a container having a compartment for housing the device, and one or more additional compartment(s) for housing the scissor, the scalpel, the stopcock, the syringe, the measuring tape, the dilator, the needle, the sterilization material, the catheter, the drape, the sponge, the suture, the umbilical tie, the anesthetic agent, the forceps, the needle holder, the hemostat, the syringe, the bag of sterile saline, the gauze pad, and any combination of two or more of the foregoing.

In some embodiments, a method for protecting an umbilical stump-catheter interface may include providing a device having a shield with a wall that defines a cavity for accommodating an umbilical stump.

The shield may further include a base for attachment to a patient. The device may further include an opening at the shield. The method may further include shielding the umbilical stump from an environment using the shield, and accommodating an umbilical catheter using the opening at the shield.

The device may further include a seal at or adjacent the opening. The method may further comprise protecting the umbilical stump from bacterial associated with the umbilical catheter using the seal. The method may further include stabilizing the umbilical catheter with respect to the device by detachably securing the umbilical catheter to the device.

In some embodiments, a catheter interface protection device comprises a shield comprising an open bottom, a transparent upper surface, sidewalls, and a cavity at least partially defined by the bottom, the upper surface, and the sidewalls.

In some embodiments, a catheter interface protection device comprises a shield comprising an open bottom, a flat upper surface, sidewalls, a cavity at least partially defined by the bottom, the upper surface, and the sidewalls.

In some embodiments, a catheter interface protection device comprises a shield comprising an open bottom, an upper surface comprising an opening, sidewalls, and a cavity at least partially defined by the bottom, the upper surface, and the sidewalls.

In some embodiments, a catheter interface protection device comprises a shield comprising an open bottom, an upper surface, sidewalls, a cavity at least partially defined by the bottom, the upper surface, and the sidewalls, and a clip extending from the sidewalls.

In some embodiments, a catheter interface protection device comprises a shield comprising an open bottom, an upper surface, sidewalls, and a cavity at least partially defined by the bottom, the upper surface, and the sidewalls, a clip, a tether, and a latch.

The upper surface may be flat. The upper surface may have a surface variation between 100 nm and 500 nm. The upper surface may comprise an opening. The opening may comprise a first arcuate portion and a second arcuate portion.

The first arcuate portion may be configured to hold a first catheter having a first diameter. The second arcuate portion may be configured to hold a second catheter having a second diameter. The first diameter may be different than the second diameter. The opening may comprise a third arcuate portion. The first arcuate portion may be configured to hold a first catheter having a first diameter. The second arcuate portion may be configured to hold a second catheter having a second diameter. The third arcuate portion may be configured to hold a third catheter having a third diameter. The first diameter may be different than the second diameter. The second diameter may be different than the third diameter. The first diameter may be different than the third diameter. The first arcuate portion may comprise a first region, a second region extending from the first region, and a third region extending from the second region. The first region may be configured to hold a first catheter having a first diameter. The second region may be configured to hold a second catheter having a second diameter. The third region may be configured to hold a third catheter having a third diameter. The first diameter may be different than the second diameter. The second diameter may be different than the third diameter. The first diameter may be different than the third diameter.

The second arcuate portion may comprise: a first region, a second region extending from the first region, and a third region extending from the second region. The first region of the second arcuate portion may be configured to hold a fourth catheter having a fourth diameter. The second region of the second arcuate portion may be configured to hold a fifth catheter having a fifth diameter. The third region of the second arcuate portion may be configured to hold a sixth catheter having a sixth diameter. The fourth diameter may be different than the fifth diameter. The fifth diameter may be different than the sixth diameter. The fourth diameter may be different than the sixth diameter.

The opening may comprise a first portion and a second portion. The first portion may be configured to hold a first catheter having a first diameter. The second portion may be configured to hold a second catheter having a second diameter. The first diameter may be different than the second diameter.

The first portion may comprise a first polygonal shape. The second portion may comprise a second polygonal shape. The first polygonal shape may be the same as the second polygonal shape. The first polygonal shape may be different than the second polygonal shape. At least one of the first polygonal shape or the second polygonal shape may comprise a rectangle. At least one of the first polygonal shape or the second polygonal shape may comprise a parallelogram. At least one of the first polygonal shape or the second polygonal shape may comprise a triangle.

The opening may comprise a slit and flashing configured to deform around a catheter.

The opening may be in communication with a slot.

The vent may comprise an uncovered hole. The vent may be an uncovered hole. The vent may be at least partially covered by permeable material. The vent may be covered by permeable material. The sidewalls may comprise the vent. The vent may have an oblong shape having a major axis extending between the upper surface and the bottom. The shield may comprise a plurality of vents including the vent. The plurality of vents may comprise vents having different sizes. The plurality of vents may comprise vents having different major axes. The plurality of vents may comprise vents having different shapes. The shield may further comprise a slot extending from the bottom, along the sidewalls, and into the upper surface. A first set of vents of the plurality of vents on a first side of the slot may mirror a second set of vents of the plurality of vents on a second side of the slot opposite the first side of the slot.

The shield may further comprise a slot extending from the bottom, along the sidewalls, and into the upper surface.

The shield may be configured to surround a catheter interface. The shield may be configured to be spaced from a catheter interface when a catheter interface is in the cavity.

The device may further comprise a first clip. The first clip may extend outward from the sidewalls. The first clip may comprise an undercut. The undercut may comprise a top undercut on an upper side of the first clip. The top undercut may be configured to accommodate a portion of a latch. The top undercut may be configured to accommodate a portion of a catheter. The undercut may comprise a bottom undercut on a bottom side of the first clip. The bottom undercut may be configured to accommodate a portion of a catheter. The bottom undercut may be configured to accommodate a plurality of portions of a catheter. The bottom undercut may be configured to accommodate portion of a plurality of catheters. The undercut may comprise a side undercut on a lateral side of the first clip. The first clip may be free of an undercut on lateral sides of the first clip. The device may comprise a plurality of clips including the first clip. The plurality of clips may include a second clip having the same features as the first clip. The device may further comprise a first flange. The first clip may be circumferentially offset from the flange.

The device may further comprise a first latch, and a first tether connecting the latch to the shield. The first latch may comprise a gripping feature. The gripping feature may comprise a plurality of protrusions. The gripping feature may comprise a groove. The gripping feature may comprise a roughened surface. The first latch may comprise vascular indicia. The vascular indicia may comprise a letter. The letter may comprise A or V.

The device may further comprise a first flange. The first latch may be circumferentially offset from the flange. The first tether may extend outward from the sidewalls. The first tether may comprise a thickness between 0.5 mm and 3 mm. The first tether may comprise a width between 0.5 mm and 3 mm. The first tether may comprise a thickness greater than a width. The first tether may comprise a textured surface. The sidewalls may comprise a textured surface proximate the first tether. The device may comprise a plurality of tethers including the first tether. The plurality of tethers may include a second tether. The first tether may be connected to a first side of the latch at a first connection point. The second tether may be connected to a second side of the latch at a second connection point. The latch may comprise a tab between the first connection point and the second connection point.

The device may further comprise a first flange. The first flange may extend outward from the sidewalls. The first flange may comprise a flat bottom surface, and an arcuate upper surface. The first flange may comprise a textured surface. The first flange may comprise an anchor. The anchor may extend upward from an edge of the first flange. The may further comprise a second flange. The second flange may have the same features as the first flange. The second flange may extend laterally opposite the first flange. The first flange and the second flange may comprise a flexible material configured to allow the first flange and the second flange to be wrapped around a user. The first flange may be configured to be coupled to the second flange.

The device may be monolithically formed. The device may comprise silicone. The device may consist essentially of silicone.

In some embodiments, a catheter interface protection device comprises a shield comprising an open bottom, a flat upper surface, sidewalls, and a cavity at least partially defined by the bottom, the upper surface, and the sidewalls.

The device may further comprise a vent. The upper surface may comprise the vent. The shield may further comprise an opening. The device may further comprise a strap including a fastener configured to fit into the opening. The strap may comprise a width greater than a thickness. The strap may comprise a textured surface. The device may further comprise a flange. The strap may be circumferentially offset from the flange. The strap may be at least partially circumferentially overlaps the flange. The device may further comprise a flange. The device may further comprise a slot extending from the bottom, along the sidewalls, and into the upper surface. The upper surface may comprise an opening. The device may further comprise a clip. The clip may comprise an undercut on a bottom side of the clip.

In some embodiments, a kit comprises a catheter interface protection device, and tape.

The tape may comprise a first piece having a first indicia. The tape may comprise a second piece having a second indicia. The second indicia may be different than the first indicia. The first indicia may comprise a first letter. The second indicia may comprise a second letter. The second letter may be different than the first letter. The first letter may be A. The second letter may be V. The first indicia may comprise a first color. The second indicia may comprise a second color. The second color may be different than the first letter. The first color may be red. The second color may be blue. The first indicia may comprise a first letter and the second indicia may comprise a second letter different than the first letter.

The tape may comprise a writable surface. The kit may further comprise hydrocolloid adhesive. The kit may further comprise a permeable strip. The kit may be sterile.

In some embodiments, a kit comprises a catheter interface protection device, and hydrocolloid adhesive. The kit may be sterile.

In some embodiments, a kit comprises a catheter interface protection device, and a base structure configured to be coupled to the device. The base structure may comprise an adhesive bottom surface. The base structure may comprise a first lip configured to engage a first edge of the device. The base structure may comprise a second lip configured to engage a second edge of the device. The second edge may be opposite the first edge.

The kit may comprise a card. The card may comprise a tab extending over a portion of the device. Adhesive components of the kit may be adherable to and removable from the card for use without removal of an adhesive backing.

The kit may comprising a tray including a plurality of wells.

The kit may be sterile.

In some embodiments, a non-therapeutic method of protecting a catheter interface comprises extending a catheter in a subject through a slot in a catheter interface protection device, wrapping the catheter at least partially around a clip of the catheter interface protection device, and securing a latch of the catheter interface protection device around the clip.

The method may comprise positioning a distal portion of the catheter in a cavity of the catheter interface protection device, wherein a proximal portion of the catheter extends through an opening of the catheter interface protection device. The method may comprise changing a direction of the catheter at least twice between the catheter interface and a proximal end of the catheter. Wrapping the catheter at least partially around the clip may comprise wrapping the catheter under a portion of the clip. Wrapping the catheter at least partially around the clip may comprise wrapping the catheter at least once around the clip. Wrapping the catheter at least partially around the clip may comprise wrapping the catheter under a portion of the clip and under a portion of a second clip of the catheter interface protection device.

The method may further comprise extending a second catheter in the subject through the slot, wrapping the second catheter at least partially around at least one of the clip or a second clip of the catheter interface protection device, securing at least one of the latch around the clip the latch or a second latch of the catheter interface protection device around the second clip of the catheter interface protection device.

Wrapping the catheter at least partially around the clip may comprise wrapping the catheter under a portion of the clip, and wherein wrapping the second catheter at least partially around at least one of the clip or a second clip of the catheter interface protection device may comprise wrapping the catheter under a portion of the second clip. Wrapping under the portion of the clip may be in a first direction, and wherein wrapping the second catheter under the portion of the second clip may be in a second direction opposite the first direction. Wrapping the catheter at least partially around the clip may comprise wrapping the catheter under a portion of the clip, and wherein wrapping the second catheter at least partially around at least one of the clip or a second clip of the catheter interface protection device may comprise wrapping the catheter under a portion of the clip. Wrapping the catheter at least partially around the clip may comprise wrapping the catheter under a portion of the clip and the second clip, and wherein wrapping the second catheter at least partially around at least one of the clip or a second clip of the catheter interface protection device may comprise wrapping the catheter under a portion of the clip and the second clip.

In some embodiments, a device for positioning a subject in a prone position comprises a padded area comprising an opening configured to accommodate a catheter interface protection device.

The opening may have a depth between 1 cm and 10 cm. The opening may have a lateral dimension between 1 cm and 10 cm. The padded area may further comprise a channel configured to route a catheter between the opening and an edge of the padded area. The device may further comprise another padded area coupled to the padded area. The another padded area may be configured to accommodate at least one of a head or a torso of a subject.

In some embodiments, a device for testing a catheter interface protection device comprises a base configured to be coupled to a catheter interface protection device, and a plurality of ports at different angles around the base.

The device may further comprise a force gauge configured to be coupled to a catheter. The plurality of ports extend 180° around the base. The plurality of ports extend greater than 180° around the base. The plurality of ports extend less than 180° around the base. The base may comprise a flat surface. The base may comprise a concave surface. The base may comprise a convex surface. The device may further comprise a chamber around the base and the plurality of ports. The chamber may be configured to control a relative humidity of the device. The chamber may be configured to control a temperature of the device. The device may further comprise a fluid flow testing device.

In some embodiments, a catheter interface protection device comprises a shield. The shield comprises an open bottom, an upper surface, sidewalls, a plurality of vents in the sidewalls, and a cavity partially defined by the bottom, the upper surface, and the sidewalls, and a slot extending from the bottom along the sidewalls to the opening. The upper surface is flat. The upper surface is transparent. The upper surface comprises an opening. The opening comprises a first arcuate or polygonal portion. The upper surface comprises a second arcuate or polygonal portion. Each of the plurality of vents has an oblong shape with a major axis extending between the upper surface and the bottom. Each of the plurality of vents is an uncovered hole. The shield is configured to surround and be spaced from a catheter interface when a catheter interface is in the cavity. The device further comprises a first clip extending outward from the shield, a first latch, a first tether connecting the first latch to the shield, a second clip extending outward from the shield, a second latch, a second tether connecting the second latch to the shield, a first flange extending outward from the shield, and a second flange extending outward from the shield laterally opposite the first flange. The first flange comprises a flat lower surface, an arcuate upper surface and, an anchor extending upward from an edge of the first flange. The second flange comprises a flat lower surface, an arcuate upper surface, and an anchor an anchor extending upward from an edge of the second flange. The device comprises silicone. The device is monolithically formed.

In some embodiments, a catheter interface protection device comprises, or alternatively consists essentially of, a shield, a first clip extending outward from the shield, a first latch, a first tether connecting the first latch to the shield, a first flange extending outward from the shield, and a second flange extending outward from the shield laterally opposite the first flange. The first flange may comprise a flat lower surface, an arcuate upper surface, and an anchor extending upward from an edge of the first flange. The second flange may comprise a flat lower surface, an arcuate upper surface, and an anchor an anchor extending upward from an edge of the second flange. The shield may comprise an open bottom, an upper surface, sidewalls, a plurality of vents in the sidewalls, a cavity at least partially defined by the bottom, the upper surface, and the sidewalls, and a slot extending from the bottom along the sidewalls to the opening. The upper surface may be flat and/or transparent. The upper surface may comprise an opening. The opening may comprise a first arcuate or polygonal portion. Each of the plurality of vents may have an oblong shape with a major axis extending between the upper surface and the bottom. Each of the plurality of vents may be an uncovered hole. The shield may be configured to surround and be spaced from a catheter interface when a catheter interface is in the cavity.

The device may further comprise a second clip extending outward from the shield, a second latch, and a second tether connecting the second latch to the shield. The upper surface may have a surface variation between 100 nm and 500 nm. The opening may further comprise a second arcuate or polygonal portion. The device may comprise silicone. The device may be monolithically formed. The opening may comprise a slit and flashing configured to deform around a catheter. The first tether may comprise a thickness greater than a width. The first tether may comprise a textured surface. The sidewalls may comprise a textured surface proximate the first tether.

In some embodiments, a catheter interface protection device comprises, or alternatively consists essentially of, a shield, a first clip extending outward from the shield, a first latch, and a first tether connecting the first latch to the shield. The shield may comprise an open bottom, an upper surface, sidewalls, a plurality of vents in the sidewalls, a cavity at least partially defined by the bottom, the upper surface, and the sidewalls, and a slot extending from the bottom along the sidewalls to the opening. The upper surface may comprise an opening. The opening may comprise a first arcuate or polygonal portion. The shield may be configured to surround and be spaced from a catheter interface when a catheter interface is in the cavity.

The device may further comprise a second clip extending outward from the shield, a second latch, and a second tether connecting the second latch to the shield. The device may further comprise a first flange extending outward from the shield. The first flange may comprise a flat lower surface and an arcuate upper surface. The first flange may comprise an anchor extending upward from an edge of the first flange. The upper surface may be flat. The upper surface may have a surface variation between 100 nm and 500 nm. The upper surface may be transparent. Each of the plurality of vents may have an oblong shape with a major axis extending between the upper surface and the bottom. Each of the plurality of vents may be an uncovered hole. The device may comprise silicone. The device may be monolithically formed.

The inventors have invented a new, original, and ornamental design for a catheter securing system of which the following is the specification, reference being had to the accompanying drawings, forming a part hereof. In some embodiments, what is claimed is the ornamental design for a catheter securing system, as shown and described (e.g., with respect to FIGS. 29A-29H). Broken line portions and/or solid lines that may be converted into broken line portions show unclaimed subject matter only and would form no part of the claimed design.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only examples and are therefore not to be considered limiting in the scope of the claims.

FIG. 3A illustrates a catheter seal.

FIG. 3B illustrates the catheter seal of FIG. 3A, with two umbilical catheters placed between two seal portions.

FIG. 4 illustrates a base of a shield.

FIG. 5 illustrates a method of using the device of FIG. 1.

FIG. 9A illustrates a perspective view of another device for protecting an umbilical stump-catheter interface.

FIG. 9B illustrates a side view of the device of FIG. 9A, particularly showing the device being used with a catheter.

FIG. 9C illustrates a top view of the device of FIG. 9A.

FIG. 10A illustrates a perspective view of another device for protecting an umbilical stump-catheter interface, particularly showing the device being used with a catheter.

FIG. 10B illustrates a side view of the device of FIG. 10A.

FIG. 10C illustrates a top view of the device of FIG. 10A.

FIG. 11A illustrates a perspective view of another device for protecting an umbilical stump-catheter interface, particularly showing the device being used with a catheter.

FIG. 11B illustrates a side view of the device of FIG. 11A.

FIG. 11C illustrates a top view of the device of FIG. 11A.

FIG. 20Ai is a top, front, and side view of an example device for protecting a catheter interface.

FIG. 20Aii is another top, front, and side view of the device of FIG. 20Ai.

FIG. 20Aiii is yet another top, front, and side view of the device of FIG. 20Ai.

FIG. 20Bi is top view of the device of FIG. 20Ai.

FIG. 20Bii is another top view of the device of FIG. 20Ai.

FIG. 20Ci is an expanded top view of the device of FIG. 20Ai in the area of the circle 20Ci of FIG. 20Bii.

FIGS. 20Cii-20Cviii are example expanded top views of a device for protecting a catheter interface.

FIG. 20D is a top and back view of the device of FIG. 20Ai.

FIG. 20E is a front view of the device of FIG. 20Ai.

FIG. 20Fi is a side view of the device of FIG. 20Ai.

FIG. 20Fii is an expanded side view of the device of FIG. 20Ai in the area of the circle 20Fii of FIG. 20Fi.

FIG. 20Fiii is a cross-sectional view of the device of FIG. 20Ai taken along the line 20Fiii-20Fiii of FIG. 20D.

FIGS. 20Fiv and 20Fv schematically illustrate a cross-sectional side views of tape interacting with a flange.

FIG. 20G is a top view of an example implementation of the device of FIG. 20Ai.

FIG. 20Hi is an expanded top view of the device of FIG. 20Ai in the area of the circle 20Hi of FIG. 20Bii.

FIG. 20Hii is a cross-sectional view of the device of FIG. 20Ai along the line 20Hii-20Hii in FIG. 20Bii.

FIG. 20Hiii is an expanded cross-sectional view of the device of FIG. 20Ai in the area of the circle 20Hiii of FIG. 20Hii.

FIGS. 22A-22M illustrate example interactions between the device of FIG. 20Ai and one or more catheters.

FIG. 28Bi is a top and side view of another example testing apparatus for a device for protecting a catheter interface.

FIG. 28Bii is an expanded top view of a portion of the testing apparatus of FIG. 28Bi.

FIG. 28C is a top and front view of yet another example testing apparatus for a device for protecting a catheter interface.

DETAILED DESCRIPTION

Figure 1:
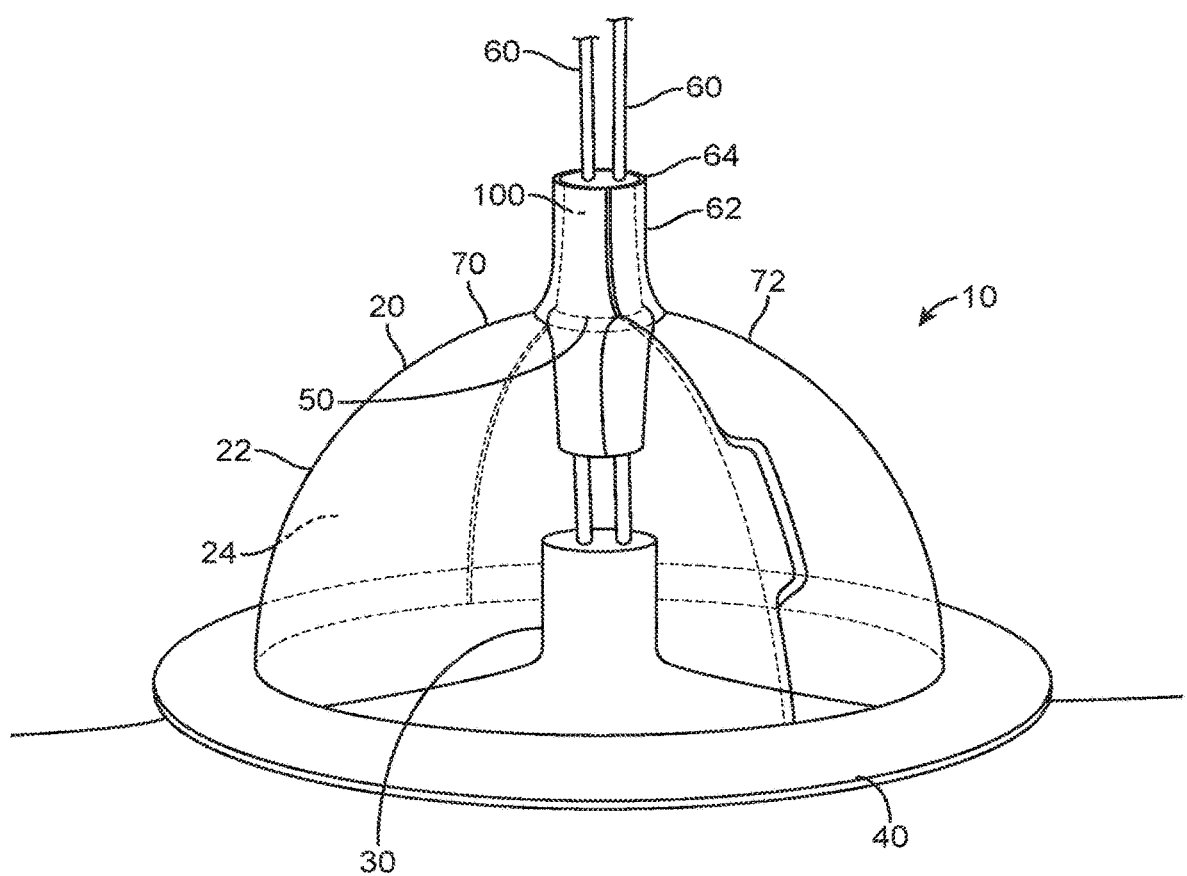
FIG. 1 illustrates device for protecting an umbilical stump-catheter interface.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

In at least one embodiment, a device for protecting an umbilical stump is provided. The device may be used to protect an umbilical stump after umbilical catheterization. The device may also be used to secure, and optionally seal against, the umbilical catheter in order to reduce the risk of a central-line associated bloodstream infection. In one implementation, the device is a rigid, plastic device that covers and isolates a small area around the umbilical catheter insertion site from the surrounding environment, and effectively halts bacterial migration to this area. The device also has an adhesive seal at the base of the device for inhibiting or preventing migration of bacteria from the skin into the stump.

FIG. 1 illustrates a device 10 for protecting an umbilical stump-catheter interface. The device 10 has a shield 20 with a wall 22 that defines a cavity 24 for accommodating an umbilical stump 30. As shown in the figure, the shield 20 further includes a base 40 for attachment to a patient (e.g., a neonate). The device 10 also has an opening 50 at the shield 20 for allowing one or more umbilical catheter(s) 60 to extend therethrough.

In the illustrated embodiments, at least a part of the shield 20 has a dome shape. In particular, the bottom portion of the shield 20 has a dome shape, while a top portion of the shield 20 has a tubular structure 62. In other embodiments, the tubular structure 62 may be considered to be a separate component from the shield 20 (regardless of whether they are formed together or separately attached to each other). In such cases, the entirety of the shield 20 may be considered as having a dome shape. As shown in the figure, the tubular structure 62 extends from the dome shape shield 20, and has a channel 64 that extends from the opening 50. The tubular structure 62 is at a top of the dome shape shield 20. In other embodiments, the tubular structure 62 may be extending from the dome shape shield 20 at other locations of the dome shape shield 20.

In other embodiments, the shield 20 may not have a dome shape. For example, in other embodiments, the shield 20 may have a rectangular box shape, a square box shape, a pyramid shape, a cylindrical shape, or any of other shapes.

Also, in other embodiments, the tubular structure 62 may not extend outward from the shield 20. For example, in other embodiments, the tubular structure 62 (or at least a part of it) may extend inward into the cavity 24 defined by the shield 20.

In the illustrated embodiments, the shield 20 has a first shield portion 70 and a second shield portion 72 that is moveably coupled to the first shield portion 70. When the second shield portion 72 is in a first position, the umbilical stump 30 is shielded by the shield 20 (see FIGS. 1 and 2B), and when the second shield portion 72 is in a second position, the umbilical stump 30 is exposed to an environment outside the shield 20 (see FIG. 2A).

In the illustrated embodiments, the first shield portion 70 of the shield 20 is rigid, and the second shield portion 72 of the shield 20 is also rigid. In other embodiments, a part of the shield 20 may be flexible. For example, in other embodiments, the base 40 of the shield 20 may be flexible. In some cases, the base 40 may be made from a polymer or a plastic. Also, in some embodiments, a majority of the shield 20 is rigid. Furthermore, in some embodiments, the base 40 may be made from a material that is more flexible compared to the shield 20. A flexible base 40 has the advantage of allowing the base to conform with a surface profile of a skin of the patient. In addition, in the illustrated embodiments, at least a part of the shield 20 is transparent. This feature allows a physician or a nurse to see the condition of the umbilical stump 30, the stump-catheter interface, the catheter coming out from the stump 30, position of catheter, and catheter marking (if any).

Figure 2A:
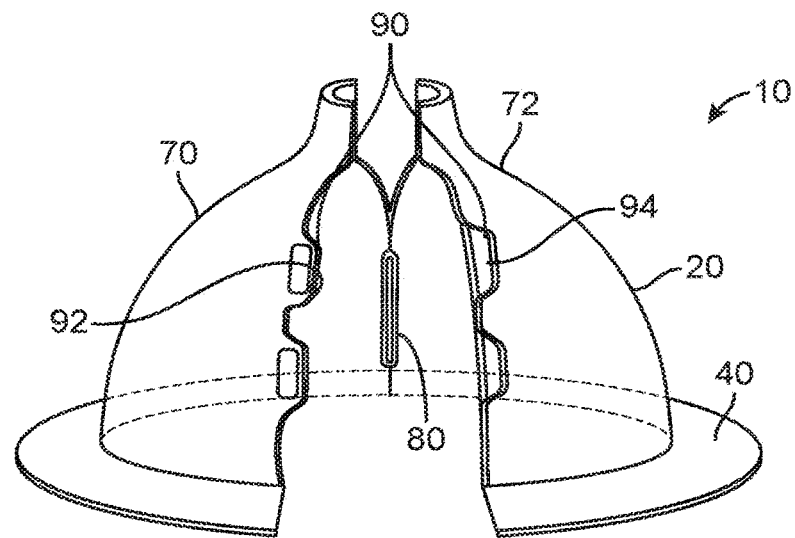
FIGS. 2A-2B illustrate a shield of the device of FIG. 1, particular showing the shield having an open-configuration and a closed-configuration.
Figure 2B:
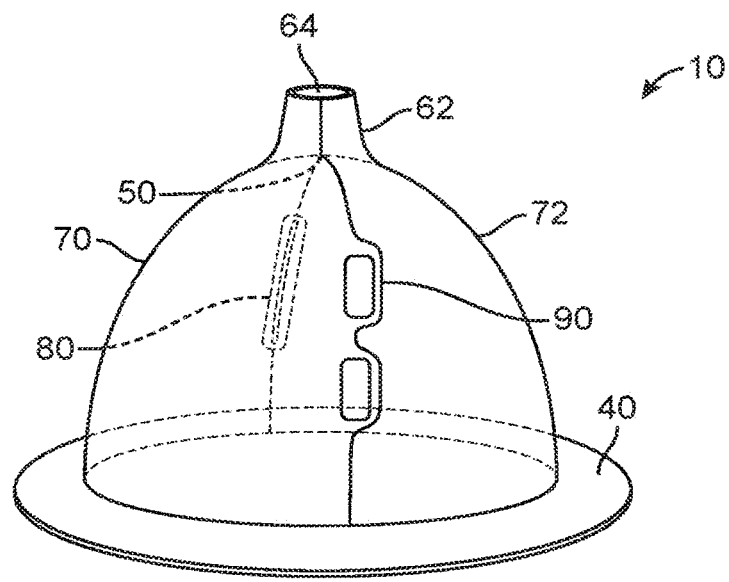

Also, as shown in FIGS. 2A-2B, the device 10 has a mechanical hinge 80 for rotatably coupling the second shield portion 72 to the first shield portion 70. In some cases, the hinge 80 may be implemented using a connection rod. In other embodiments, the hinge 80 may be implemented using a flexible plastic that is connected between the first shield portion 70 and the second shield portion 72. The hinge 80 may be a double-action hinge, a live hinge, etc. The second shield portion 72 is moveable relative to the first shield portion 70 in a path that is parallel to a plane of the base 40.

In other embodiments, the second shield portion 72 may be moveable relative to the first shield portion 70 in a path that is non-parallel to a plane of the base 40.

Also, in the illustrated embodiments, the device 10 further includes a securing device 90 for locking the second shield portion 72 relative to the first shield portion 70 when the second shield portion 72 is in the first position. In some cases, the securing device 90 may be a snap-fit connector. For example, the first shield portion 70 may have one or more loops 92, and the second shield portion 72 may have one or more corresponding anchors 94 for snap-fit into the respective loop(s) 92. With this configuration, the first and second shield portions 70, 72 can snap close, and may be pulled open relative to each other by applying a small push at the area next to the anchor(s). In other embodiments, the securing device 90 may be any of other types of connection mechanism, such as a Velcro, an interference-fit connector, a button, etc.

As shown in FIGS. 1, 3A, and 3B, the device 10 also includes a seal 100 located at or adjacent the opening 50 (note that the seal 100 is not shown in FIGS. 2A-2B for clarity). In particular, as shown in FIG. 3A, the seal 100 is located within the channel 64 in the tubular structure 62. The seal 100 has a first seal portion 102 that is coupled to the first shield portion 70 (or to a first part of the tubular structure 62), and a second seal portion 104 that is coupled to the second shield portion 72 (or to a second part of the tubular structure 62). The first seal portion 102 and the second seal portion 104 are configured to cooperate with each other for securing the umbilical catheter 60 relative to the device 10. In particular, the seal 100 is configured for mechanically holding the umbilical catheter 60 in a vertical position like that shown in FIG. 3B. In other embodiments, the seal 100 may be configured to hold the umbilical catheter 60 at other orientations relative to the patient. For example, in other embodiments, the tubular structure 62 with the seal 100 may be oriented horizontally or at an acute angle relative to a vertical axis.

In some embodiments, the material and/or the size and shape of the seal 100 can be selected so that the resulting seal 100 can provide a desired frictional force that impedes catheter movement relative to the seal 100, while providing a compliance that does not collapse or over-compress the catheter (to impede fluid flow). Accordingly, in some embodiments, the closing of the seal portions 102, 104 functions to secure the catheter relative to the seal 100. Also, in some cases, the longitudinal dimension of the seal (e.g., along the direction of the catheter) can be increased to further improve contact area between the seal 100 and the catheter.

As discussed, the seal 100 may be at or adjacent the opening 50. In some cases, the seal 100 may be considered as being "at" the opening 50 if any part of the seal 100 intersects a cross section of the opening 50. Also, in some cases, no part of the seal 100 intersects a cross section of the opening 50. In such cases, the seal 100 may be considered to be "adjacent" the opening 50 if a spacing between the seal 100 and the opening 50 (measured along a longitudinal axis of the tubular structure 62) is less than 3 cm, and more preferably less than 1 cm.

In one implementation, the first seal portion 102 and the second seal portion 104 may be made from rubber (e.g., neoprene rubber). The first seal portion 102 and the second seal portion 104 may have a shore hardness of 70 that allows the seal portions 102, 104 to deform around the catheter(s) 60. This secures the catheter(s) 60 without occluding them due to compression by the seal portions 102, 104. In other embodiments, the seal portions 102, 104 may have other hardness. As shown in FIG. 3A, before the seal portions 102, 104 are used to clamp around the catheter(s) 60, the seal portions 102, 104 have respective surfaces that face towards each other, wherein the surfaces are planar. When one or more catheter(s) 60 are placed between the seal portions 102, 104, and when the seal portions 102, 104 are used to grip around the catheter(s) 60, the opposing surfaces of the seal portions 102, 104 deform around the catheter(s) 60 (see FIG. 3B). Such configuration is advantageous because it allows the seal 100 to form a physical barrier to inhibit or prevent bacteria from outside the device 10 to travel into the cavity 24. Such configuration is also advantageous because it allows the seal 100 to stabilize different sized catheters. In other embodiments, instead of the opposing planar surfaces that deform in response to placement of the catheter(s) there between, the seal portions 102, 104 may have one or more pre-formed channels for accommodating respective catheter(s) 60.

Also, in some embodiments, the seal portions 102, 104 may have a sufficiently high friction that allows the seal portions 102, 104 to inhibit or prevent movement of the catheter(s) 60 when the seal portions 102, 104 are closed around the catheter(s) 60. In some cases, the friction may be sufficient to inhibit or prevent self-movement between the catheter(s) 60 and the seal 100, while allowing a physician to manually slide the seal 100 relative to the catheter(s) 60. In other embodiments, the friction may be sufficiently high to inhibit or prevent a physician from manually sliding the seal 100 relative to the catheter(s) 60.

In the illustrated embodiments, the seal 100 is configured to protect the umbilical stump 30 from bacteria associated with the umbilical catheter 60, while the shield 20 is configured to protect the umbilical stump 30 from bacteria from environment outside the shield 20.

As shown in FIG. 4, the device 10 also includes an adhesive 142 at the base 40 for attaching the base 40 to the patient. In one implementation, the adhesive 142 may be a double-sided tape, with a first side attached to a bottom surface of the base 40, and a second side (opposite from the first side) facing downward. The first and second sides of the adhesive 142 may be the same type of adhesive or different types of adhesive. The adhesive 142 may comprise multiple layers of single-sided or double-sided tape. The adhesion strength between the first side of adhesive 142 and the bottom surface of the base 40 may be higher than the adhesion strength between the second side of adhesive 142 and the skin, such that removal of device 10 from skin occurs before and/or without removal of adhesive 142 from the base 40. The first side of adhesive 142 that is attached to the bottom surface of the base 40 may be acrylic-based, silicone-based, synthetic rubber-based, etc. The device 10 may also include a tape cover 144 covering the second side of the adhesive 142. Since a neonate's skin is particularly sensitive to irritation and damage, the strength and chemical composition of the second side of adhesive 142 that is covered by the tape cover 144 may be designed to protect the neonate's skin. In one implementation, a hydrocolloid gel may be used to implement adhesive 142. Such an adhesive may have minimal skin irritation over a long period of time. In another implementation, the adhesive 142 may be a silicone-based adhesive. Such an adhesive may improve adherence to neonatal skin and reduce patient discomfort upon removal.

FIG. 5 illustrates a method of using the device 10. First, the device 10 is provided. As discussed, the device 10 includes a shield 20 with a wall 22 that defines a cavity 24 for accommodating an umbilical stump 30, wherein the shield 20 further includes a base 40 for attachment to a patient. In some embodiments, the act of providing the device 10 may be performed by a manufacturer of the device 10. In other embodiments, the act of providing the device 10 may be performed by an importer of the device 10. In further embodiments, the act of providing the device 10 may be performed by a distributer, a hospital, a physician, or a nurse.

Before the device 10 is used to shield the umbilical stump 30, the adhesive tape 144 is removed from the adhesive 142 (see FIG. 4). After the bottom surface of the adhesive 142 is exposed, the shield 20 is then placed over the umbilical stump 30, and the base 40 of the shield 20 is then attached to the patient using the adhesive 142. In some embodiments, as the base 40 is being attached to the patient, the first shield portion 70 and the second shield portion 72 are closed relative to each other, thereby closing the first and second seal portions 102, 104 towards the umbilical catheter 60. In other embodiments, the first shield portion 70 and the second shield portion 72 may be closed relative to each other first, to thereby close the seal portions 102, 104 to grip the umbilical catheter 60. The shield 20 is then moved down towards the patient's skin to secure the base 40 on the patient's skin. As the shield 20 is moved down, the seal portions 102, 104 surrounding the umbilical catheter 60 slide relative to the umbilical catheter 60 while the umbilical catheter 60 is confined within the space defined between the seal portions 102, 104.

In the illustrated embodiments, the opening 50 at the shield 20 allows the umbilical catheter 60 to extend through the shield 20 while the umbilical catheter 60 is gripped between the seal portions 102, 104. Accordingly, the opening 50 at the shield 20 accommodates the umbilical catheter 60.

After the shield 20 is placed around the umbilical stump 30, the umbilical stump 30 is then shielded from an environment using the shield 20. The seal 100 formed by the seal portions 102, 104 also protects the umbilical stump 30 from bacterial associated with the umbilical catheter 60. In addition, the adhesive 142 at the base 40 inhibits or prevents bacteria at the skin outside the shield 20 from reaching the umbilical stump 30.

As shown in the above embodiments, the device 10 is advantageous because (1) it isolates the area around the catheter insertion site from surrounding environment to inhibit or prevent or at least reduce bacterial migration to this area from the air, (2) its adhesive 142 below the base 40 functions as a seal that inhibits or prevents or at least reduce migration of bacteria from the skin into the umbilical stump and attaches the device 10 to the skin, and (3) the seal 100 secures the catheter(s) 60 relative to the shield 20 and inhibits or prevents or at least reduce bacterial migration from the catheter(s) 60 into the umbilical stump. These benefits would lead to a reduction in neonate morbidity and mortality, would increase the ease of neonate care in the NICU, and may reduce cost of care. Also, the device 10 is advantageous because it does not interfere with current umbilical catheterization procedures. This allows the integration of the device 10 into current practice easy. The device 10 is also easy to use.

Figure 6:
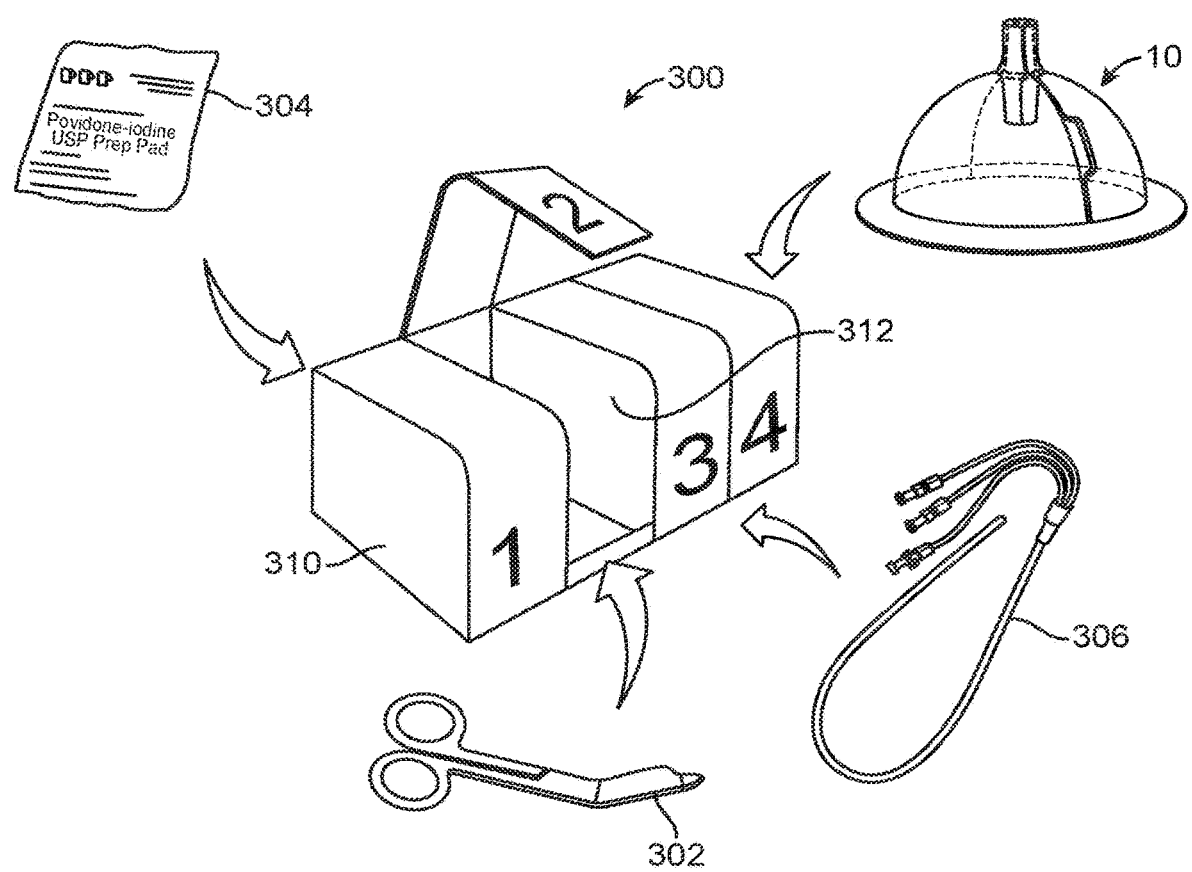
FIG. 6 illustrates a kit that includes the device of FIG. 1.

In one or more embodiments described herein, the device 10 for protecting the umbilical stump-catheter interface may be a part of a kit. FIG. 6 illustrates a kit 300 that includes the device 10. In the illustrated embodiments, the kit 300 also includes a scissor 302, one or more sterilization material(s) 304, and one or more umbilical catheters 306. By means of non-limiting examples, a sterilization material may be chlorhexidine, betadine, etc. The kit 300 also includes a container 310 having a plurality of compartments 312 for housing the device 10, the scissor 302, the one or more sterilization materials 304, and the one or more umbilical catheters 306, respectively. It should be noted that the kit 300 is not limited to the configuration shown, and that the kit 300 may have other configurations in other embodiments. For example, in other embodiments, instead of having all of the items shown, the kit 300 may include the device 10, and one or a combination of: a scissor, a sterilization material, and an umbilical catheter. In other embodiments, instead of only having the items aforementioned, the kit 300 may include additional materials. The kit 300 may include adhesives to be used in conjunction with the device 10. The adhesives can be used for one or various functions, for example protecting the skin from irritation or abrasion, attaching the device 10 to the skin, attaching the device 10 to the backing of another adhesive, as labels to distinguish between different catheter types, and/or others. The adhesives may be packaged together, but separate from the device 10, or as part of the same packaging as the device 10. The kit 300 is advantageous because it provides an integrated solution. In particular, the kit 300 may include tools that are involved in the placement of umbilical catheter, and also the device 10 for protecting the umbilical stump 30. During use, the physician or nurse can use the sterilization material 304 in the kit 300 for disinfection of a treatment site. After the treatment site at the patient has been disinfected, the physician or nurse can then apply the umbilical catheter 306 in the kit 300 on the patient. If any cutting is needed in the process, the physician or nurse can also use the scissor 302 in the kit 300. Furthermore, the physician or nurse can use the device 10 in the kit 300 to shield and protect the umbilical stump against bacterial infection associated with the catheter and/or the environment surrounding the patient (e.g., by inhibiting or preventing the umbilical stump from being in physical contact with objects and/or substances outside the shield).

It should be noted that the kit 300 is not limited to having the above items, and that the kit 300 may include other items in other embodiments. For example, in other embodiments, in addition to including the device 10, the kit 300 may include one or a combination of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad. Also, the container 310 of the kit 300 may have a compartment for housing the device 10, and one or more additional compartment(s) for housing one or a combination of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad.

Figure 7:
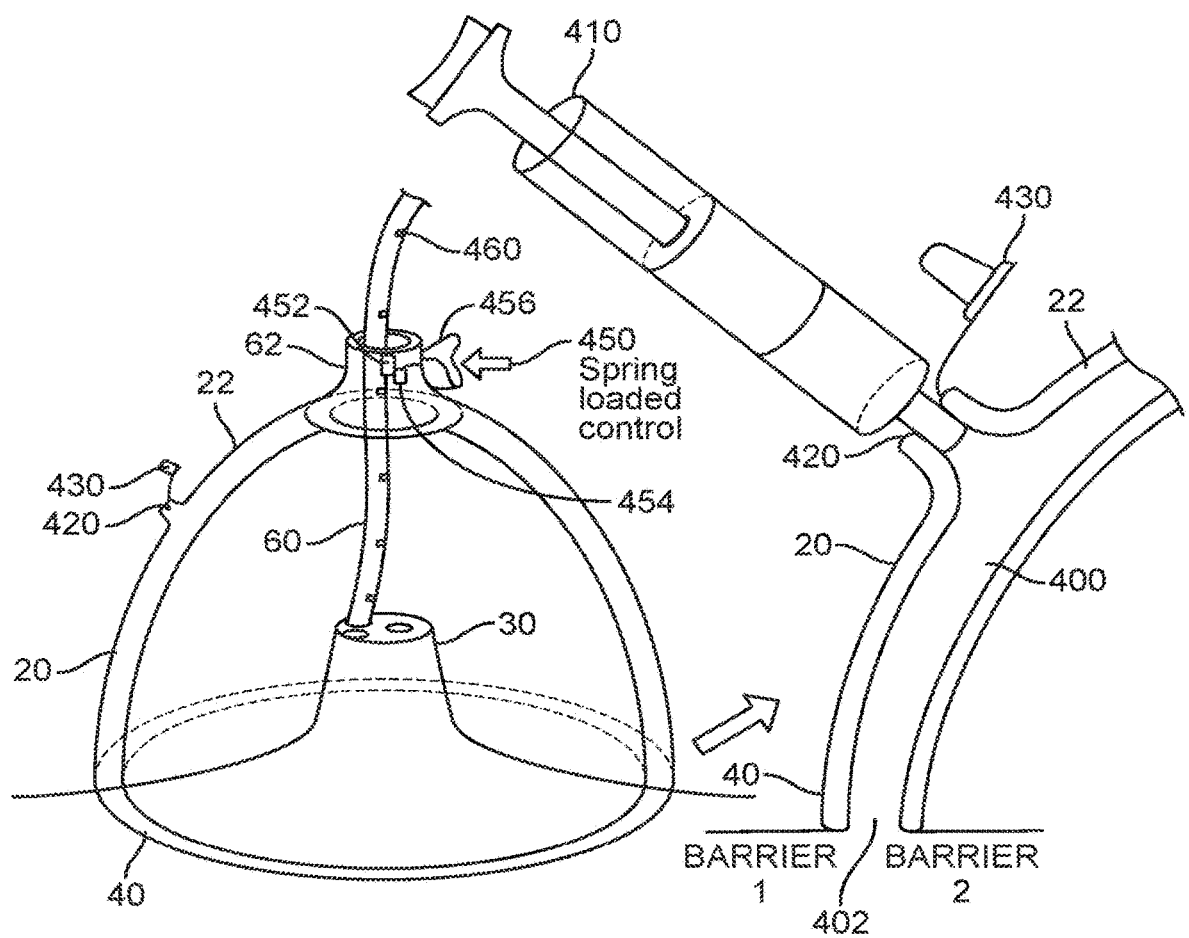
FIG. 7 illustrates another device for protecting an umbilical stump-catheter interface.

It should be noted that the device 10 should not be limited to the examples described above, and that the device 10 may have other configurations in other embodiments. For example, as shown in FIG. 7, in other embodiments, instead of, or in addition to, using the adhesive 142, the shield 20 of the device 10 may include a channel 400 within the wall 22 of the shield 20. The channel 400 may be defined by the wall 22 of the shield 20. Alternatively, the channel 400 may be in a separate tube that is located inside the wall of the shield 20. The channel 400 is in fluid communication with opening(s) or slot(s) 402 at the bottom (base 40) of the shield 20 where the shield 20 interfaces with the skin of the patient. During use, a syringe 410 may be coupled to an opening 420 at the wall 22 of the shield 20, and the syringe 410 may then be used to apply suction inside the channel 400. The suction causes the patient's skin to be pulled towards the opening(s) or slot(s) 402 at the bottom of the shield 20, thereby securing the skin relative to the shield 20. After sufficient suction has been applied, a cover 430 may then be used to cover up the opening 420.

In some cases, the opening 420 may include a one-way valve. This allows the syringe 410 to remove air within the channel 400 in one direction to create suction within the channel 400, and after the syringe 410 is removed from the opening 420, air will not leak back into the channel 400. If the device 10 is to be decoupled from the patient, the device 10 may be pulled away from the skin, or the patient skin next to the base 40 may be pressed, thereby allowing air to leak back into the channel 400. In further embodiments, a pin or a rod may be inserted into the one-way valve in the opening 420 to open up the valve, thereby allowing air to leak back into the channel 400 to remove the suction.

Also, in one or more embodiments described herein, instead of using the seal 100, the device 10 may include a spring-loaded device 450 (like that shown in FIG. 7) at the tubular structure 62, for securing the catheter 60 relative to the device 10. The spring-loaded device 450 may include an engagement member 452 located inside the channel 64 of the tubular structure 62, and a spring 454 for biasing the engagement member 452 to push the engagement member 452 into the channel 64 inside the tubular structure 62. When the catheter 60 is placed inside the channel 64, the user may pull the tap 456 at the spring-loaded device 450 to allow the catheter 60 to be inserted into the channel 64. When the catheter 60 is desirably positioned relative to the tubular structure 62, the tap 456 may then be released to allow the engagement member 452 to be pushed by the spring 454 towards the catheter 60 to thereby secure the catheter 60 in place. In some cases, the engagement member 452 may be a pin, and the catheter 60 may have multiple openings/indentations 460, wherein the pin may be selectively placed into a one of the openings/indentations 460. In other embodiments, the catheter 60 may have a smooth surface, and the engagement member 452 may be configured to secure the catheter 60 by friction.

Figure 8A:
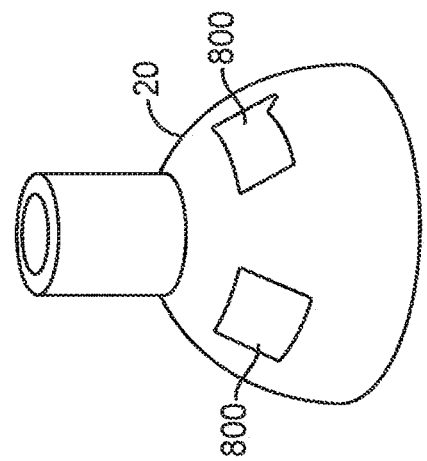
FIGS. 8A-8C illustrate different shields in different embodiments.

In one or more embodiments described herein the shield 20 may optionally further include one or more vents. FIG. 8A illustrates an embodiment of the shield 20, particularly showing the shield 20 having multiple vents 800. The vents 800 may be advantageous in that they may inhibit or prevent a "bio-dome" like effect (which may cause an increase of bacterial load) within the cavity of the shield 20. Also, the vent(s) 800 may allow umbilical stump to dry and inhibit or prevent further bacterial growth. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800. Also, in some embodiments, the shield 20 may include vents with different sizes, or vents with the same size. In further embodiments, the vents may include respective covers that may be selectively opened or closed, thereby allowing a user to selectively choose to allow more air flow or air exchange across the shield 20. Each cover may be in a form of a door that is rotatably coupled to the shield 20 that can be opened or closed to shut the vent. Alternatively, each cover may be in a form of a tape, that may be selectively peeled off by the user to open the vent.

Figure 8B:
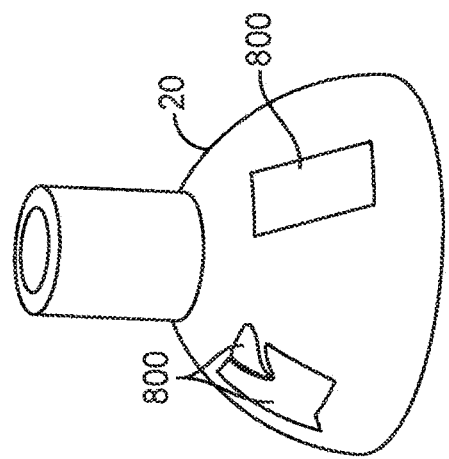

Also, in other embodiments, the vents 800 at the shield 20 may be larger than those show in FIG. 8A. For example, as shown in FIG. 8B, in other embodiments, the shield 20 may have relatively larger vents 800.

In addition, in the illustrated embodiments, the vents 800 at the shield 20 all have the same size. In other embodiments, at least two of the vents 800 at the shield 20 may be in different sizes.

Figure 8C:
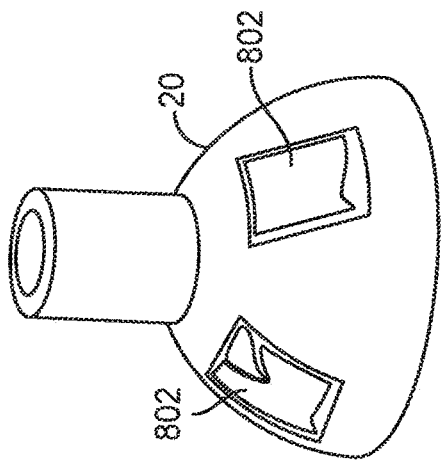

Furthermore, as shown in FIG. 8C, in other embodiments, the vent(s) 800 at the shield 20 may be covered by permeable or semipermeable cover(s) 802. The cover(s) 802 is advantageous because it further limits an amount of air exchange and/or bacterial entry through the wall of the shield 20.

It should be noted that the device 10 is not limited to having the above configurations and features, and that the device 10 may have other configurations and features in other embodiments.

For example, FIGS. 9A-9C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. The shield 20 has a tubular structure 62 at the top of the shield, which functions as a stabilizer to stabilize the umbilical catheter 60 while the umbilical catheter 60 is accommodated in the opening 50. In other embodiments, the shield 20 may not include the tubular structure 62. As shown in the figures, the opening 50 is located at a top of the shield 20, and extends to a side of the shield 20, thereby defining a linear slot 901 at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump. Also, the above configuration is advantageous because it allows the catheter 60 to exit from the opening 50 at any angle relative to the shield 20.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a first portion 902a, a second portion 902b, and a third portion 902c disposed at different respective sides of the shield 20. The portions 902a-902c define respective slots 904a-904c for accommodating the umbilical catheter 60 when the umbilical catheter 60 is wrapped around the shield 20. As shown in the figures, each of the portions 902a-902c has a first cross section at an outermost radial distance from a center of the shield 20, and a second cross section that is smaller than the first cross section at a radial distance that is closer to the center of the shield 20. This configuration forms an anchor to reduce the risk that the umbilical catheter 60 will move radially outward and unwrap itself from the shield 20. Although three portions 902a-902c are shown, in other embodiments, the device 10 may include only a single portion 902, two portions 902, or more than three portions 902.

FIGS. 10A-10C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. The shield 20 has a tubular structure 62 at the top of the shield, which functions as a stabilizer to stabilize the umbilical catheter 60 while the umbilical catheter 60 is accommodated in the opening 50. In other embodiments, the shield 20 may not include the tubular structure 62. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a, 940b disposed at different respective sides of the shield 20. The clips 940a, 940b are configured to detachably hold the umbilical catheter 60 outside the shield 20. Each of the clips 940a, 940b has a first clip portion 944 and a second clip portion 946. The first and second clip portions 944, 946 are separated from each other by a distance to define a clip cavity 948 therebetween. The clip cavity 948 is sized such that the umbilical catheter 60 can be frictionally pushed therein. In the illustrated embodiments, the clip cavity 948 has a first width at the outermost part of the clip 940, and a second width larger than the first width at an inner part of the clip 940. With such configuration, the umbilical catheter 60 will experience a higher friction when initially being pushed radially into the clip cavity 948 of the clip, and once the umbilical catheter 60 passes the outermost part of the clip 940, the umbilical catheter 60 will be accommodated in the inner part of the clip with the larger second width. In some cases, when the umbilical catheter 60 is accommodated in the inner part of the clip 940, the umbilical catheter 60 may experience no clamping force by the clip portions 944, 946. In other cases, the umbilical catheter 60 may experience a slight clamping force by the clip portions 944, 946 that is less compared to the clamping force when the umbilical catheter 60 is being pushed into the clip 940 at the outer most part of the clip 940. In other embodiments, instead of the clip cavity 948 having a larger width at an inner part of the clip 940 compared to the outer part of the clip 940, the clip cavity 948 may have a uniform width extending from the outer part of the clip 940 to an inner part of the clip 940. In further embodiments, the clip cavity 948 may have a decreased width at the inner part of the clip 940 compared to the outer part of the clip 940. Although two clips 940a, 940b are shown, in other embodiments, there may be only one clip 940, or more than two clips 940.

It should be noted that the clip 940 is not limited to the configuration shown, and may have other configurations in other embodiments. For example, instead of having two opposite portions for frictionally grasping the umbilical catheter 60, the clip 940 may include more than two portions (e.g., three portions) that circumferentially engage with different circumferential parts of the umbilical catheter 60.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

FIGS. 11A-11C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a, 940b disposed at different respective sides of the shield 20. The clips 940a, 940b are configured to detachably hold the umbilical catheter 60 outside the shield 20. Although two clips 940a, 940b are shown, in other embodiments, there may be only one clip 940, or more than two clips 940. The features of the clips 940 are similar to those described with reference to FIG. 10A, and therefore will not be repeated here.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

Unlike the embodiments shown in FIG. 10A, the shield 20 in the embodiments of FIGS. 11A-11C does not have the tubular structure 62 at the top of the shield. No stabilizing structure is needed at the top of the shield 20 because the umbilical catheter 60 can be stabilized with respect to the shield 20 by holding the catheter 60 with the clip 920 (with a length of the segment of the catheter 60 between the clip 920 and the opening 50 being as short as possible), by wrapping the umbilical catheter 60 around the spooling groove 924, or by a combination of both.

In addition, unlike the embodiments shown in FIG. 10A, the inner part of the clip cavity 948 in the embodiments of FIGS. 11A-11C is much larger, thereby allowing multiple segments of the umbilical catheter 60 to be placed therein when the umbilical catheter 60 is wrapped around the shield 20 multiple times.

Also, unlike the embodiments shown in FIG. 10A, the spooling groove 942 shown in the embodiments of FIGS. 11A-11C is deeper, thereby allowing the umbilical catheter 60 to be wrapped around the shield 20 multiple times within the spooling groove 942.

Figure 12C:
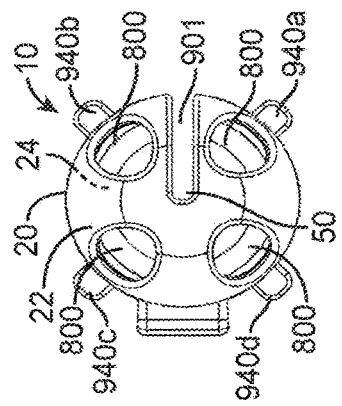
FIG. 12C illustrates a top view of the device of FIG. 12A.
Figure 12B:
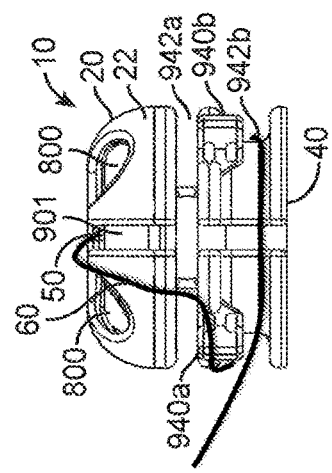
FIG. 12B illustrates a side view of the device of FIG. 12A.
Figure 12A:
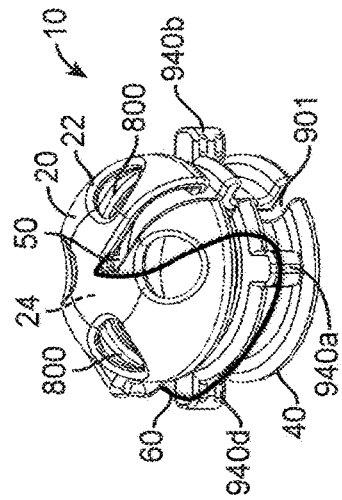
FIG. 12A illustrates a perspective view of another device for protecting an umbilical stump-catheter interface, particularly showing the device being used with a catheter.

In any of the embodiments described herein, the device 10 may have more than one spooling groove 942 for allowing the umbilical catheter 60 to wrap around the shield 20. For example, FIGS. 12A-12C illustrate another device 10 for protecting an umbilical stump-catheter interface, particularly showing the umbilical stump device 10 having multiple spooling grooves. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the shield 20 includes a first circumferentially disposed spooling groove 942a for accommodating a segment of the umbilical catheter 60 while the segment of the umbilical catheter 60 is wrapped around the shield at the spooling groove 942a. The shield 20 also includes a second circumferentially disposed spooling groove 942b for accommodating a segment of the umbilical catheter 60 while the segment of the umbilical catheter 60 is wrapped around the shield at the spooling groove 942b. The first spooling groove 942a is above the second spooling groove 942b to form a stacked configuration. Each of the spooling grooves 942a, 942b may be partially or completely circumferentially disposed around the shield 20. Although two spooling grooves 942a, 942b are shown, in other embodiments, the shield 20 may have only one spooling groove, or more than two spooling grooves 942.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940 are similar to that described in previous embodiments, except that the opening between the clip portions is made smaller to form a very narrow slit. In some cases, the slit has a zero dimension so that the two clip portions at the exterior portion of the clip 940 abut against each other. This configuration is advantageous because once the catheter 60 is pushed through the slit, and is placed in the larger opening at the inner part of the clip 940, the exterior part of the clip 940 where the slit is defined will inhibit or prevent the catheter 60 from falling out of the clip 940.

Figure 13C:
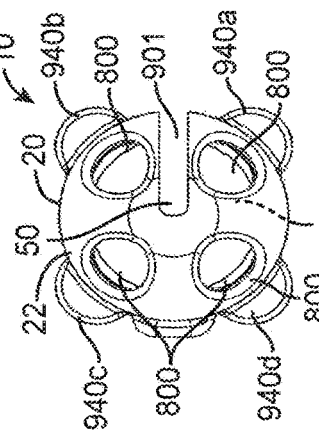
FIG. 13C illustrates a top view of the device of FIG. 13A.
Figure 13B:
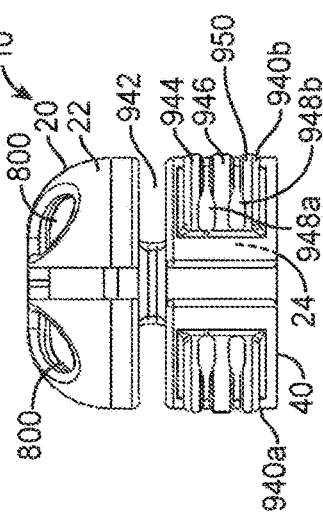
FIG. 13B illustrates a side view of the device of FIG. 13A.
Figure 13A:
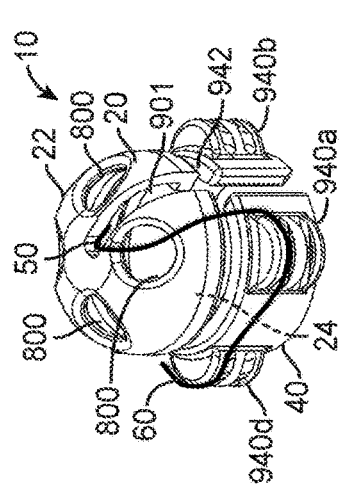
FIG. 13A illustrates a perspective view of another device for protecting an umbilical stump-catheter interface, particularly showing the device being used with a catheter.

FIGS. 13A-13C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. Each of the clips 940a-940d has a first clip portion 944, a second clip portion 946, and a third clip portion 950. The first and second clip portions 944, 946 are separated from each other by a distance to define a first clip cavity 948a therebetween. The second and third clip portions 946, 950 are separated from each other by a distance to define a second clip cavity 948b. The clip cavity 948a/948b is sized such that the umbilical catheter 60 can be frictionally pushed therein. In the illustrated embodiments, the clip cavity 948a/948b has a first width at the outermost part of the clip 940, and a second width larger than the first width at an inner part of the clip 940. With such configuration, the umbilical catheter 60 will experience a higher friction when initially being pushed radially into the clip cavity 948a/948b of the clip, and once the umbilical catheter 60 passes the outermost part of the clip 940, the umbilical catheter 60 will be accommodated in the inner part of the clip with the larger second width. In some cases, when the umbilical catheter 60 is accommodated in the inner part of the clip 940, the umbilical catheter 60 may experience no clamping force by the clip portions 944, 946, or by the clip portions 946, 950 (depending whether the clip cavity 948a or the clip cavity 948b is being used). In other cases, the umbilical catheter 60 may experience a slight clamping force by the clip portions 944, 946, or by the clip portions 946, 950 that is less compared to the clamping force when the umbilical catheter 60 is being pushed into the clip 940 at the outer most part of the clip 940. In other embodiments, instead of the clip cavity 948a/948b having a larger width at an inner part of the clip 940 compared to the outer part of the clip 940, the clip cavity 948a/948b may have a uniform width extending from the outer part of the clip 940 to an inner part of the clip 940. In further embodiments, the clip cavity 948a/948b may have a decreased width at the inner part of the clip 940 compared to the outer part of the clip 940. Although four clips 940a-940d are shown, in other embodiments, there may be fewer than four clips 940, or more than four clips 940.

In the illustrated embodiments, each clip 940 has multiple stacked slots 948 for allowing a user to couple the umbilical catheter 60 to a selected one of the slots 948, and/or for allowing a user to wrap the umbilical catheter 60 around the shield 20 multiple times. In other embodiments, the number of slots 948 in each clip 940 may be more than two (e.g., three, four, etc.). Also, it should be noted that the stacked slots 948 feature is not limited to the embodiments of FIGS. 13A-13C, and that other embodiments described herein may optionally include the stacked slots feature.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

Figure 14C:
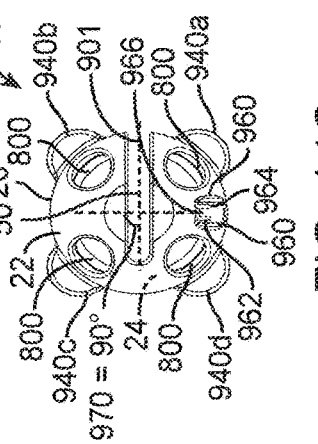
FIG. 14C illustrates a top view of the device of FIG. 14A.
Figure 14B:
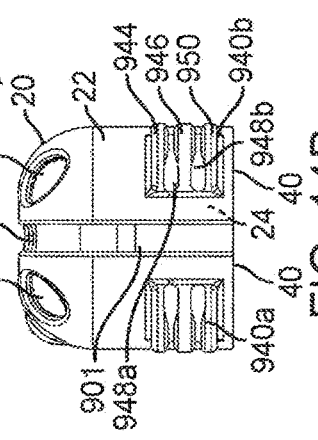
FIG. 14B illustrates a side view of the device of FIG. 14A.
Figure 14A:
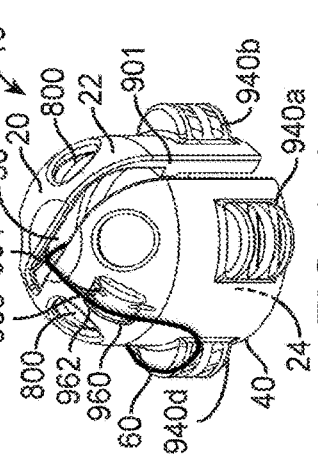
FIG. 14A illustrates a perspective view of another device for protecting an umbilical stump-catheter interface, particularly showing the device being used with a catheter.

In any of the embodiments described herein, the device 10 may optionally further include a top clip for detachably securing the umbilical catheter 60 at a top cover of the shield 20. For example, FIGS. 14A-14C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the device 10 also includes a top clip 960 located at the upper portion of the shield 20 for detachably securing the umbilical catheter 60 relative to the shield 20. The clip 960 includes a first clip portion 962 and a second clip portion 964. The first and second clip portions 962, 964 are separated from each other by a distance to define a slot 966. The slot 966 is sized so that the umbilical catheter 60 may be frictionally pushed therein and be clamped by the first and second clip portions 962, 964. The top clip 960 is advantageous because it not only secures the umbilical catheter 60 relative to the top portion (cover) of the shield 20, but it also directs the umbilical catheter 60 towards a bottom portion of the shield 20 where the clips 940a-940d are located, so that after a first segment of the umbilical catheter 60 is secured by the top clip 960, the next segment of the umbilical catheter 60 may be secured by one of the clips 940a-940d. As shown in FIG. 14C, the slot 966 is oriented at an angle 970 that is 90° from a direction of the slot 901. In other embodiments, the angle 970 may be more than 90°. Having the angle 970 to be 90° or more is advantageous because it reduces the risk that the umbilical catheter 60 will move out of the slot 901 and become loose.

In other embodiments, the first and second clip portions 962, 964 do not frictionally clamp the umbilical catheter 60. Instead, the first and second clip portions 962, 964 are sufficiently spaced apart so that they do not clamp against the umbilical catheter 60. In such case, the top clip 960 functions to guide the umbilical catheter 60 towards a desired direction. Thus, as used in this specification, the term "clip" is not necessarily limit to a structure that grasp or grip an object (e.g., catheter), and may refer to any structure that accommodates, guide, abut, or touches the object (e.g., catheter).

Figure 19A:
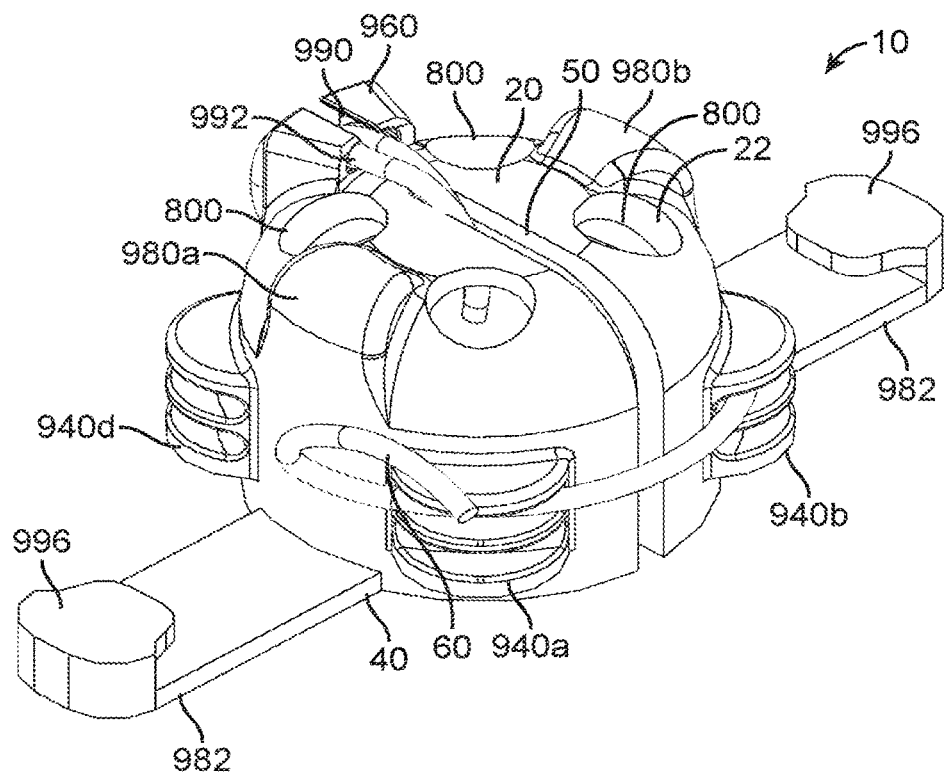
FIG. 19A illustrates a device for protecting umbilical stump-catheter interface, particularly showing the device being used with one catheter.

For example, in other embodiments, the clip 960 may have a configuration like that shown in FIG. 19A, which includes a narrow slot 990 and a larger slot 992 (larger than slot 990). In this configuration, the catheter 60 may first be pushed through the narrow slot 990. Once the catheter 60 is contained in the larger slot 992, the portions defining the narrow slot 990 (due to its width being narrower than a width of the catheter 60) will inhibit or prevent the catheter 60 from escaping larger slot 992.

Although only one top clip 960 is shown in FIG. 14A, in other embodiments, there may be multiple top clips 960 disposed at the upper portion of the shield 20 for allowing a user to selectively pick to secure the umbilical catheter 60.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940a-940d are similar or the same as those described with reference to FIGS. 12A-12C and 13A-13C, and therefore will not be described again. Although four clips 940a-940d are shown, in other embodiments, there may be fewer than four clips 940, or more than four clips 940.

In other embodiments, the device 10 of FIGS. 14A-14C may include one or more spooling groove(s) 942 as similarly described with other embodiments herein.

Figure 15A:
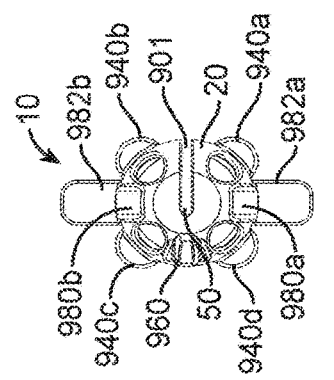
FIG. 15A illustrates a perspective view of another device for protecting an umbilical stump-catheter interface, particularly showing the device being used with a catheter.
Figure 15B:
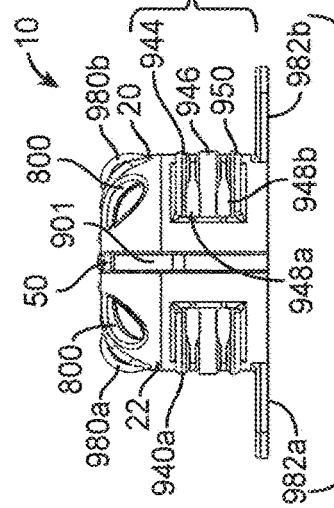
FIG. 15B illustrates a side view of the device of FIG. 15A.
Figure 15C:
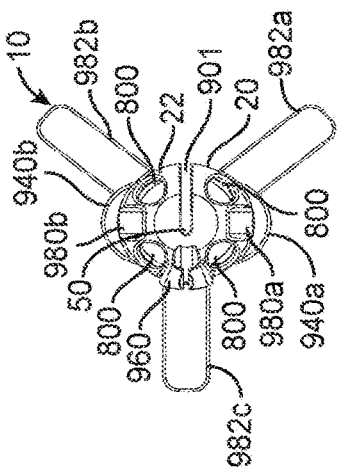
FIG. 15C illustrates a top view of the device of FIG. 15A.

In any of the embodiments described herein, the device 10 may optionally further include two or more pinching protrusions (e.g., taps) for allowing a user to grasp the device 10. For example, FIGS. 15A-15C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the device 10 also includes a first pinching protrusion 980a and a second pinching protrusion 980b located on respective opposite sides from each other and at the upper portion of the shield 20. The pinching protrusions 980a, 980b are configured for allowing a user to grasp the device 10 using fingers. In other embodiments, there may be more than two pinching protrusions. Also, in other embodiments, the pinching protrusions 980 may be located at other areas at the shield 20.

In the illustrated embodiments, the device 10 also includes a top clip 960 located at the upper portion of the shield 20 for detachably securing the umbilical catheter 60 relative to the shield 20. The clip 960 is similar to or the same as the clip 960 described with reference to FIGS. 14A-14C, and therefore will not be described again. Although only one top clip 960 is shown, in other embodiments, there may be multiple top clips 960 disposed at the upper portion of the shield 20 for allowing a user to selectively pick to secure the umbilical catheter 60.

The shield 20 also has multiple vents 800. The vents 800 may inhibit or prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940a-940d are similar or the same as those described with reference to FIGS. 12A-12C and 13A-13C, and therefore will not be described again. Although four clips 940a-940d are shown, in other embodiments, there may be fewer than four clips 940, or more than four clips 940.

In other embodiments, the device 10 of FIGS. 15A-15C may include one or more spooling groove(s) 942 as similarly described with other embodiments herein.

Also, as shown in FIGS. 15A-15C, the base 40 of the device 10 may include a plurality of flanges 982a, 982b extending laterally from sides of the shield 20. The flanges 982a, 982b may include adhesive at the underneath surfaces for attachment to a patient. Additionally, or alternatively, each of the flanges 982a, 982b may be taped to the patient using medical tape that extends across the top surface of the flange 982a/982b. The flanges 982a, 982b are advantageous because they provide an increased adhesive area for attachment to the patient, which provides a more secured attachment mechanism. Additionally, or alternatively, the flanges may be taped down to a "safe" adhesive (as described previously to allow for better securement of the device while ensuring that only a "safe" adhesive interfaces with the skin.

Figure 16A:
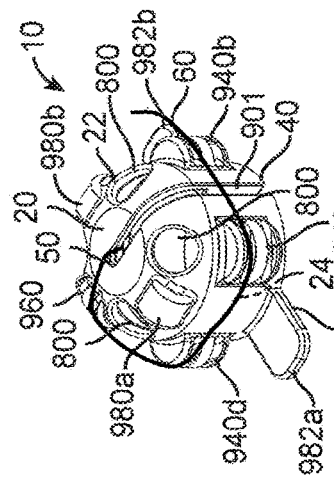
FIG. 16A illustrates a perspective view of another device for protecting an umbilical stump-catheter interface, particularly showing the device being used with a catheter.
Figure 16B:
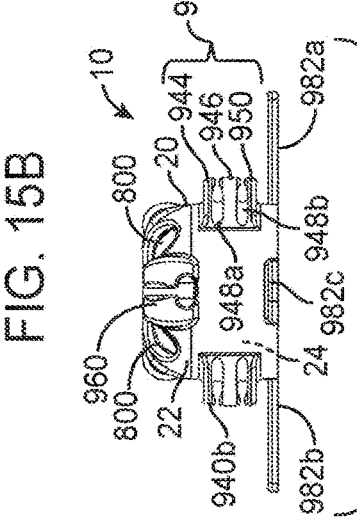
FIG. 16B illustrates a side view of the device of FIG. 16A.
Figure 16C:
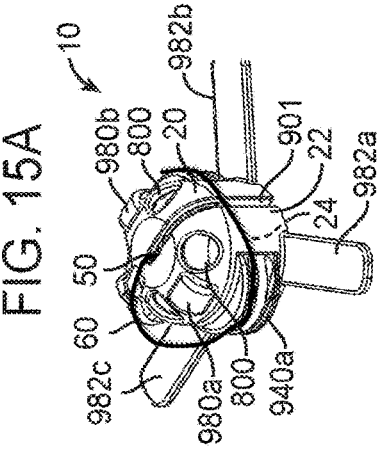
FIG. 16C illustrates a top view of the device of FIG. 16A.

Although only two flanges 982 are shown, in other embodiments, there may be more than two flanges 982. For example, FIGS. 16A-16C illustrates a variation of the device 10 that includes three flanges 982a-982c disposed circumferentially around the shield 20.

Figure 17:
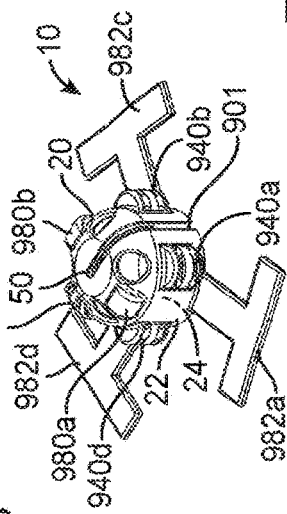
FIG. 17 illustrates another device for protecting an umbilical stump-catheter interface.
Figure 18:
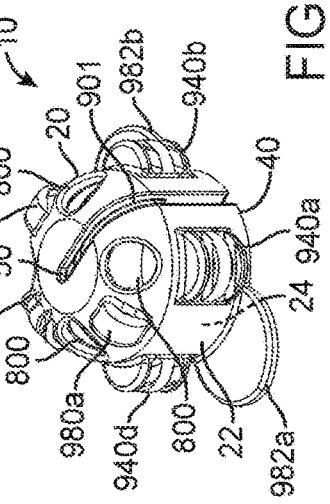
FIG. 18 illustrates another device for protecting an umbilical stump-catheter interface.

Also, it should be noted that the flanges 982 are not limited to having rectangular shape like that shown in FIGS. 15-16, and that each of the flanges 982 may have other shapes in other embodiments. For example, in other embodiments, each of the flanges 982 may have a curvilinear shape like that shown in FIG. 17, or a T-shape like that shown in FIG. 18. In addition, in any of the embodiments described herein, a flange 982 may have an anchor (e.g., along a side of the flange 982) for inhibiting or preventing or reducing the risk of a tape being detached from the flange 982. In particular, during use of the device 10, a tape may be used to tape down the flange 982 relative to the patient, while the tape is placed underneath the anchor at the flange 982. The anchor functions to inhibit or prevent the tape from being pulled upward from the flange 982.

It should be noted that the flange feature is not limited to the embodiments shown in FIGS. 15-18, and it may be included in any of the other embodiments described herein.

Also, in any of the embodiments described herein (e.g., those described in FIGS. 1-17), the device 10 may optionally further include an exterior surface configured for allowing a user to write on. For example, a top portion (e.g., a cover) of the shield 20 may have an exterior surface that forms a dedicated area for allowing a user to write thereon. The dedicated area may comprise a paper, which allows the user to write thereon using pencil or pen. Alternatively, the dedicated area may comprise a plastic sheet, which allows the user to write thereon using a marker. Also, in some embodiments, the dedicated area may comprise a sheet (paper, plastic, etc.) that is removably attached to the shield 20.

Furthermore, in any of the embodiments described herein (e.g., those described in FIGS. 1-17), the device 10 may be made from different materials. For example, a first portion of the shield 20 may be made from a first material, and a second portion of the shield 20 may be made from a second material that is different from the first material. In some cases, the clip(s) 940 and/or the clip(s) 960 may be made from a first material having a first durometer, and another portion of the shield 20 (e.g., the body defining the cavity 24) may be made from a second material having a second durometer, wherein the first durometer is higher than the second durometer.

Also, in any of the embodiments described herein (e.g., those described in FIGS. 1-17), instead of or in addition to, having the opening 50 at the top of the device 10, the device 10 may include an opening at another part of the device 10. For example, in other embodiments, the device 10 may include an opening at a side of the device 10, or at a location that is offset from a center at the top of the device 10.

Figure 19B:
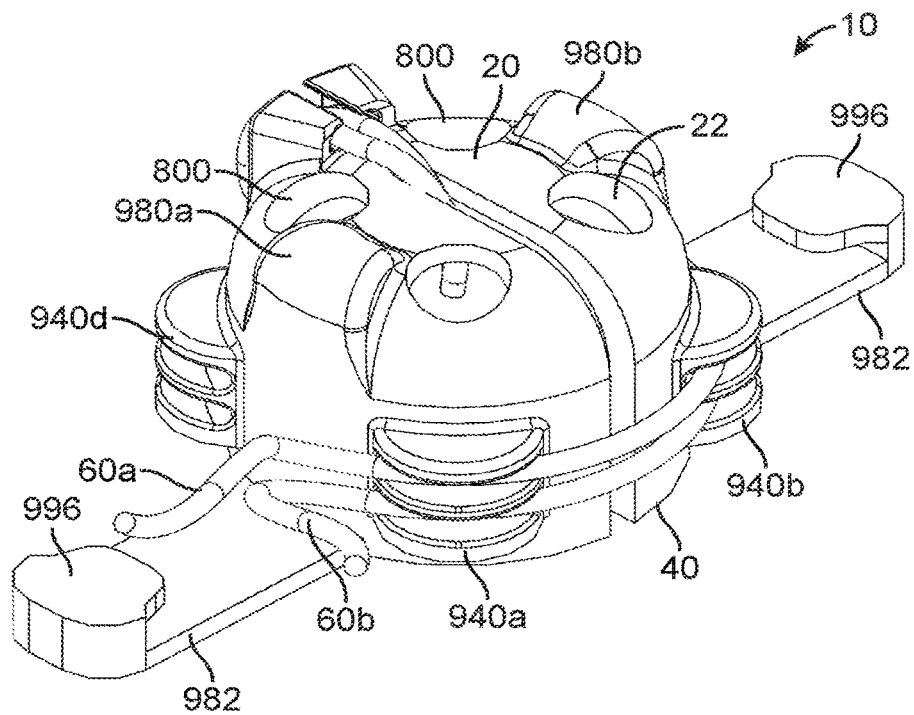
FIG. 19B illustrates a device for protecting umbilical stump-catheter interface, particularly showing the device being used with two catheters.

In the above embodiments, the device 10 is illustrated as being used with one catheter. In any of the embodiments described herein (e.g., those described in FIGS. 1-17), the device 10 may have multiple clips for holding different catheters. For example, the device 10 may have a first clip for holding a first catheter, and a second clip for holding a second catheter. Thus, the device 10 may selectively be used with one or more catheters. FIG. 19A illustrates another device 10 for protecting an umbilical stump-catheter interface, particularly showing the device 10 being used with one catheter 60. However, the same device 10 may also be used with two (or more) catheters. As shown in FIG. 19B, the device 10 is being used with two catheters 60a, 60b. In some cases, the catheters may have different sizes. Thus, in some embodiments, the clips may have different respective sizes. For example, the first clip may have a first catheter slot, and the second clip may have a second catheter slot, wherein the first catheter slot has a dimension that is different from a dimension of the second catheter slot. In other embodiments, the clips may have the same size (e.g., the catheter slots in the clips may have the same size). In further embodiments, the device 10 may have at least three clips for holding three different respective catheters. In any of the embodiments described herein, two or more of the clips may be integrated together as a single component.

Also, as discussed, in some cases, the flanges 982 of the device 10 may be taped down to a patient using a tape. In any of the embodiments described herein, the device 10 may optionally include one or more anchors for inhibiting or preventing or reducing the risk of detachment of the tape from the patient. For example, as shown in the embodiments of FIG. 19A or 19B, each flange 982 may include an anchor 996 at a side of the flange 982. During use, a tape may be placed under the anchor 996 and may be used to tape the flange 982 onto a patient. Because the anchor 996 is above the tape, it functions as an anchor that assists the tape in maintaining its position with respect to the patient.

In addition, in any of the embodiments described herein (e.g., those described in FIGS. 1-17), the device 10 may optionally further include a color-coding and/or labeling. For example, the color coding or labeling may indicate whether a catheter is a venous catheter or an arterial catheter, length of catheter in the patient, etc. In one implementation, the device 10 may include a surface for allowing a nurse or physician to write on. Also, in some embodiments, the labeling may include a single letter indicating whether a catheter is a venous catheter (e.g., letter "V") or an arterial catheter (e.g., letter "A"). Furthermore, in some cases, the labeling may include a number code indicating a length of a catheter.

Furthermore, in any of the embodiments described herein (e.g., those described in FIGS. 1-17), the device 10 may have a cross sectional dimension (e.g., width of shield portion of the device 10 excluding the clips 940 and flanges 982) that is anywhere from 0.5 inch to 5 inches, and more preferably from 0.5 to 3 inches, and more preferably from 0.5 to 2 inches, and even more preferably from 0.5 to 1.5 inches (e.g., 1 inch). In other embodiments, the device 10 may have a cross sectional dimension that is larger than 5 inches. Also, in any of the embodiments described herein, the device 10 may have a wall thickness that is anywhere from 0.02 inch to 0.5 inch, and more preferably from 0.05 to 0.3 inch, and even more preferably from 0.06 to 0.1 inch.

In any of the embodiments described herein (e.g., those described in FIGS. 1-17), the device 10 may be made from a molding process. For example, injection molding, compressing molding, etc., may be used to form part(s) or an entirety of the device 10. In some cases, different molding processes may be used to form different parts of the device 10, and the parts may then be subsequently secured to each other (e.g., using an adhesive, glue, etc.). Various materials may be used to form the device 10. By means of non-limiting examples, the device 10 may be formed from thermoplastic material(s), elastomer(s), polymer(s), etc.

In any of the embodiments described herein, the spooling groove(s) is optional, and the device 10 may not include any spooling groove. For example, in any of the embodiments that includes a spooling groove, such spooling groove may be replaced with one or more clips. The clip(s) is configured to both hold the catheter and to define a position and direction of travel for the catheter.

In any of the embodiments described herein (e.g., those described in FIGS. 1-17), the device 10 may include an antimicrobial component. For example, the device 10 itself may be made from an antimicrobial material. In one implementation, the base of the device 10 includes an antimicrobial material. Alternatively, the entire device 10 may include the antimicrobial material. In some cases, the device 10 may include a ultraviolet (UV) light source coupled to the shield 20 for projecting a UV light towards the stump 30. In further embodiments, the device 10 may include silver, gel, etc. that provides antimicrobial action.

In any of the embodiments described herein (e.g., those described in FIGS. 1-17), the shield 20 may be configured to deform, bend, or collapse in response to a compression force that is less than about 1 lb, and more preferably less than about 0.5 lb, and even more preferably less than about 0.3 lb. This configuration is advantageous because it allows the baby using the device 10 to be in various positions, such as in a facedown position. In particular, if the baby is lying on his/her belly, the device 10 will deform, bend, or collapse so that the device 10 will not be applying an uncomfortable force against the baby, while the position of the catheter relative to the device 10 remains fixed.

In any of the embodiments described herein (e.g., those described in FIGS. 1-17), the device 10 may further include a manual control mechanism (e.g., a clip, a knob, a pincher, etc.) configured to shut the catheter so that fluid flow in the catheter can be stopped when desired. The manual control mechanism may be located at an exterior surface of the shield 20, at the base, or at any of other locations (e.g., at the device-catheter interface). In one implementation, a clip or a mechanism similar to a wingnut/bolt that is used to tighten may be provided at the device-catheter interface for shutting the catheter.

In any of the embodiments described herein (e.g., those described in FIGS. 1-17), the device 10 may further include a position monitoring device for monitoring a position of the catheter with respect to the device 10 (e.g., the shield 20 of the device 10). For example, the position monitoring device may be a marking at the catheter to indicate its position relative to the shield 20. If the position has changed so that the marking on the catheter is further from the shield 20, then it can be inferred that the catheter has moved outward from the patient. Thus, the position monitoring device functions to monitor the depth of the catheter outside of the shield 20. In other embodiments, the position monitoring device may include markers on the catheter, and a camera for viewing the markers on the catheter. Also, in further embodiments, similar techniques may be employed to monitor the position of the catheter with respect to the patient or to the umbilical stump.

In some embodiments, different sizes of the device 10 may be provided. For example, there may be three standard sizes of the device 10, with the larger size being more suitable for larger patient, and the smaller size being more suitable for smaller patient.

In any of the embodiments described herein, if the device 10 includes multiple clips for holding different catheters, the clips may be color coded. For example, a first clip may have a first color, and a second clip may have a second color that is different from the first color. Also, if the device 10 includes a clip that is configured to hold multiple catheters, different portions of the clip may be color coded. For example, a first portion of the clip may define a space for accommodating a first catheter, and a second portion of the clip may define another space for accommodating a second catheter, wherein the first portion and the second portion may have different respective colors.

Embodiments disclosed in U.S. Provisional Patent Application No. 62/156,120, filed on May 1, 2015, U.S. Provisional Patent Application No. 62/307,396, filed on Mar. 11, 2016, and U.S. patent application Ser. No. 15/098,286, filed on Apr. 13, 2016 are herein incorporated by reference in their entirety for all purposes.

Figure 20I:
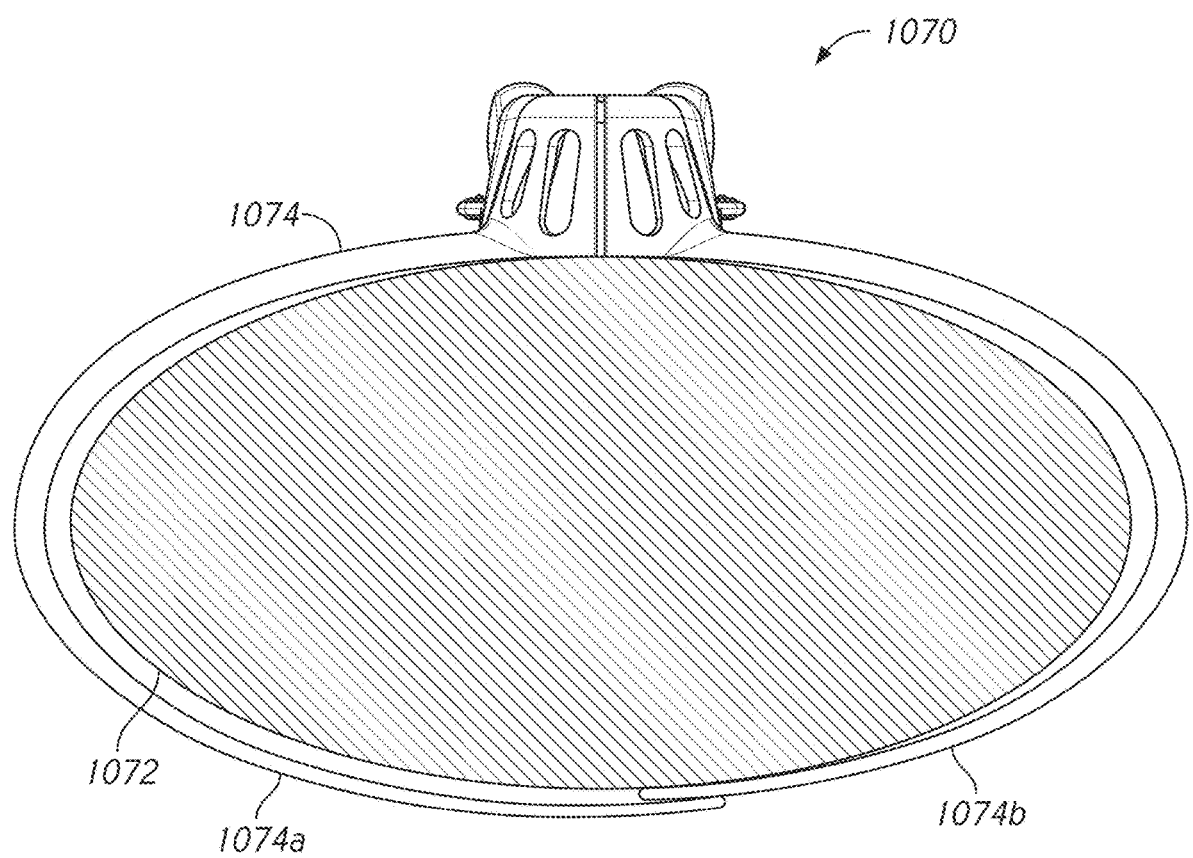
FIG. 20I is a cross-sectional view of an example device 1070 interacting with a subject 1072.

FIG. 20Ai is a top, front, and side view of an example device 1000 for protecting a catheter interface (e.g., an umbilical stump-umbilical catheter interface). FIGS. 20Aii and 20Aiii are additional top, front, and side views of the device 1000 of FIG. 20Ai. The device 1000 can include several features described herein, for example, a shield 1002 (e.g., optionally having features disclosed with respect to the shield 20), a cavity 1001 at least partially defined by the shield 1002 (e.g., optionally having features disclosed with respect to the cavity 24), vents 1004 (e.g., optionally having features disclosed with respect to the vents 800), a slot 1006 (e.g., optionally having features disclosed with respect to the slot 901), an opening 1008 (e.g., optionally having features disclosed with respect to the opening 50), flanges 1010 (e.g., optionally having features disclosed with respect to the flanges 982), anchors 1012 (e.g., optionally having features disclosed with respect to the anchors 996), and clips 1018 (e.g., optionally having features disclosed with respect to the clips 940, 960). In some embodiments, some of these features may be omitted from the device 1000. The device 1000 may additionally or alternatively include other features described herein, for example, one or more of a base 40, a hinge 80, a securing device 90, catheter engagement structures such as first seal portion 102 and the second seal portion 104 and/or the spring loaded control 450, adhesive 142 (e.g., under the flanges 1010, a bottom of the shield 102, and/or a base 40), a tape cover 144, a second opening 420 optionally with a cover 430, a semipermeable cover 802, pinching protrusions 980, a spooling groove 942, etc.

In some embodiments, all of the features of the device 1000 may be monolithically or integrally formed (e.g., via molding such as injection molding or press forming or compression molding), for example as opposed to being assembled from a plurality of pieces. In comparison to an assembled device, monolithic formation can, for example, reduce device-to-device variability, simplify validation (e.g., reducing or eliminating validation of coupling methods), reduce manufacturing costs, reduce manufacturing handling, reduce potential issues associated with removing material, reduce the potential for bacteria or debris building up at junctions, and/or produce stronger coupling points. For example, interfaces between the shield 1002 and the tethers 1016, between the latches 1014 and the tethers 1016, between the shield 1002 and the flanges 1010, and/or between the shield 1002 and the clips 1018 may be considered critical junctions that can benefit from monolithic formation.

The device 1000 comprises or, for example in the case of monolithic formation, consists essentially of, a biocompatible material having suitable characteristics. For example, the device 1000 or one or more parts thereof may comprise a material having a certain tensile strength, elongation ability, surface friction, refractive index, rate of change upon sterilization (e.g., using ethylene oxide (EtOH) or steam), or other aspects. In some embodiments, the device 1000 or one or more parts thereof comprises a material having a tensile strength between about 100 psi and about 2,000 psi (e.g., about 100 psi, about 250 psi, about 500 psi, about 1,000 psi, about 1,500 psi, about 2,000 psi, ranges between such values, and the like). In some embodiments, the device 1000 or one or more parts thereof (e.g., the tethers 1016) comprises a material having an elongation at break between about 200% and about 700% psi (e.g., about 200%, about 300%, about 400%, about 500%, about 600%, about 700%, ranges between such values, and the like). In some embodiments, the device 1000 or one or more parts thereof comprises a material having a shore A durometer between about 40 and about 80 (e.g., about 40, about 50, about 60, about 70, about 80, ranges between such values, and the like). In some embodiments, the device 1000 or one or more parts thereof (e.g., the tethers 1016, the shield 1002, part of the shield 1002 proximate the tethers 1016, part of the shield around the opening 1008) comprises a material having a static friction coefficient of the material with the engaging polymeric/elastomeric tubular member between about 0.2 and about 1.2 (e.g., about 0.2, about 0.4, about 0.6, about 0.8, about 1, about 1.2, ranges between such values, and the like). In some embodiments, the device 1000 or one or more parts thereof (e.g., the upper surface 1003) comprises a material having a translucency or refractive index between about 1.0 and about 2.0 (e.g., about 1.0, about 1.25, about 1.5, about 1.75, about 2.0, ranges between such values, and the like), where lower values are more translucent and higher values are more transparent. In some embodiments, the device 1000 or one or more parts thereof comprises a material having properties (e.g., described above and/or other properties) that change, upon sterilization and preferably resterilization (e.g., using a steam autoclave), less than about 25%, less than about 20%, less than about 15%, less than about 10%, less than about 5%, or less than about 1%, with no change or 0% being an end of ranges including such values. Ability to be resterilized can allow some reuse, which can be advantageous, for example, in jurisdictions with limited funds. In some embodiments, the device 1000 or one or more parts thereof comprises a material capable of providing a holding force between about 0.5 lb and about 5 lb (e.g., about 0.5 lb, about 1 lb, about 2 lb, about 3 lb, about 4 lb, about 5 lb, ranges between such values, and the like). In this context, holding force can mean that upon application of the force on a catheter interacting with the device, the catheter moves less than 5 mm from the umbilical stump or body part in which the catheter is positioned. In some embodiments, the device 1000 or one or more parts thereof (e.g., the shield 1002) comprises a material resistant to or that does not support microbial growth. Dimensions of the device 1000 can be varied to exploit one or more of these features for particular parts (e.g., by increasing wall thickness to increase rigidity, decreasing wall thickness to decrease rigidity and/or increase flexibility, increasing surface area to increase friction surfaces, etc.). A flexible shield 1002 can allow the shield 1002 to be moved without moving a catheter. Features such as vents 1004 and/or a slot 1006 can increase flexibility. In some embodiments, a material may comprise two or more, or even, all of these properties.

In some embodiments, the device 1000 or one or more parts thereof comprises, or alternatively consists essentially of, thermoplastic elastomer (TPE) and/or thermoplastic urethane (TPU). For example, TPE/TPU may be appropriate for parts that are preferably rigid (e.g., the clips 1018 and/or the anchors 1012). TPE/TPU may comprise ARE-75A, ARE-80A, ALE-70A, ALE-75A, ARC-75A, ARC-80A, ALC-75A, and/or ALC-80A from Biomerics, LLC of Salt Lake City, Utah, 500502M, 500552M, 500602M, and/or 500652M from Hexpol of Malmö, Sweden, 1040-0000, 1050-0000, 1060-0007, 1068-0000, 9045-1001, 9055-1007, 9060-1000, 9070-1000, 9050-PF00, and/or 9065-PF00 from Star Thermoplastic Alloys & Rubbers, Inc. of Broadview, Illinois, combinations thereof, and/or other resins. In some embodiments, the device 1000 or one or more parts thereof comprises, or alternatively consists essentially of, silicone (e.g., polymerized siloxanes such as polydimethylsiloxane). For example, the silicone may comprise MED-4940, MED-4950, MED-4960, MED-4970, and/or MED-4980 from NuSil Technology LLC of Carpinteria, California, KE-1950-40A/B, KE-1950-50A/B, KE-1950-60A/B, KE-1950-70A/B, KEG-2000-40A/B, KEG-2000-50A/B, KEG-2000-60A/B, KEG-2000-70A/B, KEG-2001-40A/B, and/or KEG-2001-50A/B from Shin-Etsu Chemical Co., Ltd., and/or other silicones. Combinations of materials (e.g., TPE/TPU for some parts of the device 1000 and silicone for other parts of the device 1000) are also possible.

The device 1000 includes a latch 1014 and tethers 1016. The latch 1014 is configured to interact with a clip 1018. The clip 1018 may be a portion or part or piece of a catheter securement mechanism. In some implementations, the portion of the latch 1014 may fit in the portion of the clip 1018. In some implementations, at least one catheter diameter may be between the portion of the latch 1014 and the portion of the clip 1018. The device 1000 includes two latches 1014 and two clips 1018, but more or fewer latches 1014 and/or clips 1018 are also possible (e.g., between 1 latch and 8 latches (e.g., 1 latch, 2 latches, 3 latches, 4 latches, 5 latches, 6 latches, 7 latches, 8 latches, ranges between such values, and the like) and/or between 1 latch and 8 latches (e.g., 1 clip, 2 clips, 3 clips, 4 clips, 5 clips, 6 clips, 7 clips, 8 clips, ranges between such values, and the like)). In some embodiments, a single latch 1014 may interact with two or more clips 1018. In some embodiments, multiple latches 1014 may interact with a single clip 1018 (e.g., a first latch 1014 interacting with an upper side of the clip 1018 and a second latch 1014 interacting with a lower side of the clip 1018). In some embodiments, the latch 1014 comprises a gripping pattern configured to improve grip, for example protrusions 1015, grooves, lines, texture, combinations thereof, and the like. In some embodiments, indicia (e.g., an "A" for arterial or a "V" for venous) may be embossed and provide grip. In some embodiments, the laches may be colored or marked (e.g., to provide distinction for an arterial side and a venous side).

Two tethers 1016 are shown for each latch 1014, but more or fewer tethers 1016 are also possible. The tethers 1016 may be configured to contribute to the interaction between the latch 1014 and the clip 1018 (e.g., elastically pulling the latch 1014 towards the clip 1018 in a locked position). The tethers 1016 may be configured to so that the latches 1014 are coupled to the device 1000 so as to not be losable. The tethers 1016 may be configured so that the latches 1014 may be monolithically formed with the other features of the device 1000. When a catheter is positioned under the clip 1018 and the latch 1014 is engaged with the clip 1018, the tethers 1016 can contribute to securing the catheter by frictionally engaging the catheter against a wall of the shield 1002. Together, the latch 1014 and the clip 1018, and optionally the tethers 1016, can form a locking mechanism.

FIG. 20Bi is top view of the device 1000. FIG. 20Bii is another top view of the device 1000. The upper surface 1003 or top of the shield 1002 is at least partially transparent, which is best seen in FIGS. 20Aii, 20Bi, and 20D. Other parts of the shield 1002 may be at least partially transparent and/or provide transparent-like effects. For example, the vents 1004 can be devoid of material and thus transparent. Spaces between the vents 1004 and/or other parts of the shield 1002, for example, may comprise optically transparent material. Referring again to FIG. 20Aiii, the surface variation 1020 of the upper surface may be between about 100 nm and about 500 nm (e.g., about 100 nm, about 150 nm, about 200 nm, about 250 nm, about 300 nm, about 350 nm, about 400 nm, about 450 nm, about 500 nm, ranges between these values, and the like). The surface variation 1020 that provides at least partial transparency may vary depending on the material of the upper surface 103. The upper surface 1003 is preferably transparent enough that the umbilical stump or other anatomy can be visualized therethrough. In some embodiments, a surface may be considered suitably transparent if catheter indicia may be read without removal of the device 1000. For example, users may regularly (e.g., once per hour, once per two hours, once per three hours, once per four hours, once per six hours, once per eight hours, once per twelve hours, once per eighteen hours, once per day, ranges between such values, etc.) review catheter indicia (e.g., ruler-like markings denoting insertion depth) to check whether the catheter has moved in the subject. Readings of such indicia can be logged. In some embodiments, a surface may be considered suitably transparent if the anatomy thereunder may be visualized in a manner that can diagnose injection, bleeding, omphalitis. In some embodiments, vents 1004 can provide visualization. The upper surface 1003 is preferably substantially flat (e.g., planar or non-rounded), for example so the transparency does not substantially vary based on a viewing angle A flat upper surface 1003 can reduce or minimize optical refraction. A flat upper surface 1003 can increase or maximize visibility through the shield 1002. In some implementations, the shield 1002 may be curved to strategically refract light and/or optically magnify areas within the shield 1002 (e.g., similar to a lens). The selected material and the thickness of the transparent portion of the shield 1002 are configured to allow for visualization through the shield 1002. Portions of the shield 1002 that are intended to be seen-through may be more transparent than other portions of the device 1000. In implementations in which the device 1000 is molded, the mold may be more polished in at portions of the shield 1002 that are intended to be seen-through and the mold may be less polished in other areas of the device 1000. Such polishing differences can facilitate manufacturing (e.g., reducing steps, increasing throughput) and/or longevity of the tools use to produce the device 1000.

In some embodiments, the device 1000 may be dimensioned at least partially based on maximizing the area of the upper surface 1003 and thus the visible window. Another consideration may be angling sidewalls of the shield 1002 and sizing the vents 1004 so that a through-aperture of a vent 1004 is exposed vertically (e.g., as best seen in FIG. 20Bii) and/or horizontally (e.g., as best seen in FIG. 20E). If the shield 1002 is molded, the dimensions of the open bottom may be larger than the dimensions of the upper surface 1003. The open bottom may be dimensioned at least partially based on intended use. For example, a shield 1002 used with an umbilical stump of a premature baby may have an area between about 0.5 cm$^2$ and about 4 cm$^2$ (e.g., about 0.5 cm$^2$, about 1 cm$^2$, about 1.5 cm$^2$, about 2 cm$^2$, about 2.5 cm$^2$, about 3 cm$^2$, about 3.5 cm$^2$, about 4 cm$^2$, ranges between such values, and the like). Larger sizes are also possible, for example for larger babies or other uses. In some embodiments, the open base have a dimension of up to 1 cm in any direction.

As shown in FIG. 20Bii, the latching mechanisms are at an angle 1022 to an axis defined by the slot 1006. The angle 1022 may be between about 0° (e.g., a locking mechanism opposite the slot 1006) and about 180° (e.g., including the slot 1006 or slightly circumferentially offset from the slot 1006) (e.g., about 0°, about 15°, about 30°, about 45°, about 60°, about 90°, about 120°, about 150°, about 180°, ranges between these values, and the like). The angle 1022 may be defined with respect to other features of the device 1000 (e.g., the opening 1008, a flange 1010, a vent 1004). In embodiments comprising multiple locking mechanisms, the locking mechanisms may be mirror images (e.g., having the same angle 1022). Different angles 1022 for different locking mechanisms are also possible. As shown in FIG. 20G, angled locking mechanisms can allow tape to be placed over the flanges 1010 without interference by the locking mechanisms.

FIG. 20Ci is an expanded top view of the device 1000 in the area of the circle 20Ci of FIG. 20Bii. The upper surface 1003 includes an opening 1008. A slot 1006 extends from the opening 1008. A width 1024 of the slot 1006 may be less than about 1.2 mm, more preferably less than about 1 mm, and even more preferably than about 0.8 mm. For example, a 3.5 Fr umbilical catheter has an outer diameter of about 1.17 mm, so a slot having a width 1024 can generally inhibit or prevent the catheter from traversing the slot 1006 unintended.

The opening 1008 is configured to allow an umbilical catheter to extend therethrough. The opening 1008 illustrated in FIGS. 20Ai-20D and best seen in FIG. 20C includes a first arcuate portion 1008a and a second arcuate portion 1008b. The shape may be described as dog-bone, infinity, figure-8, connected eyes, or other descriptive terms. The first arcuate portion 1008a and/or the second arcuate portion 1008b may have a radius 1026 between about 0.3 mm and about 1 mm (e.g., about 0.3 mm, about 0.4 mm, about 0.5 mm, about 0.6 mm, about 0.7 mm, about 0.8 mm, about 0.9 mm, about 1 mm, ranges between these values, and the like). In implementations in which two catheters are used (e.g., as generally shown in FIG. 3B), one of the catheters may snap into fit in the first arcuate portion 1008a and the other of the catheters may snap into fit in the second arcuate portion 1008b. The radius 1026 of the first arcuate portion 1008a and the second arcuate portion 1008b may be the same or different. Catheters may snap into fit in the first arcuate portion 1008a or the second arcuate portion 1008b, and/or may settle in the intersection or junction 1008j between the first arcuate portion 1008a and the second arcuate portion 1008b. The intersection includes at least three surfaces that can act as fingers to hold the catheter in place (e.g., frictionally). Other shapes are also possible (e.g. a single arcuate portion, more than two arcuate portions, non-arcuate shapes, a plurality of inwardly extending fingers, etc.).

FIGS. 20Cii-20Cviii are example expanded top views of a device for protecting a catheter interface. In FIG. 20Cii, the opening 1008d comprises a first arcuate portion 1008a and a second arcuate portion 1008b different than the first arcuate portion 1008a. For example, the first arcuate portion 1008a may be configured to receive a 5 Fr catheter and the second arcuate portion 1008b may be configured to receive a 3.5 Fr catheter, and/or a catheter may settle in the intersection or junction 1008j between the first arcuate portion 1008a and the second arcuate portion 1008b. In FIG. 20Ciii, the opening 1008e comprises a first arcuate portion 1008a, a second arcuate portion 1008b different than the first arcuate portion 1008a, and a third arcuate portion 1008c different than the first arcuate portion 1008a and the second arcuate portion 1008b. For example, the first arcuate portion 1008a may be configured to receive a 5 Fr catheter, the second arcuate portion 1008b may be configured to receive a 3.5 Fr catheter, and the third arcuate portion 1008c may be configured to receive a 2.5 Fr catheter, and/or a catheter may settle in the intersection or junction 1008j between the first arcuate portion 1008a, the second arcuate portion 1008b, and the third arcuate portion 1008c.

FIG. 20Civ illustrates an opening 1008f that can firmly accommodate two catheters of various sizes. The opening 1008f comprises a first arcuate portion 1008a and a second arcuate portion 1008b. The first arcuate portion 1008a comprises a first region 1008ai closest to the slot 1006, a second region 1008aii, and a third region 1008aiii each having different dimensions. For example, the first region 1008ai may be configured to receive a 5 Fr catheter, the second region 1008aii may be configured to receive a 3.5 Fr catheter, and the third region 1008aiii may be configured to receive a 2.5 Fr catheter. The second arcuate portion 1008b comprises a first region 1008bi closest to the slot 1006, a second region 1008bii, and a third region 1008biii each having different dimensions. For example, the first region 1008bi may be configured to receive a 5 Fr catheter, the second region 1008bii may be configured to receive a 3.5 Fr catheter, and the third region 1008biii may be configured to receive a 2.5 Fr catheter. The first arcuate portion 1008a and the second arcuate portion 1008b may be the same (e.g., as illustrated in FIG. 20Civ) or different (e.g., the first arcuate portion 1008a might consist essentially of the regions 1008ai, 1008aii and the second arcuate portion 1008b might consist essentially of the regions 1008bii, 1008biii). A catheter may settle in the intersection or junction 1008j between the first arcuate portion 1008a and the second arcuate portion 1008b.

FIG. 20Cv illustrates a T-shaped opening 1008g including a first polygonal portion 1008a, a second polygonal portion 1008b, and a junction 1008j between the first polygonal portion 1008a and the second polygonal portion 1008b. The polygonal portions 1008a, 1008b may be rectangular, square, triangular, hexagonal, octagonal, trapezoidal, etc. (e.g., accounting for sides that may not be present due to interaction with the slot 1006 or another polygonal portion). The polygonal portions 1008a, 1008b may comprise rounded corners. The T-shaped opening 1008g may be modified as described herein with respect to openings having arcuate portions (e.g., differently sized, a third polygonal portion, etc.). Combinations of polygonal portions and arcuate portions are possible.

FIG. 20Cvi illustrates an opening 1008h including a first polygonal portion 1008a, a second polygonal portion 1008b, and a junction 1008j between the first polygonal portion 1008a and the second polygonal portion 1008b. The polygonal portions 1008a, 1008b are shaped like parallelograms or rhombi having at least one corner with an angle less than 900 (e.g., about 15°, about 30°, about 45°, about 60°, about 75°, about 89°, ranges between such values, etc.). In some implementations, a catheter can be pulled against the acute corner and be at least partially stabilized by friction. A catheter may settle in the intersection or junction 1008j between the first polygonal portion 1008a and the second polygonal portion 1008b.

FIG. 20Cvii illustrates an opening 1008i including a first polygonal portion 1008a, a second polygonal portion 1008b, and a junction 1008j between the first polygonal portion 1008a and the second polygonal portion 1008b. The polygonal portions 1008a, 1008b are shaped like triangles having at least one corner with an angle less than 900 (e.g., about 15°, about 30°, about 45°, about 60°, about 75°, about 89°, ranges between such values, etc.). In some implementations, a catheter can be pulled against the acute corner and be at least partially stabilized by friction. A catheter may settle in the intersection or junction 1008j between the first polygonal portion 1008a and the second polygonal portion 1008b.

FIG. 20CViii illustrates an opening characterized by a slit 1008k that is an extension of the slot 1006, for example at least partially surrounded by flashing or other material. A catheter may be slid along the slot 1006 and into the slit 1008k, and the flashing or other material can provide friction to at least partially stabilize the catheter. Other openings described herein may include flashing or other material.

FIG. 20D is a top and back view of the device 1000. The of FIG. 20D helps to illustrate an example shape of the clips 1018 having a rounded rectangular outer surface and a smaller inner surface configured to allow a catheter to be wound at least partially under the outer surface. In some embodiments, the inner surface may be smaller than the outer surface in all directions to allow a catheter to be wound at least partially under the outer surface in any direction. In some embodiments, the inner surface may be smaller than the outer surface in only some directions (e.g., upper and lower, but not side). For example, such an arrangement can direct a catheter to be wound at least partially under the outer surface in those directions, can provide undercuts for positioning of a catheter and enough material to form a strong junction between the clip 1018 and the shield 1002, and/or can allow tethers 1016 to extend substantially unimpeded. Shapes other than rounded rectangle are also possible (e.g., other polygons or rounded polygons, arcuate shapes, combinations thereof, and the like). The clips 1018 preferably include a surface having a shape configured to interact with a shape of a surface of a corresponding latch 1014 (e.g., flat-flat, arcuate-arcuate, angled-angled, etc.). The surfaces of the clip 1018 may be dimensioned so that an umbilical catheter (e.g., between about 2.5 Fr and about 5 Fr) can be secured (e.g., mechanically and/or frictionally grasped by the surfaces of the clip 1018) and/or can be wound at least partially around the clip 1018 without kinking. Certain shapes of the clip 1018, such as rectangular, can help to be able to pull a latch 1014 around the clip 1018. The clips 1018 can used to manipulate the device 1000. For example, the clips 1018 can be pinched together to provide one-handed opening of the slot 1006. The space between the clips 1018 may be less prone to deformation than other portions of the device 1000 (e.g., proximate to the slot 1006).

FIG. 20E is a front view of the device 1000. FIG. 20Fi is a side view of the device 1000. FIG. 20Fii is an expanded side view of the device 1000 in the area of the circle 20Fii of FIG. 20Fi. The device 1000 includes vents 1004 extending through the shield 1002. For example as described herein, the vents 1004 extend through the shield to allow communication of fluid (e.g., air) in and out of the shield 1002, which can inhibit or prevent a "bio-dome" like effect. In some embodiments, one or more or all of the vents 1004 may be partially or fully covered by a semipermeable membrane. In the device 1000 illustrated in FIGS. 20Ai-20Fii, six oblong vents 1004 extend about 180° about the circumference of the shield 1002. Other quantities, shapes, circumferential extension, and/or distribution are also possible. For example, the shield may comprise between 1 vent and 30 vents (e.g., 1 vent, 2 vents, 3 vents, 4 vents, 5 vents, 6 vents, 7 vents, 8 vents, 9 vents, 10 vents, 12 vents, 15 vents, 20 vents, 25 vents, 30 vents, ranges between such values, and the like). Depending on size, more than 30 vents is also possible. For another example, the vents 1004 may extend more or less than 180° about the circumference of the shield 1002. For another example, the vents 1004 may comprise different shapes (e.g., circular, egg-shaped, oval, ellipsoid, polygonal, rounded polygonal, combinations thereof, and the like). Shapes without sharp corners may be more conducive to certain molding processes. For another example, the vents 1004 may or may not be distributed evenly (e.g., there may be more vents on one side of a plane bisecting the shield 1002 than on the other side of the plane).

As best seen in FIGS. 20E and 20Fi, in the device 1000 illustrated in FIGS. 20Ai-20Fii, the oblong vents 1004 vary in size. The vents 1004 distant to the flanges 1010 are longer than the vents 1004 proximate to the flanges 1010. In some embodiments, the vents 1004 may have the same size. In some embodiments, the device 1002 may comprise pinching protrusions circumferentially aligned with the flanges 1010 (e.g., as generally illustrated in FIGS. 19A and 19B). In certain such embodiments, vents 1004 between the flanges 1010 and the pinching protrusions may be shorter than the vents 1004 above the flanges 1010 depicted in FIGS. 20Ai-20Fii. In some embodiments, these vents 1004 can be designed to aid in the pinching action. The vents 1004 can have the same length and staggered heights (e.g., to accommodate surrounding structures). The vents 1004 can have different lengths and staggered heights (e.g., to accommodate surrounding structures). In some embodiments, the vents 1004 can facilitate viewing of an umbilical stump and/or catheter indicia in the cavity 1001. In some embodiments, the vents 1004 on one side of the slot 1006 have different shapes, sizes (e.g., area, length, width), starting heights, ending heights, or other parameters (e.g., to accommodate surrounding structures), and the vents 1004 on the other side of the slot 1006 are substantially mirror images of the vents 1004 on the one side of the slot 1006. If the device 1000 is molded, flashing is preferably removed from the vents 1004 to ensure that the vents 1004 are able to provide the fluid communication. For example, flash may be less than about 1 mm, more preferably less than about 0.5 mm, and even more preferably than about 0.3 mm.

In some embodiments, the vents 1004 have a combined surface area between about 0.25 $cm^2$ and about 3 $cm^2$ (e.g., about 0.25 $cm^2$, about 0.5 $cm^2$, about 0.75 $cm^2$, about 1 $cm^2$, about 1.25 $cm^2$, about 1.5 $cm^2$, about 2 $cm^2$, about 2.5 $cm^2$, about 3 $cm^2$, ranges between such values, and the like). The combined surface area of the vents 1004 may vary, for example, based on the size of the device 1000. In some embodiments, a ratio of the combined surface area of the vents 1004 to the surface area of the shield 1002 (e.g., excluding protruding features such as the flanges 1010 and the clips 1018) is between about 1:10 and about 1:2 (e.g., about 1:10, about 1:7, about 1:5, about 1:4, about 1:3, about 1:2, ranges between such values, and the like). In some embodiments, a combined surface area of the vents 1004 as a percentage of the total surface area of the shield 1002 (e.g., excluding protruding features such as the flanges 1010 and the clips 1018) is between about 9% and about 33% (e.g., about 9%, about 14%, about 17%, about 20%, about 25%, about 33%, ranges between such values, and the like).

The vents 1004, as with certain other vents described herein, are not configured to prevent air-borne debris, bacteria, etc. from entering the cavity 1001. The device 1000 is placed in a sterile field, optionally as part of a sterile kit, and neonatal intensive care units, for example, typically to not have a large amount of air-borne debris, bacteria, etc. On a first level, the device 1000 is configured to inhibit or prevent large objects such as blankets, nurse fingers, and the like from irritating the catheter interface. For example, the vents 1004 may be large enough to inhibit or prevent a bio-dome effect but small enough to inhibit or prevent large objects such as blankets, nurse fingers, and the like from touching the catheter interface and/or the umbilical stump. In the event of a diaper leak, a nurse sneeze, etc., the device 1000 may optionally be disconnected from the catheter and cleaned or replaced, then the cleaned device 1000, new device 1000, or another protective device can be positioned. In some embodiments, the device 1000 may be advantageously easily disconnected from the catheter, for example to reposition the catheter (e.g., to account for subject growth), and easily reconnected from the catheter. In some embodiments, for example a shield 1002 comprising silicone, the shield 1002 is resistant to bacterial growth and/or migration, so bacteria are inhibited or prevented from migrating along the skin and into the cavity 1001 of the shield 1002. In some embodiments, the shield 1002 does not include an added antimicrobial agent. In some embodiments, the shield 1002 comprises an added antimicrobial agent (e.g., chlorhexidene, silver salt, etc.). The shield 1002 is configured to surround and be spaced from a catheter interface when a catheter interface is in the cavity 1001. Portions of the shield do not contact areas immediately surrounding the catheter interface, but are spaced from the catheter interface by a distance. In some embodiments, the distance is at least 0.5 cm, at least 1 cm, at least 2 cm, up to about 3 cm or more, depending for example on the interface and the subject.

The device 1000 includes two flanges 1010 extending laterally outwardly from the shield 1002. The flanges 1010 optionally include adhesive and/or adhesive tape on a bottom side. The addition of adhesive or adhesive tape would not affect the characterization of the flanges 1010 being monolithically formed with the other features of the device 1000. The flanges 1010 are preferably large enough to provide surface area that inhibits or prevents movement of the device 1000 relative to the subject. Flanges 1010 being on opposing sides can help to inhibit or prevent movement in response to forces in multiple directions. For example, one flange 1010 might be relatively easily dislodged by an upward force on the shield 1002 whereas two flanges 1010 together providing the same adhesive force may be more resistant to such a force by being on opposite sides. In some embodiments, the device 1000 comprises two flanges 1010 that are circumferentially spaced by between about 150° and about 180° (e.g., about 150°, about 160°, about 170°, about 180°, ranges between these values, and the like). In some embodiments, the device 1000 does not comprise material (e.g., other flanges) between the flanges 1010. In some embodiments, the device 1000 comprises three flanges 1010 that are circumferentially spaced by between about 750 and about 1200 (e.g., about 75°, about 90°, about 105°, about 120°, ranges between these values, and the like). For example, a third flange 1010 may extend laterally outward from the slot 1006. Such a flange 1010 may include an extension of the slot 1006 or be slightly circumferentially displaced from the slot 1006. For another example, a third flange 1010 may extend laterally outward opposite the slot 1006. In some embodiments, the device 1000 comprises four flanges 1010 that are circumferentially spaced by between about 300 and about 90° (e.g., about 30°, about 45°, about 60°, about 75°, about 90°, ranges between these values, and the like). In some embodiments, the flanges 1010 could comprise a lip extending radially outward from the shield 1002, for example as illustrated by the base 40 in FIG. 1. Such a lip may be fully or partially annular. The lip may comprise a plurality of annular features. In some embodiments, the flanges 1010 may comprise a textured upper surface, for example to increase surface area for interaction with securement tape. Texture may be added during forming (e.g., as a feature of a mold) and/or after forming (e.g., by etching, cutting, etc.).

FIG. 201 is a cross-sectional view of an example device 1070 interacting with a subject 1072. The cross-section is taken below the edge of the device 1070 transverse to the subject. The device 1070 comprises flanges 1074 that are relatively long and flexible. The flanges 1074 are configured to wrap around the back of the subject 1072. In certain such embodiments, the flanges 1074 may be configured to interact with each other (e.g., to be coupled to each other such as via adhesive, clip, hook-and-loop fastener, knot, magnets, combinations thereof, etc.) to secure the device 1070 to the subject. Flanges 1074 that can be coupled to each other can inhibit or reduce or prevent the use of adhesive between the device 1070 and the subject 1072. Reducing the use of adhesive to the skin can reduce skin irritation due to adhesive, due to removal of adhesive, and/or other potential issues associates with adhesive. In some embodiments, one of the flanges 1074 (e.g., the flange 1074a) may be longer than the other flange 1074 (e.g., the flange 1074b). In some embodiments, flexibility of the flanges 1074 allows the flanges to flex during movement of the subject including breathing and other movements that may changes the size and/or shape around the umbilical stump. In some embodiments, the device 1070 may comprise a single flange 1074 having a first end coupled or configured to be coupled to the shield and/or a protrusion therefrom and a second end coupled or configured to be coupled to the shield and/or a protrusion therefrom.

FIG. 20Fiii is a cross-sectional view of the device 1000 of FIG. 20Ai taken along the line 20Fiii-20Fiii of FIG. 20D. The cross-section is taken vertically and perpendicular to a major axis of a flange 1010 or parallel to a minor axis of the flange 1010. In some embodiments, the flange 1010 has a cross-sectional profile including a rounded upper surface and a flat bottom surface, for example like a speed bump or speed hump. Rounded surfaces can reduce sharp edges, which can make the flanges 1010 softer.

FIGS. 20Fiv and 20Fv schematically illustrate a cross-sectional side views of tape 1050 interacting with a flange. In FIG. 20Fiv, the flange 1010 has the cross-sectional profile discussed above. The tape 1050 is able to abut most or all of the upper surface of the flange 1010 such that the gap 1052 between the tape 1050 and the flange 1010 is small or eliminated. By contrast, in FIG. 20Fv, the flange 1011 (e.g., of a different device or a modified version of the device 1000) has a squared cross-sectional profile. The tape 1050 is able to abut the upper surface of the flange 1011 well, but large gap 1052 are created lateral to the upper surface. Because the tape is not adhered at the gap 1052, reducing the gap 1052 can reduce an adhesion failure point such that the flanges 1010 are less likely to move and/or be lifted. Less force may be used to create a suitable seal because application force may be reduced with a smaller gap 1052, which can provide for a better seal and/or less trauma on the subject. A smaller gap 1052 can reduce a bacterial build-up site. Other shapes may also provide smaller gaps, for example polygons (e.g., trapezoids) with rounded corners.

The device 1000 includes anchors 1012 extending upward from the flanges 1010. In implementations in which a bandage, suture, etc. is placed over the flanges 1010, the anchors 1012 can inhibit or prevent the bandage, suture, etc. from sliding radially outward off the flanges 1010. In some embodiments, the anchors 1012 can provide grasping points for leveraged removal of the flanges 1010 and thereby the device 1000.

FIG. 20G is a top view of an example implementation of the device 1000 of FIG. 20Ai. The device 1000 is positioned with the latches 1014 facing away from a diaper 1062. Pieces of tape 1060 are attached across the flanges 1010 in a head-toe orientation, which is a form factor that may advantageously be familiar to a user of tape-bridge devices. Such an orientation can provide a user with room to use or adjust the latches 1014 away from the diaper 1062. In some implementations, the device 1000 may be rotated 180° versus FIG. 20G, for example so the vents 1004 are facing away from the diaper 1062. The anchors 1012 inhibit or prevent the tape 1060 from sliding off radially outward, as certain adhesives do not adhere well to certain materials of the flanges 1010. The anchors 1012 can help guide a user to position the tape 1060 close to the shield 1002, which can increase stability of the device 1000, which can increase protection of the umbilical stump. The tethers 1016 or the latches 1014 may be shaped and/or dimensioned such that the pieces of tape 1060 are not obstructed by the tethers 1016 or the latches 1014, as seen by the lack of overlap. The pieces of tape 1060 preferably do not obstruct the upper surface 1003 of the shield 1002, which can reduce interference with visibility of umbilical stump condition and/or interference with visibility of catheter position. As discussed herein, the device 1000 may be packaged with a kit that includes pieces of tape 1060 having appropriate dimensions. In some implementations, the pieces of tape may be at an angle (e.g., following the contours of the shield 1002. In certain such implementations, the anchors 1012 may be angled to guide the user.

FIG. 20Hi is an expanded top view of the device 1000 in the area of the circle 20Hi of FIG. 20Bii. The area of the circle 20Hi in FIG. 20Bii includes a latch 1014, tethers 1016, and a clip 1018. Referring again to FIG. 20Fi, one of the tethers 1016 may have a thickness 1028 (e.g., diameter) between about 0.5 mm and about 3 mm (e.g., about 0.5 mm, about 1 mm, about 1.5 mm, about 2 mm, about 2.5 mm, about 3 mm, ranges between such values, and the like). One of the tethers 1016 may have a width 1030 (e.g., diameter) between about 0.5 mm and about 3 mm (e.g., about 0.5 mm, about 1 mm, about 1.5 mm, about 2 mm, about 2.5 mm, about 3 mm, ranges between such values, and the like). One of the tethers 1016 may have a width 1032 (e.g., diameter) between about 0.5 mm and about 3 mm (e.g., about 0.5 mm, about 1 mm, about 1.5 mm, about 2 mm, about 2.5 mm, about 3 mm, ranges between such values, and the like). The widths 1030, 1032 may be the same or different. For example, different widths can provide different elasticity, which may bias the latch 1014 in a certain direction. The expanded top view of FIG. 20Hi shows a difference in dimensions of the clip 1018 that can allow interaction with an umbilical catheter as described herein. For example, the clip 1018 can have a lateral width 1034 between about 5 mm and about 10 mm (e.g., about 5 mm, about 5.5 mm, about 6 mm, about 6.5 mm, about 7 mm, about 7.5 mm, about 8 mm, about 8.5 mm, about 9 mm, about 9.5 mm, about 10 mm, ranges between such values, and the like).

If the device 1000 is molded, flashing is preferably removed from the tethers 1016 and the clip 1018 to ensure that the latching mechanism is able to latch. For example, flash may be less than about 1 mm, more preferably less than about 0.5 mm, and even more preferably than about 0.3 mm.

FIG. 20Hii is a cross-sectional view of the device 1000 along the line 20Hii-20Hii in FIG. 20Bii. The thickness of the upper surface 1003 of the shield 1002 is between about 0.3 mm and about 1 mm (e.g., about 0.3 mm, about 0.4 mm, about 0.5 mm, about 0.6 mm, about 0.7 mm, about 0.8 mm, about 0.9 mm, about 1 mm, ranges between these values, and the like). Different thicknesses may be appropriate for different materials. For example, some materials may start to lose sufficient transparency greater than a certain thickness.

FIG. 20Hiii is an expanded cross-sectional view of the device 1000 in the area of the circle 20Hiii of FIG. 20Hii. FIG. 20Hiii provides some example dimensions for grooves or areas between inner and outer surfaces of a clip 1018. For example, a clip 1018 may have a first (e.g., upper) groove thickness 1038 between about 1 mm and about 3 mm (e.g., about 1 mm, about 1.5 mm, about 2 mm, about 2.5 mm, about 3 mm, ranges between these values, and the like) and a second (e.g., lower) groove thickness 1040 between about 0.3 mm and about 1 mm (e.g., about 0.3 mm, about 0.4 mm, about 0.5 mm, about 0.6 mm, about 0.7 mm, about 0.8 mm, about 0.9 mm, about 1 mm, ranges between these values, and the like). Different thicknesses 1038, 1040 can provide flexibility in use of the clip 1018. For example, a catheter can be wound at least partially under the clip 1018 and the thickness 1040 can provide frictional engagement with the catheter and/or the catheter can be wound at least partially over the clip 1018 and the thickness 1038 can provide latching interaction so that the catheter is secured between the clip 1018 and the latch 1014. In some embodiments, the thicknesses 1038, 1040 may be substantially the same.

The tethers 1016 have a thickness 1031 in a dimension substantially perpendicular to the dimensions 1030, 1032. Dimensions of the tethers 1016 can affect performance. For example, a thicker cross-sectional area of a tether 1016, indicative of more material, can provide increased force for catheter retention when the tether 1016 is stretched by positioning a latch 1014 around a clip 1018. Such forces should not be so high that the forces to appropriately stretch the tether 1016 might damage and/or cause disruption of other aspects of the device 1000 (e.g., pulling the device 1000 off a subject). In some embodiments, the vertical dimension 1031 is less than the lateral dimension 1030, 1032. The lateral dimension 1030, 1032 can be indicative of a surface area available for frictional engagement with a catheter, providing a more secure connection. The vertical dimension 1031 can be reduced when the lateral dimension is increased to maintain a cross-sectional area to provide appropriate retention force. A tether 1016 having a vertical dimension 1031 that is smaller than a lateral dimension 1030, 1032 can appear flat. A flat tether 1016 can have a reduced bend radius transverse to the longer sides, increasing frictional engagement with a catheter, providing a more secure connection. The use of elastic tethers 1016 can provide frictional forces to catheters having different sizes.

Larger clips 1018 may, for example, be stronger, more durable, and/or provide more surface area for interaction with a catheter. Smaller clips 1018 may, for example, allow a larger quantity of clips 1018. As described herein, sizing and design of undercuts for the clips 1018 can affect catheter securement and/or device 1000 performance. Larger undercuts may, for example, allow larger catheters and/or multiple windings of a catheter. Smaller undercuts may, for example, provide a stronger junction between the clip 1018 and the shield 1002.

Undercuts may be the same or different or even non-existent in different directions. In some embodiments, an undercut (e.g., on a bottom of the clip 1018) may be configured to accommodate a catheter having a diameter between about 2.5 Fr and about 5 Fr. In some embodiments, an undercut (e.g., on a bottom of the clip 1018) may taper to a point or to a width less than the diameter of a 2.5 Fr catheter (e.g., less than about 0.75 mm). Such an undercut can provide flexibility to grasp a catheter and securely hold the catheter. In some embodiments, an undercut (e.g., on a bottom of the clip 1018) is configured to accommodate or fit one catheter, two catheters, or one catheter wrapped under the clip 1018 twice. In some embodiments, an undercut (e.g., on a top of the clip 1018) is configured to accommodate or fit one catheter and a bottom portion of a tab 1014. The force applied to the tab 1014 by the tethers 1016 preferably does not kink or crush the catheter against the clip 1018.

A clip 1018 that is too thick in the up/down direction can increase the bend angle of a catheter and could risk reducing the contact area with the catheter, for example reducing frictional securement. Increasing the width in the left/right direction relative to the up/down thickness can reduce such effects, for example maintaining a low bend radius while increasing surface area contact.

A clip 1018 having straight lateral edges can help tethers 1016 to be positioned on either side of the clip 1018. A clip 1018 having straight lateral edges can increase manufacturability by reducing or eliminating undercuts and allowing for a two-part mold. A clip 1018 having straight lateral edges can provide a strong connection between the clip 1018 and the shield 1002. A clip 1018 having straight lateral edges can follow a form factor of the device 1000. Straight lateral edges can allow the tethers 1016 to be pulled over the clips 1018 without interfering with the clips 1018. Reducing or eliminating such interference can, for example make the latches 1014 easier to secure. Straight lateral edges can facilitate overall handling of the device 1000 by a user. For example, handling and/or gripping a device 1000 with flat surfaces with one hand or two fingers (e.g., a thumb and an index finger) can be easier than handling and/or gripping a device 1000 with rounded features with one hand or two fingers (e.g., a thumb and an index finger). Rounded features may allow or cause the fingers to slip. Straight lateral edges can facilitate pinching of the clips 1018 to open the device 1000 by widening the slot 1006 when applying the device 1000 around a catheter.

In some embodiments, the device 1000 comprises a shoulder 1037 between the upper surface 1003 and the undercut of the clip 1018. Recessing the undercut from the upper surface 1003 can inhibit or prevent a catheter positioned in the undercut from sliding over the upper surface 1003.

Figure 21A:
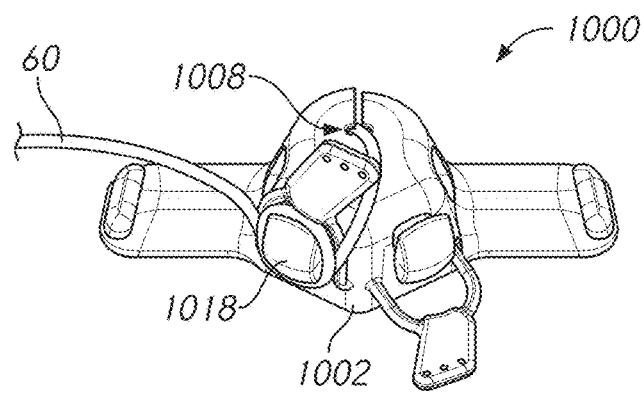
FIG. 21A is a top and back view of an example interaction between the device of FIG. 20Ai and a catheter.
Figure 21B:
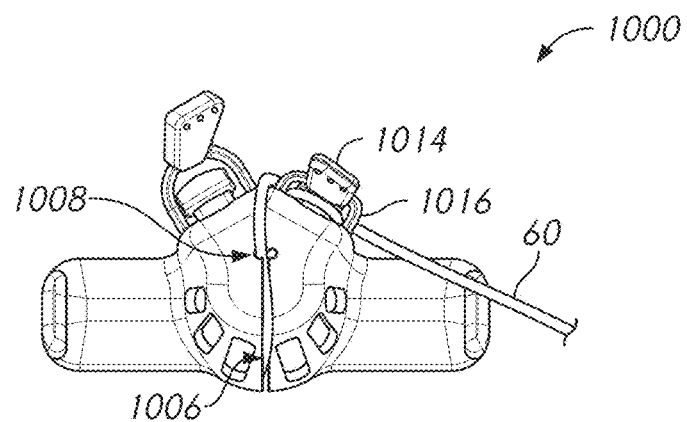
FIG. 21B is a top and front view of the example interaction of FIG. 21A between the device of FIG. 20Ai and a catheter.
Figure 21C:
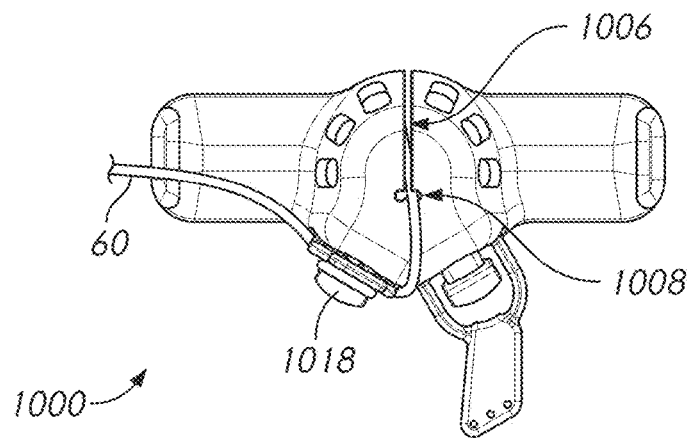
FIG. 21C is a top view of the example interaction of FIG. 21A between the device of FIG. 20Ai and a catheter.

FIG. 21A is a top and back view of an example interaction between the device 1000 and an umbilical catheter 60. FIG. 21B is a top and front view of the example interaction of FIG. 21A between the device 1000 and an umbilical catheter 60. FIG. 21C is a top view of the example interaction of FIG. 21A between the device 1000 and an umbilical catheter 60. The catheter 60 extends through the opening 1008 and then under the clip 1018. The latch 1014 is coupled to the clip 1018 (not visible). Each of the opening 1008 and the clip 1018 and/or the opening 1008 and the clip 1018 in combination can inhibit or prevent the catheter 60 from moving relative to the umbilical stump. As described herein (e.g., with respect to FIGS. 22A-22J), other interaction between the catheter 60 and the clip 1018 is also possible.

In some implementations, a method of positioning the device 1000 comprises positioning the umbilical catheter 60 through the slot 1006 so that the umbilical catheter 60 extends through the opening 1008. The opening 1008 may provide forces to at least partially maintain the position of the umbilical catheter 60 in the subject. The umbilical catheter 60 is then at least partially wound around a clip 1018. A latch 1014 is optionally coupled to the clip 1018. The inside surfaces of the tethers 1016 frictionally engage the umbilical catheter 60 and bear the umbilical catheter 60 against the outer surface of the shield 1002. At least four forces act to maintain the position of the umbilical catheter 60 in this implementation: (1) portions around the opening 1008 on the umbilical catheter 60; (2) bottom undercut of clip 1018 on the umbilical catheter 60; and (3) tethers 1016 and outside of shield 1002 on the umbilical catheter 60. Additional forces can be applied as desired, for example by implementing different interactions between the device 1000 and one or more umbilical catheters 60. In some embodiments, certain portions of the device 1000 (e.g., the undercuts of the clips 1018, the inside surfaces of the tethers 1016, the outside surface of the shield 1002 proximate the clips 1018) can include a textured surface configured to increase friction with a catheter. Texture may be added during forming (e.g., as a feature of a mold) and/or after forming (e.g., by etching, cutting, etc.).

Figure 22H:
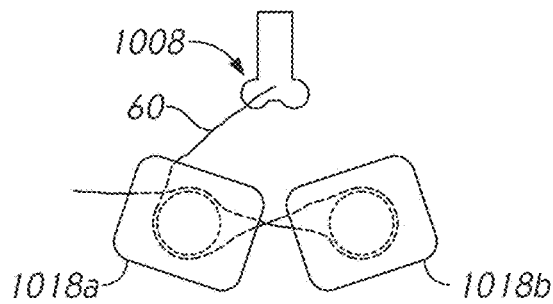

FIGS. 22A-22J illustrate example interactions between the device 1000 and one or more umbilical catheters 60. In FIG. 22A, the catheter 60 exits the opening 1008 and is wrapped under the clip 1018 (e.g., as shown in FIGS. 21A-21C). In FIG. 22B, the catheter 60 exits the opening 1008 and is wrapped under the clip 1018 then completely around the clip 1018. This implementation can add at least two additional forces compared to FIG. 22A: (4) top undercut of the clip 1018 on the umbilical catheter 60; and (5) latch 1014 pulled down by tethers 1016 against the umbilical catheter 60. This configuration has been sufficient to withstand all reasonable testing forces. FIG. 22C is similar to FIG. 22B, except the catheter 60 is wrapped around the clip 1018 in the opposite direction. Without being bound by any particular theory, it is believe that the number of times the catheter 60 changes direction has a relationship to the forces that can be applied to the catheter 60 (e.g., pulling on the part of the catheter 60 proximal to interaction with the device 1000) without the catheter 60 moving in the subject.

In embodiments comprising a plurality of clips 1018, one or more clips 1018 may be used. In FIG. 22D, the catheter 60 exits the opening 1008 and is wrapped under the first clip 1018*a* then under the second clip 1018*b*. In FIG. 22E, the catheter 60 exits the opening 1008 and is wrapped under the first clip 1018*a* then over the second clip 1018*b*. In FIG. 22F, the catheter 60 exits the opening 1008 and is wrapped under the first clip 1018*a*, then partially around the first clip 1018*a*, then under the second clip 1018*b*. In FIG. 22G, the catheter 60 exits the opening 1008 and is wrapped under the first clip 1018*a*, then partially around the first clip 1018*a*, then over the second clip 1018*b*. In FIG. 22H, the catheter 60 exits the opening 1008 and is wrapped under the first clip 1018*a*, then over the second clip 1018*b*, then partially around the second clip 1018*b*, then over the first clip 1018*a*.

Figure 22I:
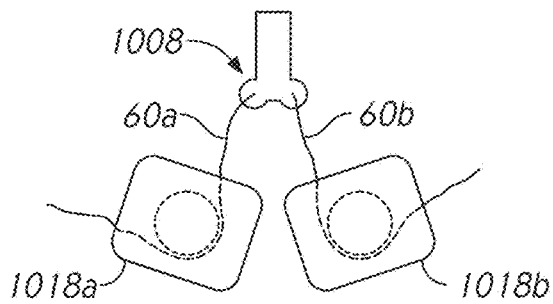
Figure 22J:
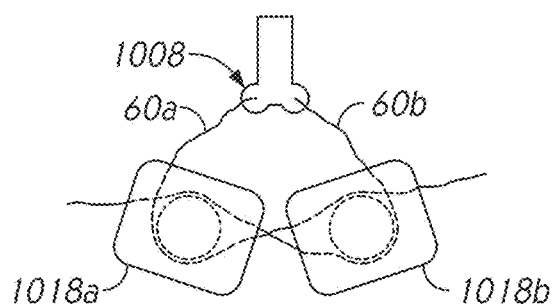
Figure 22K:
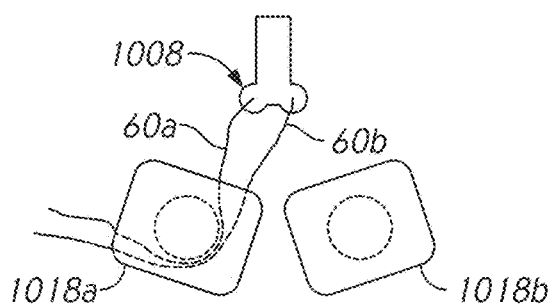

In embodiments comprising a plurality of clips 1018 and implementations using a plurality of catheters 60, each clip 1018 may be used for one or more different catheters 60. In FIG. 22I, the first catheter 60*a* exits the opening 1008 and is wrapped under the first clip 1018*a*, and the second catheter 60*b* exits the opening 1008 and is wrapped under the second clip 1018*b* (e.g., each clip 1018 is used for a different catheter 60). In FIG. 22J, the first catheter 60*a* exits the opening 1008 and is wrapped under the first clip 1018*a* then over the second clip 1018*b*, and the second catheter 60*b* exits the opening 1008 and is wrapped under the second clip 1018*b* then over the first clip 1018*a* (e.g., each clip 1018 is used for each catheter 60, or a catheter 60 interacts with multiple clips 1018). In FIG. 22K, the first catheter 60*a* exits the opening 1008 and is wrapped under the first clip 1018*a*, and the second catheter 60*b* exits the opening 1008 and is wrapped under the first clip 1018*a* (e.g., the same clip 1018*a* is used for different catheters 60 and the second clip 1018*b* is not used). As described herein, in some embodiments, a bottom undercut of a clip 1018 is configured to accommodate two catheters 60.

Figure 22L:
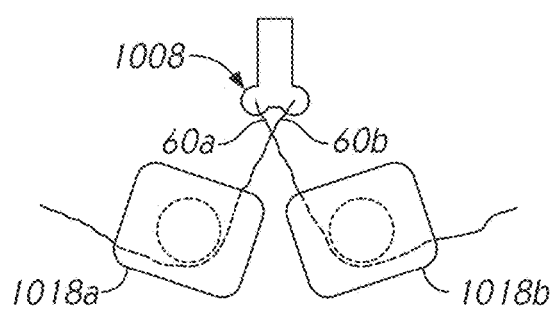
Figure 22M:
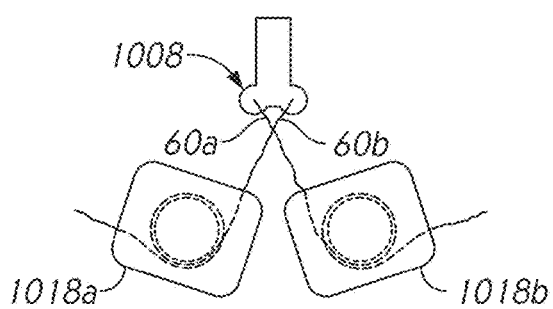

In FIG. 22L, the first catheter 60*a* exits the opening 1008 and is wrapped under the second clip 1018*b*, and the second catheter 60*b* exits the opening 1008 and is wrapped under the first clip 1018*a*. The catheters 60*a*, 60*b* cross compared to other implementations, which can provide a user more room to manipulate the catheters 60*a*, 60*b*. In FIG. 22M, the first catheter 60*a* exits the opening 1008 and is wrapped under the second clip 1018*b* then completely around the second clip 1018*b*, and the second catheter 60*b* exits the opening 1008 and is wrapped under the first clip 1018*a* then completely around the first clip 1018*a*. The implementation of FIG. 22M may be preferred for securement of the use of two catheters 60*a*, 60*b*.

In implementations using multiple catheters 60, the catheters may interact with specific portions of the opening 1008, for example snapping into arcuate portions as described herein.

Figure 22N:
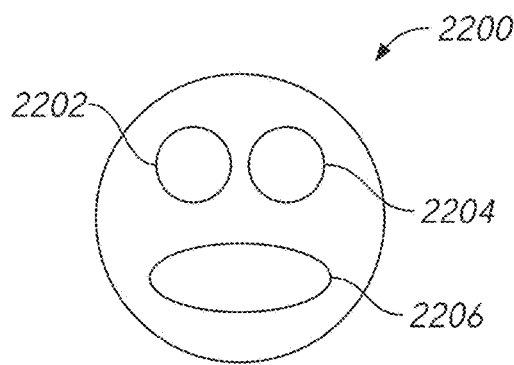
FIG. 22N is a schematic top view of a mammalian umbilical stump.

FIG. 22N is a schematic top view of a mammalian umbilical stump 2200. The stump 2200 comprises a first arterial port 2202, a second arterial port 2204, and a venous port 2206. In some implementations, a single umbilical catheter 60 is used in the venous port 2206. In some implementations, a single umbilical catheter 60 is used in the first arterial port 2202 or the second arterial port 2204. In some implementations, a first umbilical catheter 60 is used in the venous port 2206 and a second umbilical catheter 60 is used in the first arterial port 2202 or the second arterial port 2204. In some implementations, a first umbilical catheter 60 is used in the first arterial port 2202 and a second umbilical catheter is used in the second arterial port 2204. In some implementations, a first umbilical catheter 60 is used in the venous port 2206, a second umbilical catheter 60 is used in the first arterial port 2202, and a third umbilical catheter 60 is used in the second arterial port 2204. In implementations using a single catheter 60, the implementations illustrated in FIGS. 22A-22H, for example, may be used. In implementations using a plurality of catheters 60, the implementations illustrated in FIGS. 22I-22M, for example, may be used.

Figure 23A:
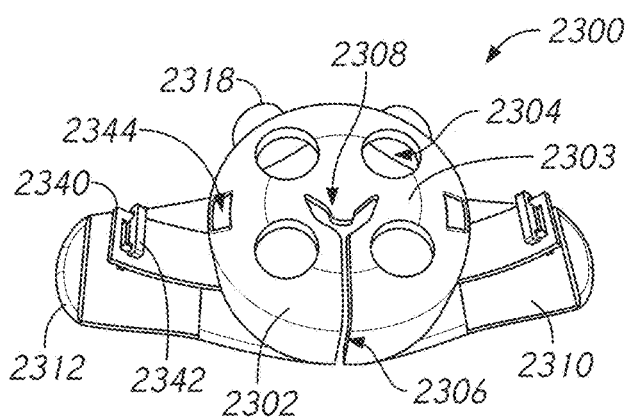
FIG. 23A is a top and front view of another example device for protecting a catheter interface.

FIG. 23A is a top and front view of another example device 2300 for protecting a catheter interface. The device 2300 can comprise features of the device 1000 and/or other devices described herein. For example, the device 2300 comprises an upper surface 2303 having an opening 2308 similar to the opening 1008*h* of FIG. 20Cvi. The device 2300 also includes a shield 2302, vents 2304, a slot 2306, flanges 2310, anchors 2312, and clips 2318. The flanges 2310 comprise a track for placement of tape over the flanges 2310. One side of the tracks is at least partially defined by the anchors 2312. The device 2300 comprises strap 2340 including a fastener 2342 configured to fit into an opening 2344. A vent 2304 may comprise the opening 2344.

Figure 23B:
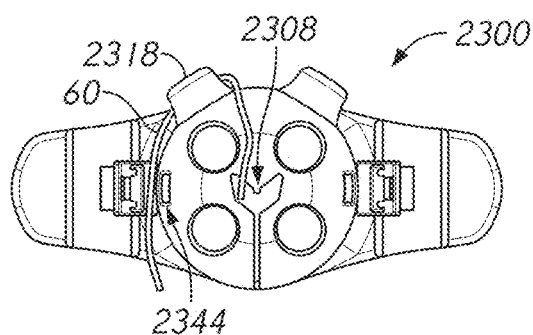
FIG. 23B is a top view of the device of FIG. 23A interacting with a catheter.
Figure 23C:
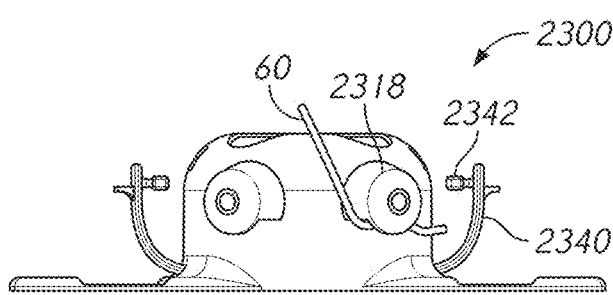
FIG. 23C is a back view of the device of FIG. 23A interacting with a catheter.
Figure 23D:
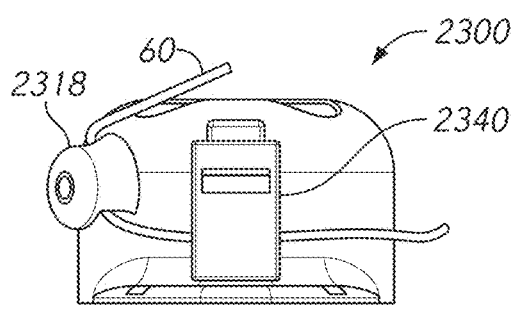
FIG. 23D is a side view of the device of FIG. 23A interacting with a catheter.
Figure 23E:
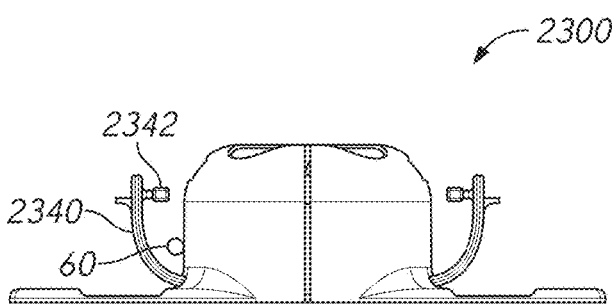
FIG. 23E is a front view of the device of FIG. 23A interacting with a catheter.

FIGS. 23B-23E illustrate an example implementation of the device 2300 interacting with a catheter 60. FIG. 23B is a top view; FIG. 23C is a back view; FIG. 23D is a side view; and FIG. 23E is a front view. As best seen in FIG. 23B, the catheter 60 exits the opening 2308. The catheter 60 can be biased to one side of the opening 2308, which can increase engagement of the opening 2308 and the catheter 60, and/or which can guide the catheter 60 towards a particular clip 2318. The opening 2308 can provide friction at the exit point parallel to the umbilical stump. After exiting the opening 2308, the catheter 60 changes direction towards the bottom of the device 2300. As best seen in FIG. 23C, the catheter 60 wraps under an undercut in the clip 2318, changing direction a second time.

The catheter 60 may optionally be secured under the strap 2340. As shown in FIGS. 23B-23D, the catheter 60 can be positioned between the strap 2340 and the shield 2302. The fastener 2342 may optionally be inserted into the opening 2344. The strap 2340 may deform to accommodate different sizes of catheter 60, multiple windings of catheter 60, etc. The strap 2340 and the shield 2302 frictionally engage the catheter 60. A wider strap 2340 can provide more frictional engagement. In some embodiments, a width of the strap 2340 is independent of a size of the fastener 2342. The strap's material properties are specifically selected to achieve the desired function, for example as described herein with respect to properties such as tensile strength, elongation ability, surface friction, refractive index, and rate of change upon sterilization.

In some embodiments, the device 2300 may comprise a plurality of materials. For example, the shield 2302 and the flanges 2310 may comprise a first material, and the clips 2318, the straps 2340, and the fasteners 2342 may comprise a second material different than the first material. The second material may be more rigid than the first material. In certain such embodiments, the flexibility of the opening 2344 and the rigidity of the fastener 2342 may aid insertion of the fastener 2342 into the opening 2344 by deforming the opening 2344. The clip 2318 may be rigid (e.g., compared to the shield 2302), which can help to secure the catheter 60 when pulling the catheter 60 around the clip 2318. The first material and the second material may be joined by two-shot molding, coupling methods (e.g., welding, heat staking, adhesive), and the like.

Referring again to FIG. 23A, certain parts of the device 2300 may be different colors. For example, a first color such as blue can indicate interaction with a venous catheter and a second color such as orange or red can indicate interaction with an arterial catheter. Color may be integrated into the material and/or applied after forming the device (e.g., via decals, paint, dye, etc.).

Figure 24A:
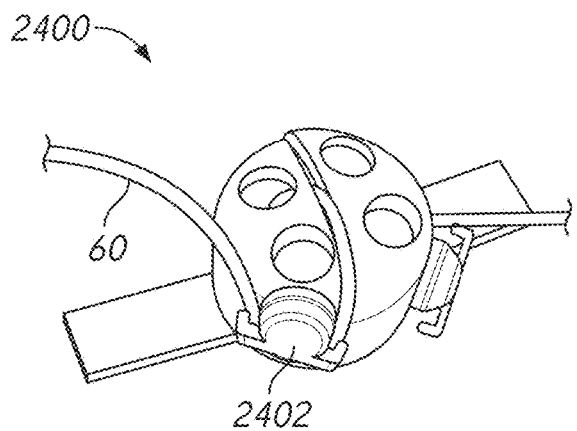
FIG. 24A is a top, back, and side view of another example device for protecting a catheter interface.

FIG. 24A is a top, back, and side view of another example device 2400 for protecting a catheter interface. The device 2400 comprises a clip 2402 having side undercuts for securing a catheter 60. The catheter 60 exits the opening, which can provide friction at the exit point roughly or substantially parallel to the umbilical stump. After exiting the opening, the catheter 60 changes direction towards the bottom of the device 2400. The catheter 60 extends through a first undercut on a side of the clip 2402, under the clip 2402, changing direction a second time, and then through a second undercut on a second side of the clip 2402. The device 2400 may include tethers and latches. For example, the tethers may extend circumferentially.

Figure 24B:
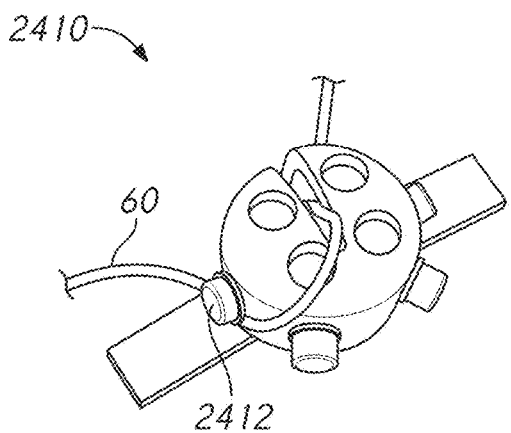
FIG. 24B is a top, back, and side view of another example device for protecting a catheter interface.

FIG. 24B is a top, back, and side view of another example device 2410 for protecting a catheter interface. The device 2410 comprises a clip 2412 having a bottom undercut. The undercut may be roughly shaped as a hook. Referring again to the clips 940, the undercut cavity may be configured to frictionally engage the catheter 60. The device 2410 illustrated in FIG. 24B includes four clips 2412. More than one clip 2412 can be used to secure a single catheter 60.

Figure 24C:
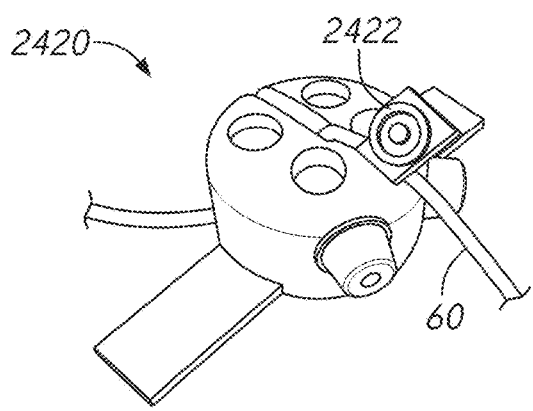
FIG. 24C is a top, back, and side view of another example device for protecting a catheter interface.

FIG. 24C is a top, back, and side view of another example device 2420 for protecting a catheter interface. The device 2420 comprises a snap 2422 configured to be positioned around the catheter 60 to secure the catheter 60. The snap 2422 may comprise a rigid or semi-rigid material that allows the snap 2422 to be opened and closed by a user. The snap 2422 may comprise a compliant material that conforms around the catheter to increase surface area and thus friction for more effectively securing the catheter.

Figure 24D:
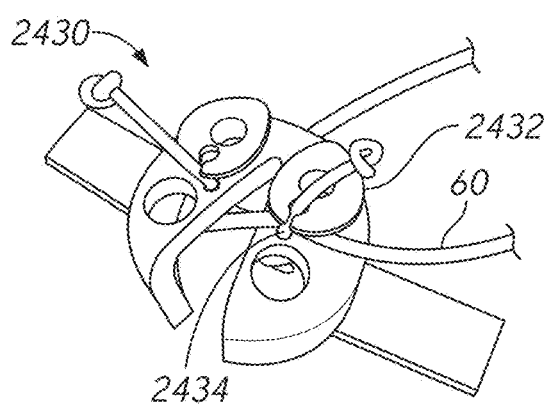
FIG. 24D is a top, back, and side view of another example device for protecting a catheter interface.

FIG. 24D is a top, back, and side view of another example device 2430 for protecting a catheter interface. The device 2430 comprises a clip 2432 having an opening configured to accept a plug 2434. A catheter 60 may be placed under an undercut of the clip 2432. The undercut may be roughly shaped as a hook. The plug 2434, for example comprising a cable anchored to the shield and including a knot for easier grasping, may be snapped into the opening of the clip 2432. The plug 2434 may inhibit the catheter 60 from migrating out of the clip 2432. The plug 2434 may frictionally engage the catheter 60. In some embodiments, the clips 2432 are modular and configured to be positioned in a vent, providing flexibility about positioning of the clip 2432.

Figure 24E:
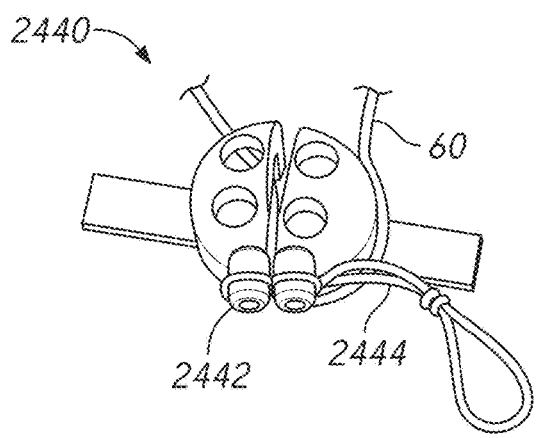
FIG. 24E is a top, back, and side view of another example device for protecting a catheter interface.

FIG. 24E is a top, back, and side view of another example device 2440 for protecting a catheter interface. The device 2440 comprises a clip 2442 with two rigid or semi-rigid features having an interior opening between the two rigid or semi-rigid features. A catheter 60 may be placed in the interior opening and then under a portion of the clip 2442. A strap 2444 may be positioned around the clip 2442 to secure and tighten the junction to at least partially close the interior opening. The strap 2444 may be elastic or longitudinally rigid. The strap 2444 may be coupled to the device 2440 or separate from the device 2440.

Figure 24F:
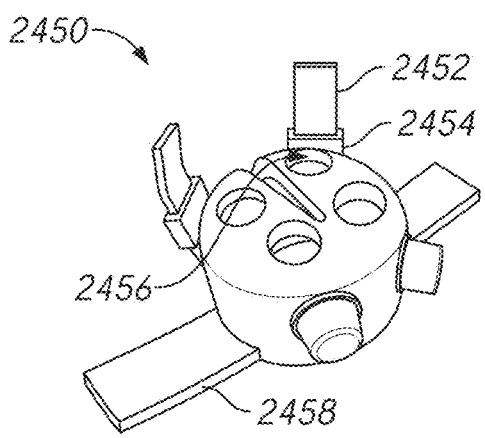
FIG. 24F is a top, back, and side view of another example device for protecting a catheter interface.

FIG. 24F is a top, back, and side view of another example device 2450 for protecting a catheter interface. The device 2450 shares certain features with the device 2300. The device 2450 comprises a strap 2452 including a plug 2454 configured to fit into a vent 2456. In comparison to the device 2300, in which the straps 2342 are circumferentially aligned with the flanges 2310, the straps 2452 are not circumferentially aligned with the flanges 2458. Tape for securing the device 2450 to a subject may be easier to position over the flanges 2458 if the flanges 2458 are not obstructed by straps 2452. In comparison to the device 2300, in which the openings 2344 have a different size and shape than the vents 2304, the vents 2456 proximate the straps 2452 are configured to engage the plugs 2454. Integrating the openings into the vents 2456 can make manufacturing easier, for example because fewer holes are created and fewer small holes are created, each of which can present difficulties.

Figures 24G, 25A:
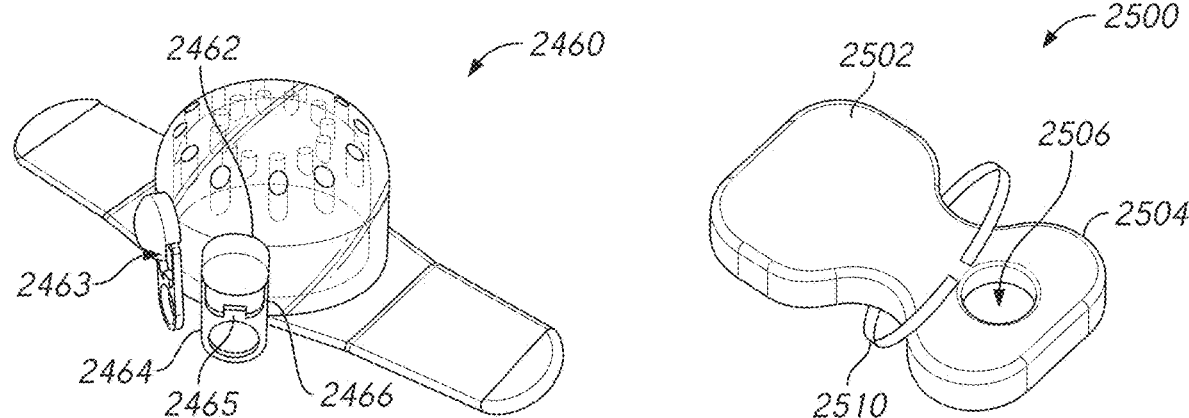
FIG. 24G is a top, back, and side view of another example device for protecting a catheter interface.
FIG. 25A is a top, front, and side view of an example device for positioning a subject in a prone position while a catheter interface is being protected by a device.

FIG. 24G is a top, back, and side view of another example device 2460 for protecting a catheter interface. The device 2460 comprises a clip 2462. The clip 2462 optionally comprises an undercut on a top side and/or a bottom side. The undercut may be roughly shaped as a hook. The clip 2462 may include features of the clip 1018. The device 2460 further comprises a latch 2464 coupled and tethers 2466. The latch 2464 includes a tab 2465 configured to interact with an undercut in a top of the clip 2462 and/or a catheter placed between the clip 2462 and the latch 2464 in a strapped position. The latch 2464 includes a circular opening to aid grip thereof. Other grip enhancing features are also possible (e.g., the protrusions 1015).

The features of the devices 2400, 2410, 2420, 2430, 2440, 2450, 2460 can be adapted for other devices described herein, and vice versa the features of other devices described herein can be adapted for the devices 2400, 2410, 2420, 2430, 2440, 2450, 2460. For example, the device 1000 may include clips 2402 having side undercuts, clips 2432 and plugs 2434, a tab 2465, etc.

FIG. 25A is a top, front, and side view of an example device 2500 for positioning a subject in a prone position while a catheter interface is being protected by a device. The device 2500 comprises a first padded area 2502 for the subject's head and torso and a second padded area 2504 for the subject's belly. The padded areas 2502, 2504 may be merged, and/or one or more padded areas can be provided for discrete body parts (e.g., for hips, legs, etc.). The device 2500 includes an opening 2506 configured to accommodate a catheter interface protection device. The opening 2506 may be a through-hole or a cavity. In some embodiments, the opening 2506 is dimensioned to accommodate a device as described herein. For example, the opening 2506 may have a depth into the padded area 2504 between about 1 cm and about 10 cm (e.g., about 1 cm, about 2 cm, about 3 cm, about 4 cm, about 5 cm, about 6 cm, about 7 cm, about 8 cm, about 9 cm, about 10 cm, ranges between such values, etc.). For another example, the opening 2506 may have a diameter between about 0.5 cm and about 10 cm (e.g., about 0.5 cm, about 1 cm, about 1.5 cm, about 2 cm, about 3 cm, about 4 cm, about 5 cm, about 6 cm, about 7 cm, about 8 cm, about 9 cm, about 10 cm, ranges between such values, etc.). The device 2500 may include one or more channels configured for routing of a catheter from the cavity 2506 to a lateral surface and/or an opposite surface of the device 2500. The device 2500 may or may not include a strap 2510 configured to wrap around the back of the subject. In some implementations, the strap 2510 may be configured to interact with itself (e.g., each end to be coupled to the other end, such as via adhesive, clip, hook-and-loop fastener, buckle, knot, ratchet, magnet, Velcro, combinations thereof, etc.). The strap 2510 may secure the device 2500 to the patient to ensure that the catheter interface protection device remains protected inside the opening 2506. The device 2500 allows a user to position the subject in a prone position (belly down) while alleviating force and stress to a secured umbilical catheter. This can reduce risk of catheter displacement while still protecting the insertion site (e.g., from bacteria on a bed).

Figure 25B:
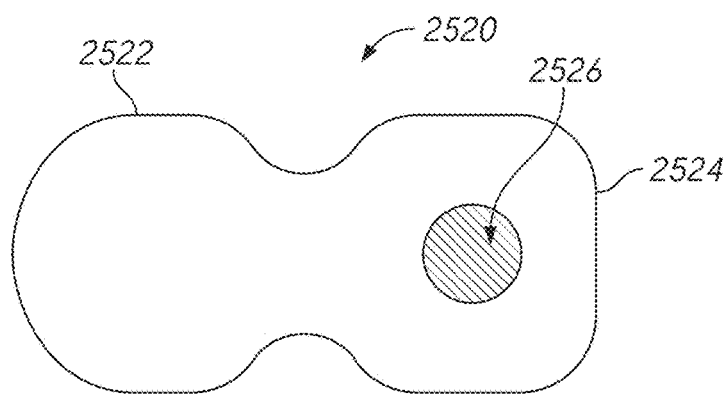
FIG. 25B is a top plan view of another example device for positioning a subject in a prone position while a catheter interface is being protected by a device.

FIG. 25B is a top plan view of another example device 2520 for positioning a subject in a prone position while a catheter interface is being protected by a device. The device 2520 comprises a first padded area 2522 for the subject's head and torso and a second padded area 2524 for the subject's belly. Compared to the first padded area 2502 of the device 2500, which is more rectangular, the first padded area 2522 of the device 2520 is rounder. Compared to the second padded area 2504 of the device 2500, which is more oblong, the first padded area 2522 of the device 2520 is more rectangular. Other shapes of the first padded area 2522 and/or the second padded area 2524 are also possible. The padded areas 2522, 2524 may be merged, and/or more padded areas can be provided for discrete body parts (e.g., for hips, legs, etc.). The device 2520 includes an opening 2526 configured to accommodate a catheter interface protection device. The opening 2526 may be a through-hole or a cavity. In some embodiments, the opening 2526 is dimensioned to accommodate a device as described herein. For example, the opening 2526 may have a depth into the padded area 2524 between about 1 cm and about 10 cm (e.g., about 1 cm, about 2 cm, about 3 cm, about 4 cm, about 5 cm, about 6 cm, about 7 cm, about 8 cm, about 9 cm, about 10 cm, ranges between such values, etc.). For another example, the opening 2526 may have a diameter between about 0.5 cm and about 10 cm (e.g., about 0.5 cm, about 1 cm, about 1.5 cm, about 2 cm, about 3 cm, about 4 cm, about 5 cm, about 6 cm, about 7 cm, about 8 cm, about 9 cm, about 10 cm, ranges between such values, etc.). The device 2520 may include one or more channels configured for routing of a catheter from the cavity 2526 to a lateral surface and/or an opposite surface of the device 2520. The device 2520 may include a strap (e.g., similar to the strap 2510). The device 2520 allows a user to position the subject in a prone position (belly down) while alleviating force and stress to a secured umbilical catheter. This can reduce risk of catheter displacement while still protecting the insertion site (e.g., from bacteria on a bed).

Figure 25C:
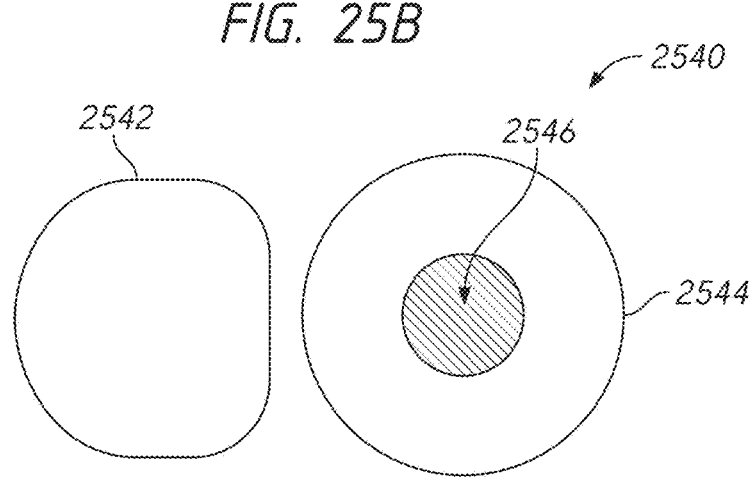
FIG. 25C is a top plan view of yet another example device for positioning a subject in a prone position while a catheter interface is being protected by a device.

FIG. 25C is a top plan view of yet another example device 2540 for positioning a subject in a prone position while a catheter interface is being protected by a device. The device 2540 comprises a first padded area 2542 for the subject's head and torso and a second padded area 2544 for the subject's belly. The first padded area 2542 may be separate from or discrete from the second padded area 2542. In certain such implementations, the first padded area 2542 may be tether or otherwise coupled or coupleable to the second padded area 2542, during use or storage. Compared to the first padded area 2502 of the device 2500, which is more rectangular, the first padded area 2542 of the device 2540 has one side that is rounder and another side that is generally flat, forming a D-shape. Compared to the second padded area 2504 of the device 2500, which is more oblong, the first padded area 2542 of the device 2540 is more rounded (e.g., donut-shaped). Other shapes of the first padded area 2542 and/or the second padded area 2544 are also possible. More padded areas can be provided for discrete body parts (e.g., for hips, legs, etc.). Such padded areas may be integral with or separate from the first padded area 2542 and/or the second padded area 2544. The device 2540 includes an opening 2546 configured to accommodate a catheter interface protection device. The opening 2546 may be a through-hole or a cavity. In some embodiments, the opening 2546 is dimensioned to accommodate a device as described herein. For example, the opening 2546 may have a depth into the padded area 2544 between about 1 cm and about 10 cm (e.g., about 1 cm, about 2 cm, about 3 cm, about 4 cm, about 5 cm, about 6 cm, about 7 cm, about 8 cm, about 9 cm, about 10 cm, ranges between such values, etc.). For another example, the opening 2546 may have a diameter between about 0.5 cm and about 10 cm (e.g., about 0.5 cm, about 1 cm, about 1.5 cm, about 2 cm, about 3 cm, about 4 cm, about 5 cm, about 6 cm, about 7 cm, about 8 cm, about 9 cm, about 10 cm, ranges between such values, etc.). The device 2540 may include one or more channels configured for routing of a catheter from the cavity 2546 to a lateral surface and/or an opposite surface of the device 2540. The device 2540 allows a user to position the subject in a prone position (belly down) while alleviating force and stress to a secured umbilical catheter. This can reduce risk of catheter displacement while still protecting the insertion site (e.g., from bacteria on a bed). The device 2540 comprising a plurality of pieces can accommodate a wide range of body shapes, sizes, weights, and/or ages, for example not assuming a certain distance between head and torso. The device 2540 comprising a plurality of pieces can allow for customization, for example each of the first padded area 2542 and the second padded area 2544 selected for length, width, thickness, and/or opening 2546 presence, size, and/or type, based on the subject. The device 2540 comprising a plurality of pieces can make manufacturing easier, for example to make each of the first padded area 2542 and the second padded area 2544 a different length, width, and/or thickness.

Figure 26A:
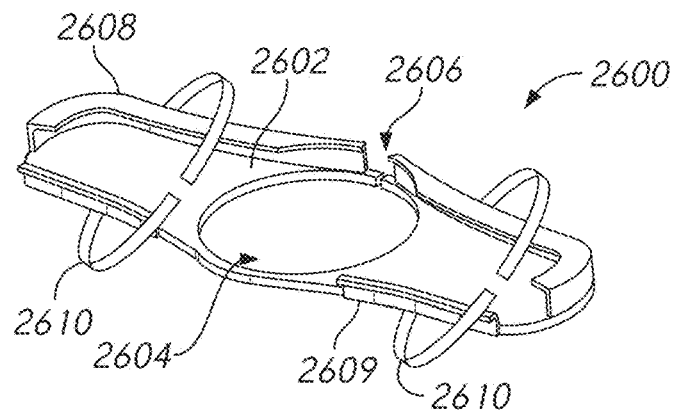
FIG. 26A is a top, front, and side view of a separate base structure for a device for protecting a catheter interface.

FIG. 26A is a top, front, and side view of a separate base structure 2600 for a device (e.g., the device 1000) for protecting a catheter interface. The base structure 2600 comprises a wings 2602 configured to be under flanges of a catheter interface protection device. The base structure 2600 comprises a hole 2604 so that the cavity of a catheter interface protection device can be positioned around an umbilical stump. The base structure 2600 optionally comprises a slot 2606, for example for catheter interface protection devices including a slot, although a base structure 2600 lacking a slot 2606 can be used with catheter interface protection devices including a slot. The base structure 2600 comprises a first lip 2608 on a first side of the wings 2602 and optionally a second lip 2609 on a second side of the wings 2602 opposite the first side. The first lip 2608 may include a shoulder extending inwardly to enhance interaction with a flange. The base structure 2600 may include straps 2610 that may be configured to interact with each other (e.g., to be coupled to each other such as via adhesive, clip, hook-and-loop fastener, buckle, knot, ratchet, Velcro, combinations thereof, etc.). An underside of the base structure 2600 may comprise adhesive. This adhesive may be hydrocolloid or silicone-based, for example to reduce or minimize skin irritation over an extended period of time.

Figure 26B:
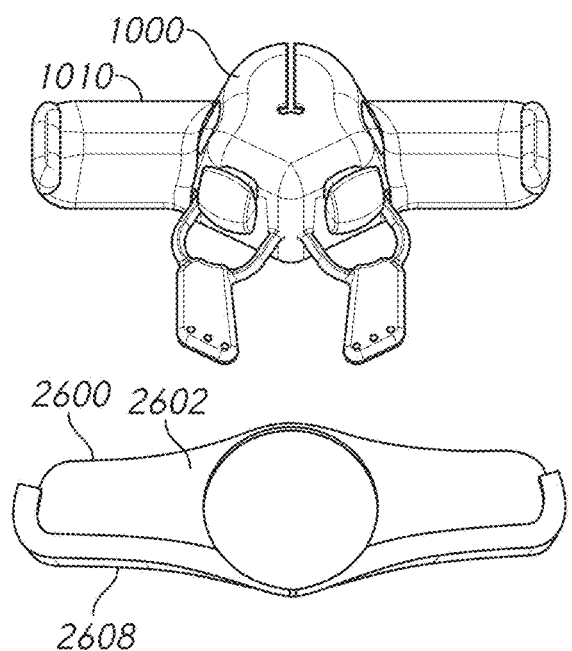
FIG. 26B is an exploded top and back view of the separate base structure of FIG. 26A and a compatible device for protecting a catheter interface.
Figure 26C:
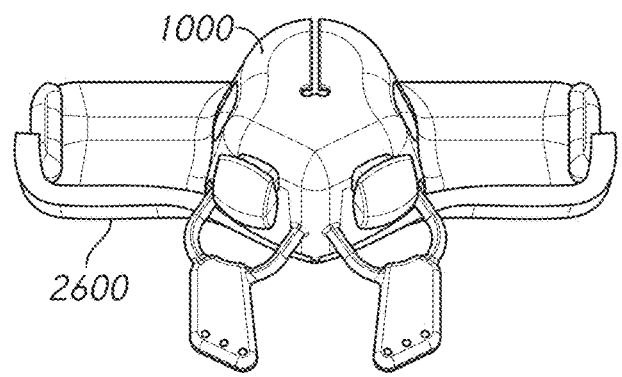
FIG. 26C is a top and back view of the separate base structure of FIG. 26A interacting with the compatible device for protecting a catheter interface.

FIG. 26B is an exploded top and back view of the separate base structure 2600 of FIG. 26A and a compatible device 1000 for protecting a catheter interface. In use, the base structure 2600 is positioned so the hole 2604 is around the umbilical stump, preferably so the wings 2602 are medial-lateral. The device 1000 then interacts with a catheter, for example as described herein, and the flanges 1010 are slid over the wings 2602 and into contact with the lip 2608. FIG. 26C is a top and back view of the separate base structure 2600 of FIG. 26A interacting with the compatible device 1000 for protecting a catheter interface. In embodiments comprising a second lip 2609, the device 1000 can snap into the base structure 2600 past the second lip 2609. Other methods of coupling the base structure 2600 and the device 1000 are also possible. For example, one of the base structure 2600 and the device 1000 could comprise protrusions and the other of the base structure 2600 and the device 1000 could comprise complementary apertures, one of the base structure 2600 and the device 1000 could comprise grooves and the other of the base structure 2600 and the device 1000 could comprise complementary rails, complementary threads (e.g., around the shield 1002 and around the hole 2604), snap fit, friction fit, straps, combinations thereof, and the like. In some embodiments, the base structure 2600 can interact with a modified version of the device 1000 (e.g., not having flanges 1010, having smaller flanges). In some implementations, the contact surfaces of both the base structure 2600 and the device 1000 can be constructed of complementary mating features (e.g., clips, hook-and-loop fastener, magnets, Velcro, combinations thereof, etc.). If desired, tape could be positioned over the flanges 1010 and the wings 2602. The base structure 2600 can secure the device 1000 when desired and allow a user to readily move the device 1000 when desired without removing adhesive (e.g., tape positioned over the flanges 1010) from the subject. Removing and reapplying adhesive can cause skin irritation, so removing that step can advantageously reduce skin irritation and/or enable a user to remove and reposition the device 1000 more often if desired without fear of skin irritation cause by such removal. The base structure 2600 being easily de-coupled and re-coupled to the device 1000 can allow a user to use the device 1000 to temporarily secure a catheter for visualization under radiography, which can reduce or eliminate the need to suture the catheter before catheter location has been confirmed. After visualizing the location under radiography, the user can remove the device 1000 to reposition the catheter if needed, then secure the catheter with sutures, and then reapply the device 1000 onto the base structure 2600 to secure the catheter. The base structure 2600 being separate from the device 1000 allows a user to optionally not use a separate base structure 2600 if desired (e.g., using the device 1000 as described herein (e.g., affixing tape over the flanges 1010)). Various components of the devices disclosed herein may be hypoallergenic including, for example, the base structure 2600 or a portion thereof (e.g., a skin-contact surface thereof). In some embodiments, one or more portions of the devices disclosed herein are free or substantially free of latex, adhesives, and/or other potential skin irritants.

Figure 27A:
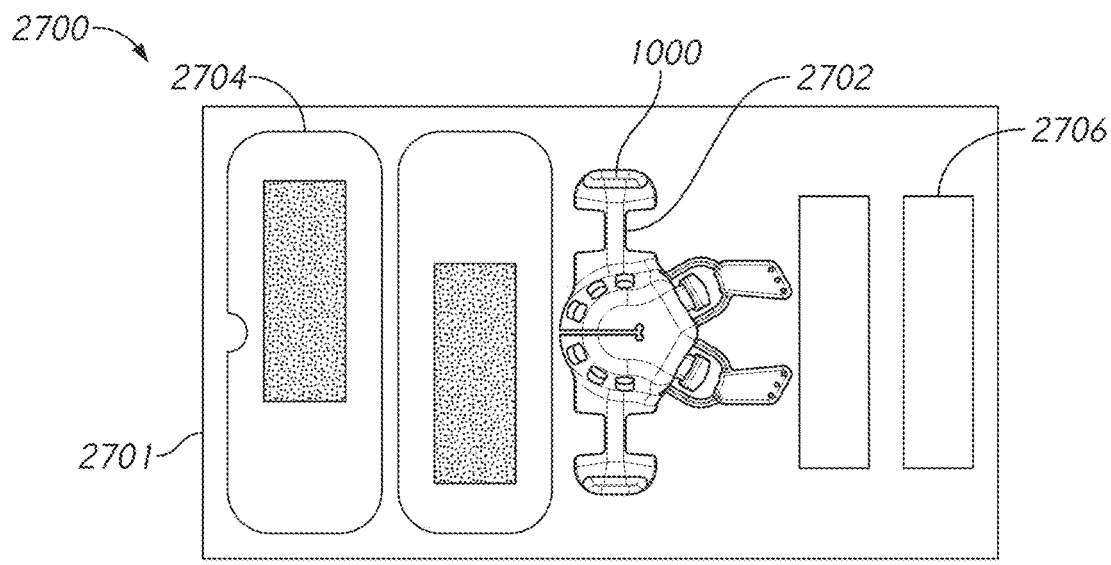
FIG. 27A is a top view of an example kit including a device for protecting a catheter interface.

FIG. 27A is a top view of an example kit 2700 including a device for protecting a catheter interface. FIG. 27A shows the device 1000, but other devices are also possible. In some embodiments, the entire kit may 2700 be sterilized such that the device 1000 and other components of the kit 2700 are sterile until the point of securement to the subject. The kit 2700 may include tabs 2702 (e.g., for positioning over and/or around flanges of the device 1000) for securing the device 1000 in the kit 2700. The kit 2700 may include adhesive 2704 (e.g., hydrocolloid adhesive, silicone-based adhesive, etc.) and adhesive tape 2706. In some embodiments, the kit 2700 may comprise a card 2701 with adhesive 2704 and/or adhesive tape 2706 attached thereto for peeling off and immediate use (e.g., without extra adhesive backing). The adhesive 2704 can be applied to the subject, then the device 1000 can be placed over the adhesive 2704, then the adhesive tape 2706 can be placed over the device 1000. The adhesive 2704 and the adhesive tape 2706 can be dimensioned for interaction with the device 1000, which can improve ease of use and/or standardize care using the device 1000.

Figure 27B:
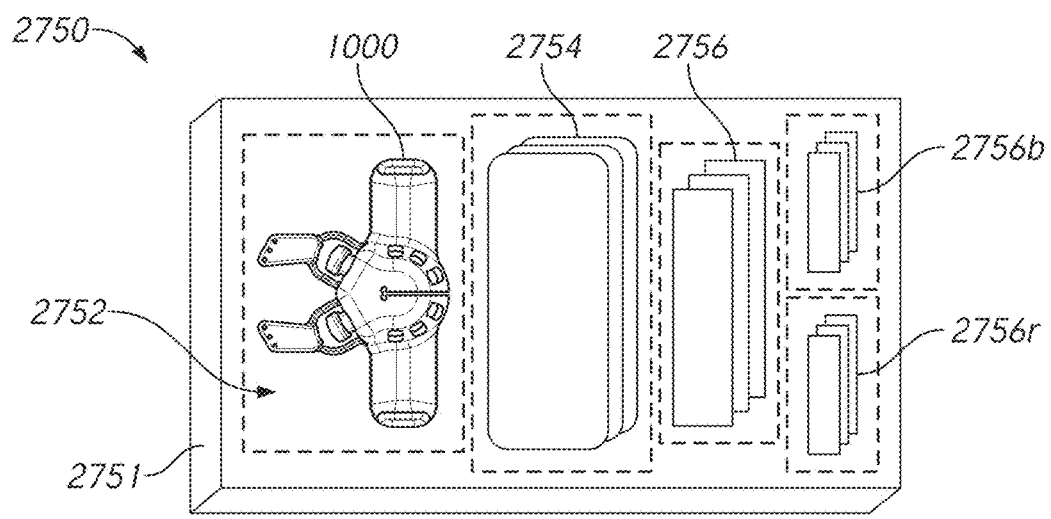
FIG. 27B is a top view of another example kit including a device for protecting a catheter interface.

FIG. 27B is a top view of another example kit 2750 including a device for protecting a catheter interface. FIG. 27B shows the device 1000, but other devices are also possible. In some embodiments, the entire kit May 2750 be sterilized such that the device 1000 and other components of the kit 2750 are sterile until the point of securement to the subject. The kit 2750 may comprise a tray 2751 (e.g., a thermoformed tray) comprising wells 2752 configured to contain certain components. The kit 2750 may include adhesive 2754 (e.g., hydrocolloid adhesive, silicone-based adhesive, etc.) and adhesive tape 2756. In some embodiments, the kit 2750 may comprise the tray 2751 with adhesive 2754 and/or adhesive tape 2756 attached thereto for peeling off and immediate use (e.g., without extra adhesive backing). The adhesive 2754 can be applied to the subject, then the device 1000 can be placed over the adhesive 2754, then the adhesive tape 2756 can be placed over the device 1000. The adhesive 2704 and the adhesive tape 2756 can be dimensioned for interaction with the device 1000, which can improve ease of use and/or standardize care using the device 1000. In some embodiments, a variety of types of adhesive tape 2756 may be provided. For example, red adhesive tape 2756r may be provided for use on an arterial side and blue adhesive tape 2756b may be provided for use on a venous side. The kit 2750 may be sized to accommodate the components therein, for example having a length between about 2 in and about 8 in (e.g., about 2 in, about 3 in, about 4 in, about 5 in, about 6 in, about 7 in, about 8 in, ranges between such values, etc.), a width between about 1 in and about 5 in (e.g., about 1 in, about 2 in, about 3 in, about 4 in, about 5 in, ranges between such values, etc.), and/or a depth between about 0.5 in and about 2 in (e.g., about 0.5 in, about 1 in, about 1.5 in, about 2 in, ranges between such values, etc.). The kit 2750 may include a cover sealed around the edges of the tray 2751 to maintain sterilization until the cover is peeled back. The cover may include tabs or other features configured to aid in peeling. Fewer, more, and/or alternative strips (including non-adhesive strips) are also possible, for example as described with respect to FIGS. 27C and 27D.

Figures 27C, 27D, 27E:
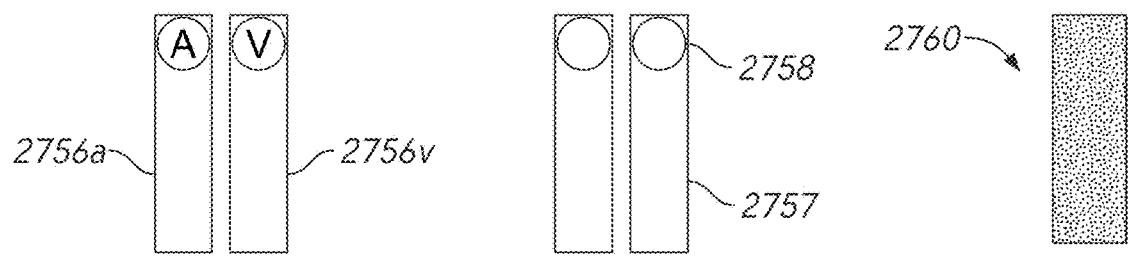
FIG. 27C is a top view of example of adhesive strips.
FIG. 27D is a top view of another example of adhesive strips.
FIG. 27E is a top view of an example air permeable strip.

FIG. 27C is a top view of example of adhesive strips 2756a, 2756v. The strip 2756a comprises indicia indicative of an arterial side, such as the letter "A" and red coloring. The strip 2756v comprises indicia indicative of a venous side, such as the letter "V" and blue coloring. Other indicia are also possible. For example, the strip 2756a may be entirely red (e.g., like the strips 2756r), the strip 2756v may be entirely blue (e.g., like the strips 2756b), etc.

FIG. 27D is a top view of another example of adhesive strips 2757. The strips 2757 comprises an indicia area 2758 so that a user can add indicia indicative of an arterial side, such as the letter "A," or a venous side, such as the letter "V," based on a particular usage. In some embodiments, the indicia area 2758 comprises a writable surface. In some embodiments, stickers or decals may be placed over the indicia area 2758.

FIG. 27E is a top view of an example air permeable strip 2760. The strip 2760 may be included as part of a kit 2700, 2750. After positioning a catheter interface protection device, the strip 2760 may be secured around the device. For example with respect to the device 1000, the strip 2760 may be placed across the slot 1008, for example reducing a width of the slot 1008. For another example with respect to the device 1000, the strip 2760 may be placed across the vents 1004 on the front of the shield 1002, for example protecting the interface from floating debris.

The strips described herein (e.g., the strips 2756a, 2756v, 2756r, 2756b, 2757, 2760) may be non-adhesive. For example, the strips may be configured to mechanically couple to themselves and/or another component (e.g. the device, the catheter, etc.).

Figure 28A:
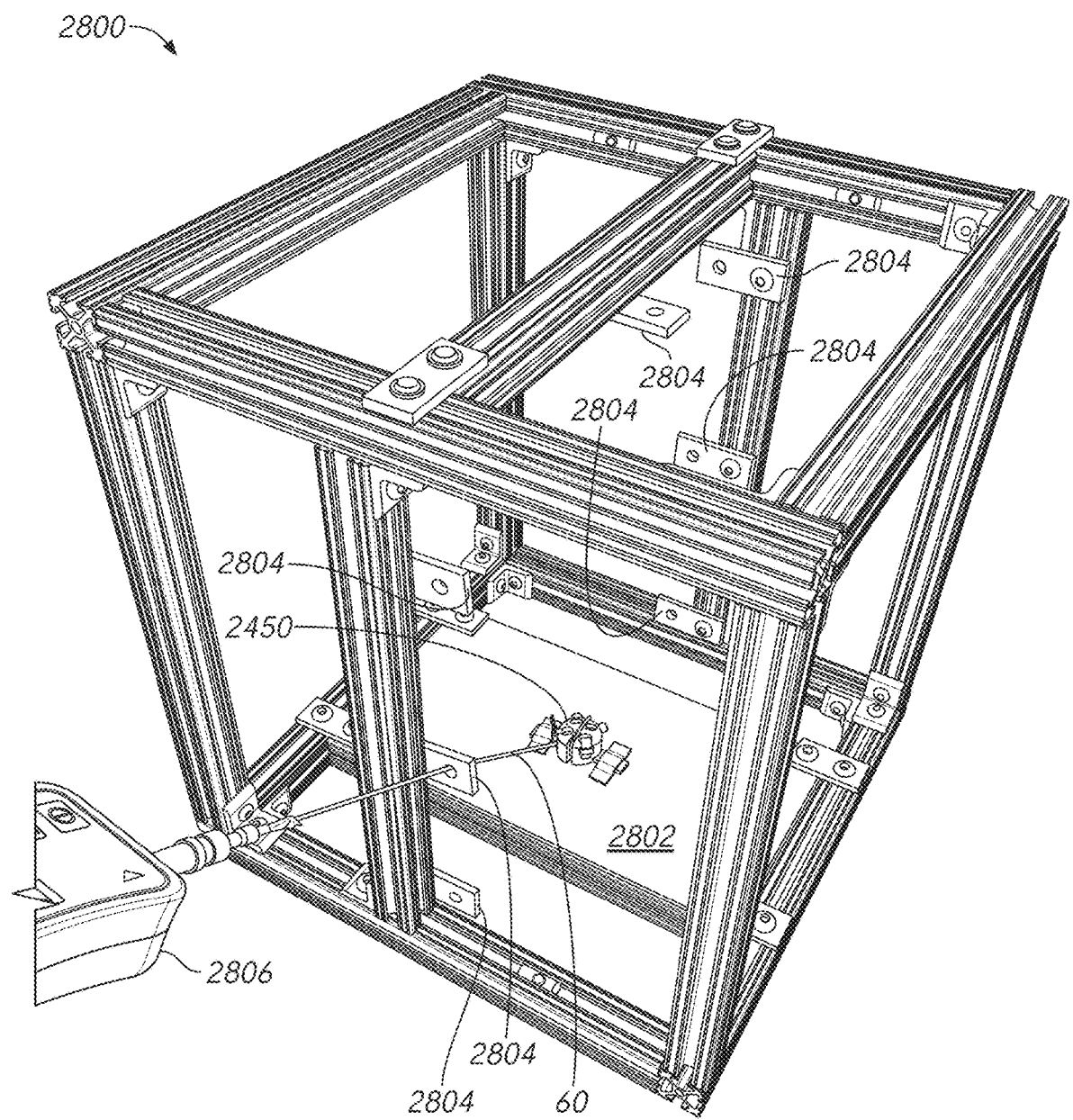
FIG. 28A is a top and side view of an example testing apparatus for a device for protecting a catheter interface.

FIG. 28A is a top and side view of an example testing apparatus 2800 for a device for protecting a catheter interface. The device in FIG. 28A is the device 2450 of FIG. 24F, but the same testing apparatus 2800 can be used for any of the devices described herein and other devices providing the same or similar functions. The testing apparatus 2800 comprises a base 2802 to which the device is secured in the manner that the device would be secured to a subject, for example using tape across flanges (e.g., as shown in FIG. 28A), using an adhesive base structure, etc. The base 2802 may be planar (e.g., as shown in FIG. 28A), concave, convex, angled, etc., which can help to mimic the intended environment of the device. The base 2802 may be rigid (e.g., as shown in FIG. 28A) or flexible, which can help to mimic the intended environment of the device. A catheter 60 extends through and engages with the device in a manner that the device and catheter 60 would interact with a subject. For example, as shown in FIG. 28A and with reference to FIG. 24F, the catheter 60 extends out of an opening on the upper surface of the device 60, towards the back, under a clip, between a strap 2452 and a shield, and having a plug 2454 engaged to a vent 2456. The catheter 60 is coupled to a force gauge 2806. The catheter 60 extends through a test port 2804. The test port 2804 is one of a plurality of test ports 2804 at fixed angles relative to the base 2802. The ports 2804 are arranged at fixed angles and extend about 180° around the device, from approximately parallel to the base 2802 on one side to approximately parallel to the base 2802 on a second side opposite the first side. The testing apparatus 2800 may include ports 2804 spread greater than about 180° (e.g., about 190°, about 200°, about 210°, etc.), for example to mimic potential forces on a subject having a convex belly. The testing apparatus 2800 comprises seven ports 2804, although more ports 2804 or fewer ports 2804 are also possible. For example, the testing apparatus 2800 may comprise between about 3 ports 2804 and about 15 ports 2804 (e.g., about 3 ports, about 5 ports, about 6 ports, about 7 ports, about 8 ports, about 9 ports, about 12 ports, about 15 ports, ranges between such values, etc.).

The testing apparatus 2800 can be used to quantify catheter pulling "failure force" of catheter interface protection devices. As shown in FIG. 28A, the catheter 60 is pulled taut through a port 2804 at a fixed angle using the force gauge 2806 until failure, which may be defined, for example, as movement of the catheter 60 by 5 mm relative to the interface. The force at which failure occurred can be compared to a force limit (e.g., between about 0.5 lb and about 2 lb (e.g., 0.5 lb, 1 lb, 1.5 lb, 2 lb, ranges between such values, etc.)). The force limit may vary based on the angle of the particular port 2804 used for that test. If the interaction is successful at one of the ports 2804, all of the ports 2804, or a certain percentage of the ports (e.g., greater than 50%, greater than 75%), the interaction might be used on a subject.

FIG. 28Bi is a top and side view of another example testing apparatus 2810 for a device for protecting a catheter interface. FIG. 28Bii is an expanded top view of a portion of the testing apparatus 2810 of FIG. 28Bi. The testing apparatus 2810 may include the same or similar features as the testing apparatus 2800. The testing apparatus 2810 comprises a chamber 2812 for controlling relative humidity and/or temperature, which can allow the device to be tested at different conditions. In FIG. 28Bii, the device is visible through the transparent lid of the chamber 2812. Relative humidity may be controlled between about 50% and about 100% (e.g., about 50%, about 60%, about 70%, about 80%, about 90%, about 100%, ranges between such values, etc.). Temperature may be controlled between about 20° C. and about 40° C. (e.g., about 20° C., about 25° C., about 30° C. about 35° C., about 40° C., ranges between such values, etc.). For example, a device may be tested with the chamber 2812 at 80% relative humidity and a temperature of 37° C. In some embodiments, the chamber 2812 may be used to test other conditions, for example, pressure, gaseous environment (e.g., oxygen-rich air), etc.

FIG. 28C is a top and front view of yet another example testing apparatus 2820 for a device for protecting a catheter interface. The device in FIG. 28C is the device 2456 of FIG. 24G, but the same testing apparatus 2820 can be used for any of the devices described herein and other devices providing the same or similar functions. The testing apparatus 2820 comprises a fluid flow testing device 2822 coupled to a catheter 60. The device is secured in the manner that the device would be secured to a subject, for example using tape across flanges (e.g., as shown in FIG. 28C), using an adhesive base structure, etc. A catheter 60 extends through and engages with the device in a manner that the device and catheter 60 would interact with a subject. FIG. 28C shows the use of a piece of tape under the device to mimic the effects of an umbilical stump and vasculature on the catheter 60. The fluid flow testing device 2822 measures cutoff pressure needed to achieve a certain fluid flow rate through the catheter 60 (e.g., about 50%) to test whether the interaction between the device and the catheter 60 impedes the flow of fluid through the catheter 60. If the interaction is successful, the interaction might be used on a subject.

Figure 29A:
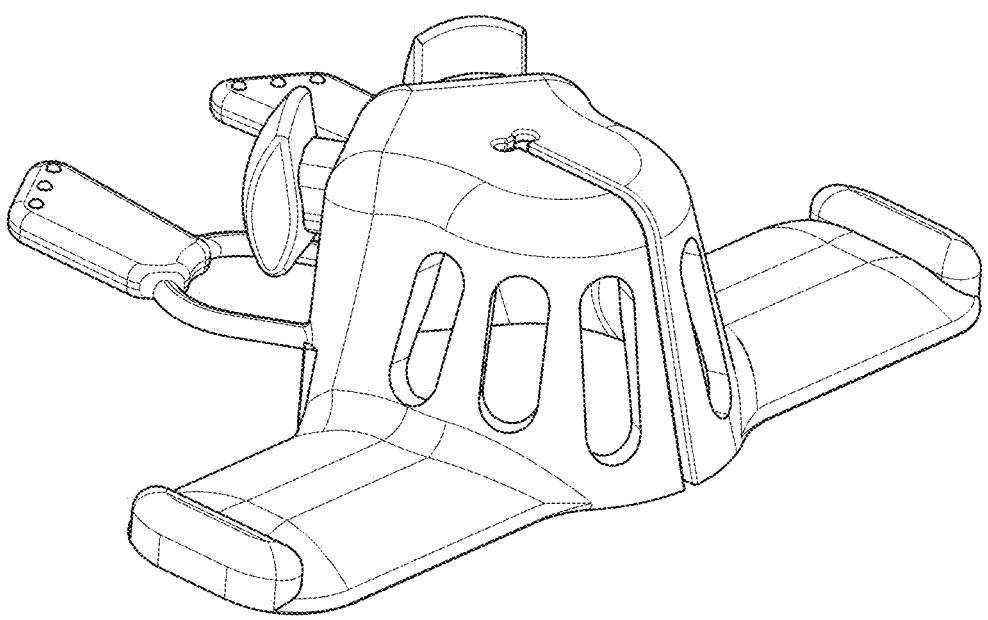
FIG. 29A is a front, left, and top perspective view of a catheter securing system.
Figure 29B:
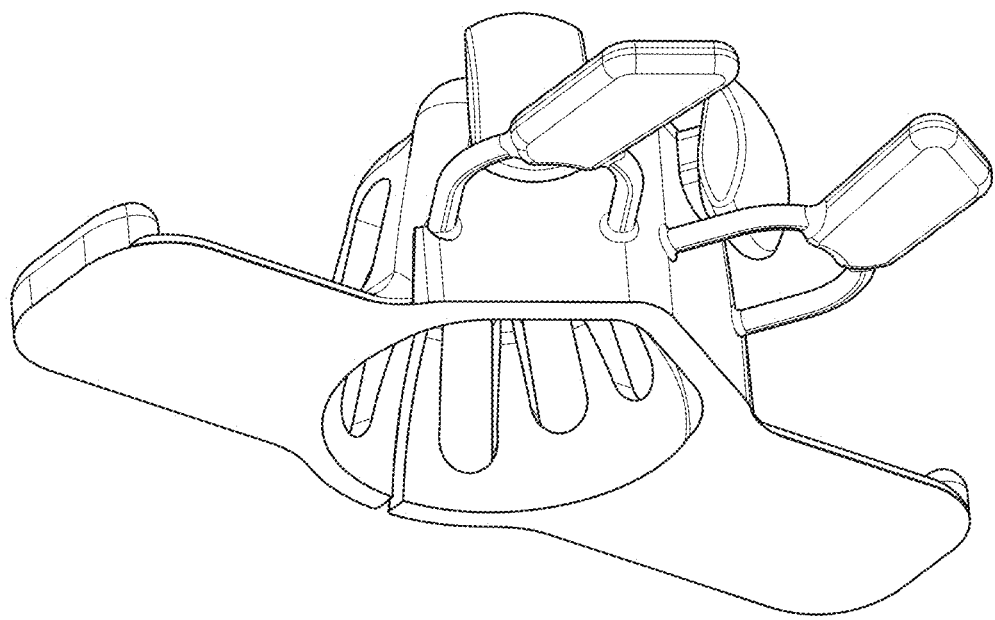
FIG. 29B is a back, right, and bottom perspective view of the catheter securing system of FIG. 29A.
Figure 29C:
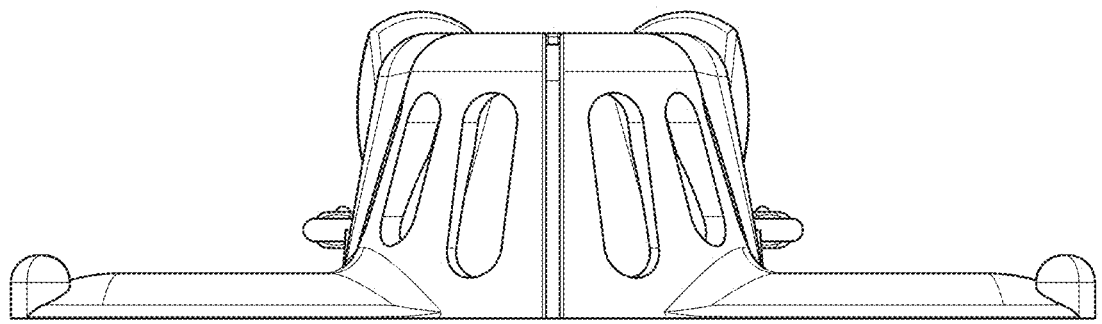
FIG. 29C is a front elevational view of the catheter securing system of FIG. 29A.
Figure 29D:
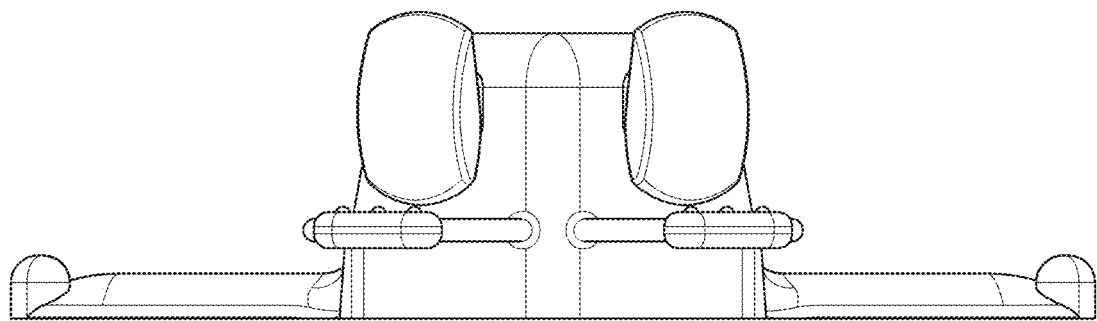
FIG. 29D is a back elevational view of the catheter securing system of FIG. 29A.
Figure 29E:
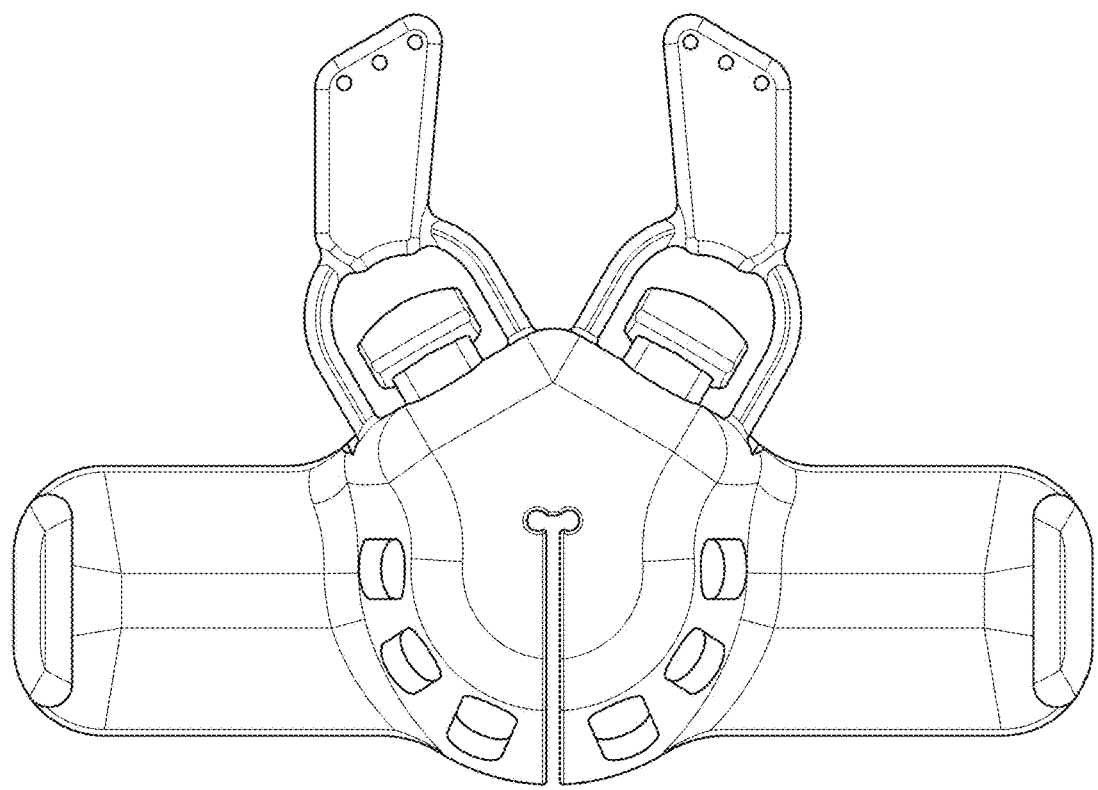
FIG. 29E is a top plan view of the catheter securing system of FIG. 29A.
Figure 29F:
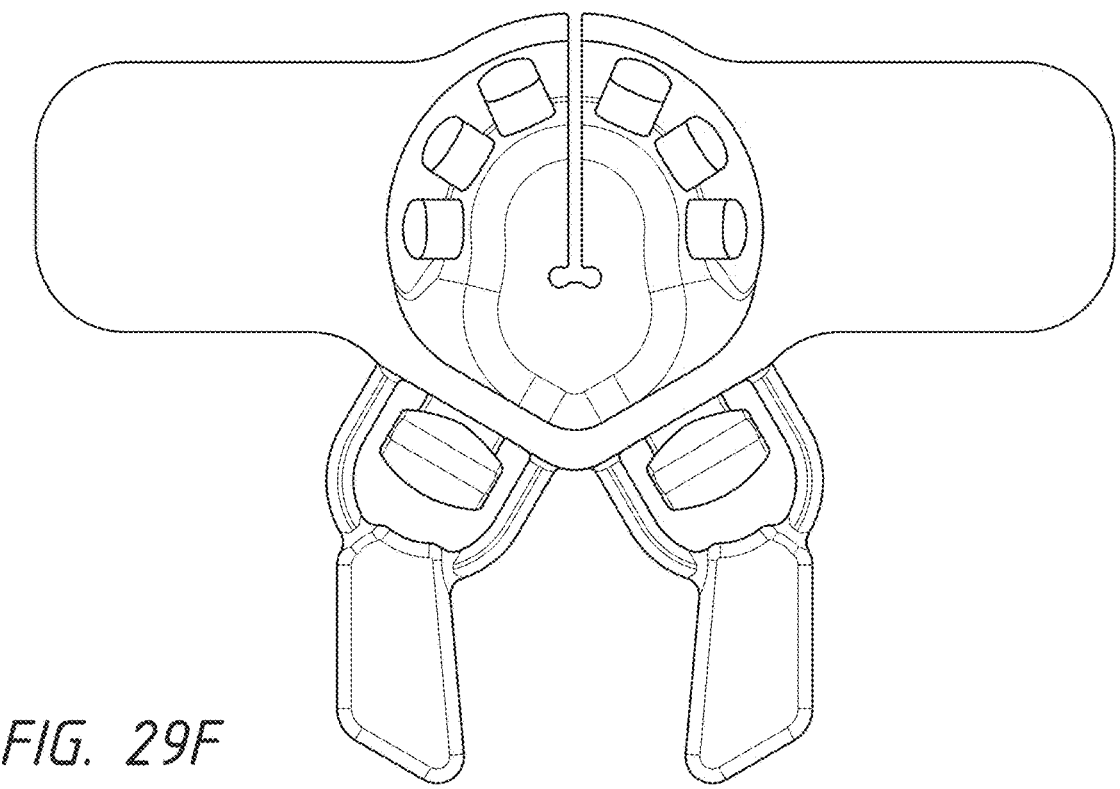
FIG. 29F is a bottom plan view of the catheter securing system of FIG. 29A.
Figure 29G:
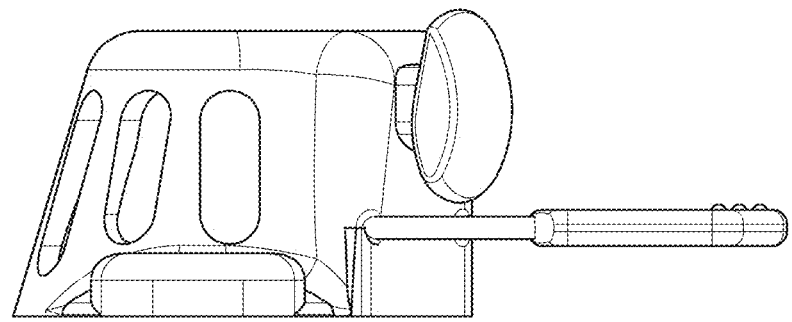
FIG. 29G is a right elevational view of the catheter securing system of FIG. 29A.
Figure 29H:
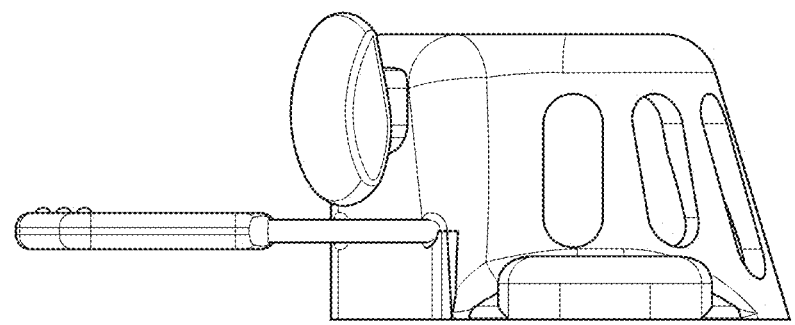
FIG. 29H is a left elevational view of the catheter securing system of FIG. 29A.

FIG. 29A is a front, left, and top perspective view of a catheter securing system. FIG. 29B is a back, right, and bottom perspective view of the catheter securing system of FIG. 29A. FIG. 29C is a front elevational view of the catheter securing system of FIG. 29A. FIG. 29D is a back elevational view of the catheter securing system of FIG. 29A. FIG. 29E is a top plan view of the catheter securing system of FIG. 29A. FIG. 29F is a bottom plan view of the catheter securing system of FIG. 29A. FIG. 29G is a right elevational view of the catheter securing system of FIG. 29A. FIG. 29H is a left elevational view of the catheter securing system of FIG. 29A. The inventors have invented a new, original, and ornamental design for a catheter securing system of which the following is the specification, reference being had to the accompanying drawings, forming a part hereof. In some embodiments, what is claimed is the ornamental design for a catheter securing system, as shown and described (e.g., with respect to FIGS. 29A-29H). Broken line portions and/or solid lines that may be converted into broken line portions show unclaimed subject matter only and would form no part of the claimed design.

The protection devices described herein may be configured to be replaced when a catheter interacting with the device is replaced. For example, an umbilical catheter may be replaced approximately once per week. In some embodiments, the protection devices described herein may be configured to be replaced between once per day and once per month (e.g., once per day, once per 48 hours, once per 72 hours, once per week, once per two weeks, once per month, ranges between such values, etc.).

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

Although some example embodiments have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

While the devices described herein may be used in umbilical stump applications, the devices could also or alternatively be used in applications in which a catheter is extends into a subject, for example, for a duration longer than a percutaneous surgery. In certain such applications, the devices can inhibit movement of the catheter in the subject and/or protect the insertion site. Examples of uses of the devices described herein or modifications thereof can include, for example, surgical line stabilization, mediport access, drains, intracranial pressure monitoring, dialysis access, feeding tubes, colostomy bags, chest tubes, tracheotomy tubes, tracheostomy tubes, and/or any other use where a secure and/or sterile connection would be advantageous to secure and/or protect a line or tube coming out of a body at an angle (e.g., perpendicular).

While the invention is susceptible to various modifications, and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "wrapping the catheter at least partially around a clip of the catheter interface protection device" include "instructing wrapping the catheter at least partially around a clip of the catheter interface protection device." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 1 lb" includes "1 lb." Terms or phrases preceded by a term such as "substantially" include the recited term or phrase. For example, "substantially parallel" includes "parallel."

What is claimed is:

1. A method of protecting a catheter interface, the method comprising:
   providing a catheter interface protection device comprising:
      a shield having an open bottom and a wall that defines a cavity for accommodating an umbilical stump;
      a slot extending from the open bottom along the wall;
      a first clip extending outward from the shield, the first clip comprising an undercut configured to accommodate a portion of a catheter; and
      a first latch coupled to the shield;
   extending the catheter through the slot in the catheter interface protection device;
   wrapping the catheter at least partially around the undercut of the first clip; and
   securing the first latch around the first clip.

2. The method of claim 1, wherein wrapping the catheter at least partially around the undercut of the first clip comprises changing a direction of the catheter at least twice between the catheter interface and a proximal end of the catheter.

3. The method of claim 1, wherein wrapping the catheter at least partially around the first clip comprises wrapping the catheter at least once around the first clip.

4. The method of claim 1, wherein wrapping the catheter at least partially around the first clip comprises manipulating the catheter on a plane generally parallel to a longitudinal axis of the catheter interface protection device.

5. The method of claim 1, further comprising wrapping the catheter at least partially around a second undercut of a second clip that extends outward from the shield.

6. The method of claim 1, further comprising extending a second catheter through the slot in the catheter interface protection device.

7. The method of claim 6, further comprising wrapping the second catheter at least partially around an undercut of a second clip that extends outward from the shield.

8. The method of claim 1, further comprising detaching the catheter interface protection device to a subject.

9. A method of protecting a catheter interface, the method comprising:
   providing a catheter interface protection device comprising:
      a shield having an open bottom and a wall that defines a cavity for accommodating an umbilical stump;
      a slot in the shield configured to allow a catheter to extend therethrough; and
      a first clip extending outward from the shield, the first clip configured to accommodate at least a portion of the catheter;
   at least partially securing a first portion of the catheter by extending the catheter through the slot;
   at least partially securing a second portion of the catheter; and
   locking the second portion of the catheter in place.

10. The method of claim 9, wherein at least partially securing the second portion of the catheter comprises wrapping the second portion of the catheter at least partially around the first clip.

11. The method of claim 10, wherein wrapping the second portion of the catheter at least partially around the first clip comprises manipulating the catheter on a plane generally parallel to a longitudinal axis of the catheter interface protection device.

12. The method of claim 11, further comprising wrapping a third portion the catheter at least partially around a second clip extending outward from the shield.

13. The method of claim 12, further comprising locking the third portion of the catheter in place.

14. The method of claim 9, further comprising at least partially securing a first portion of a second catheter by extending the catheter through the slot.

15. The method of claim 14, further comprising at least partially securing a second portion of the second catheter around a second clip extending outward from the shield.

16. The method of claim 15, wherein at least partially securing the second portion of the second catheter comprises wrapping the second portion of the second catheter at least partially around the second clip.

17. The method of claim 16, further comprising locking the second portion of the second catheter in place.

18. The method of claim 17, wherein locking the second portion of the second catheter in place comprises manipulating a second latch to engage the second clip and the second catheter.

19. The method of claim 9, wherein locking the second portion of the catheter in place comprises manipulating a first latch to engage the first clip and the catheter.

20. The method of claim 19, wherein:
locking the second portion of the catheter in place comprises manipulating the first latch between a first configuration and a second configuration;
when the first latch is in the first configuration, the first latch is positioned away from the first clip;
when the first latch is in the second configuration, the first latch engages the first clip and the catheter.

\* \* \* \* \*